(12) United States Patent
Siebel

(10) Patent No.: US 9,200,071 B2
(45) Date of Patent: Dec. 1, 2015

(54) METHODS OF TREATING CANCER USING NOTCH1 AND NOTCH3 ANTAGONISTS

(75) Inventor: Christian W. Siebel, Berkeley, CA (US)

(73) Assignee: Genentech, Inc., South San Francisco, CA (US)

( * ) Notice: Subject to any disclaimer, the term of this patent is extended or adjusted under 35 U.S.C. 154(b) by 90 days.

(21) Appl. No.: 13/498,560

(22) PCT Filed: Sep. 29, 2010

(86) PCT No.: PCT/US2010/050610
§ 371 (c)(1),
(2), (4) Date: Jun. 1, 2012

(87) PCT Pub. No.: WO2011/041336
PCT Pub. Date: Apr. 7, 2011

(65) Prior Publication Data
US 2012/0328608 A1    Dec. 27, 2012

Related U.S. Application Data

(60) Provisional application No. 61/247,298, filed on Sep. 30, 2009.

(51) Int. Cl.
*C07K 16/28* (2006.01)
*A61K 39/395* (2006.01)
*A61K 39/00* (2006.01)

(52) U.S. Cl.
CPC ............ *C07K 16/28* (2013.01); *A61K 39/39558* (2013.01); *A61K 2039/505* (2013.01); *C07K 16/2863* (2013.01); *C07K 16/2866* (2013.01); *C07K 2316/96* (2013.01); *C07K 2317/34* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 2008/0118520 | A1 | 5/2008 | Li et al. |
| 2008/0226621 | A1 | 9/2008 | Fung et al. |
| 2009/0047285 | A1* | 2/2009 | Gurney et al. ............. 424/139.1 |
| 2009/0081238 | A1 | 3/2009 | Siebel et al. |
| 2010/0111958 | A1* | 5/2010 | Gurney et al. ............. 424/139.1 |
| 2012/0093813 | A1* | 4/2012 | Li et al. ...................... 424/133.1 |

FOREIGN PATENT DOCUMENTS

| WO | 2008/076960 | 6/2008 |
| WO | 2008/091641 | 7/2008 |
| WO | 2008/108910 | 9/2008 |
| WO | 2008/136848 | 11/2008 |
| WO | WO 2008/150525 A1 | 12/2008 |
| WO | WO-2010141249 A2 * | 12/2010 |

OTHER PUBLICATIONS

Agnusdei et al. Therapeutic antibody targeting of Notch1 in T-acute lymphoblastic leukemia xenografts. Leukemia (2013), pp. 1-11.*
Ma et al. Notch1 signaling promotes human t-cell acute lymphoblastic leukemia initiating cell regeneration in supportive niches. PLoS One 7(6): e39725, 2012, 14 pages.*
"NCI-60 DTP human tumor cell line screen"; website dtp.nci.nih.gov/branches/btb/hfa.html; downloaded Jan. 9, 2014, 2 pages.*
"Primary anti-cancer drug screening activities"; website dtp.nci.nih.gov/branches/btb/ivclsp.html; downloaded Jan. 9, 2014, 3 pages.*
Wu et al. Therapeutic antibody targeting of individual Notch receptors. Nature 464: 1052-1057, 2010.*
Palermo et al. Acetylation controls Notch3 stability and function in T-cell leukemia. Oncogene 31: 3807-3817, 2012.*
Masiero et al. Notch3-mediated regulation of MKP-1 levels promotes survival of T acute lymphoblastic leukemia cells. Leukemia 25: 588-298, 2011.*
Wu et al., "Notch Signaling and its role in breast cancer" Frontiers in Bioscience 12:4370-4383 ( 2007)
Jundt et al., "Activated Notch1 signaling promotes tumor cell proliferation and survival in Hodgkin and anaplastic large cell lymphoma" Blood 99(9):3398-3403 (May 1, 2002)
Kogoshi et al., "γ-Secretase inhibitors suppress the growth of leukemia and lymphoma cells" Oncology Reports 18:77-80 ( 2007)
Koch et al., "Notch and Cancer: a double-edged sword" Cellular and Molecular Life Sciences.64:2746-2762 ( 2007)
Mullendore et al., "Ligand-dependent Notch Signaling is Involved in Tumor Initiation and Tumor Maintenance in Pancreatic Cancer" Clinical Cancer Research 15:2291-2301 (Apr. 1, 2009).
Pui et al., "Notch1 Expresssion in Early Lymphopoiesis Influences B versus T Lineage Determination" Immunity 11:299-308 ( 1999).
Allenspach et al. "Notch signaling in cancer" Cancer Biol Ther 1(5):466-76 ( 2002).
Palomero et al., "Activating mutations in Notch 1 in acute myeloid leukemia and lineage switch leukemias" Leukemia 20:1963-1966 ( 2006).
Aster et al., "Essential roles for ankyrin repeat and transactivation domains in induction of T-cell leukemia by notch1" Mol Cell Biol. 20(20):7505-15 (Oct. 2000).
Bellavia et al., "Constitutive activation of NF-kappaB and T-cell leukemia/lymphoma in Notch3 transgenic mice" Embo J. 19(13):3337-48 ( 2000).
Bellavia et al., "Combined expression of pTalpha and Notch3 in T cell leukemia identifies the requirement of preTCR for leukemogenesis" P Natl Acad Sci USA 99(5):3788-93 (Mar. 2002).
Aster et al., "Notch Signaling in leukemia" Annu Rev Pathol Mech Dis 3:587-613 ( 2008).
Deangelo et al., "A phase I clinical trial of the notch inhibitor MK-0752 in patients with T-cell acute lymphoblastic leukemia/lymphoma (T-ALL) and other leukemias" J Clin Oncol (ASCO Meeting Abstracts: 6585), 24(18S):2 pages (Jun. 20, 2006).

(Continued)

*Primary Examiner* — Bridget E Bunner

(74) *Attorney, Agent, or Firm* — McNeill Baur PLLC

(57) ABSTRACT

The present invention relates to methods of treating cancer in general, and leukemia in particular, using Notch1 and Notch3 antagonists singly or in combination. Compositions and methods for the treatment and diagnosis of Notch-associated cancers are also provided.

16 Claims, 25 Drawing Sheets

(56) References Cited

OTHER PUBLICATIONS

Roy et al., "The multifaceted role of Notch in cancer" Curr Opin Genet Dev. 17(1):52-9 (Feb. 2007).

Joshi et al., "Notch signaling mediates G1/S cell-cycle progression in T cells via cyclin D3 and its dependent kinases" Blood 113(8):1689-1698 (Feb. 19, 2009).

Jurynczyk et al., "Notch3 Inhibition in Myelin-Reactive T Cells Down-Regulates Protein Kinase Cθ and Attenuates Experimental Autoimmune Encephalomyelitis" Journal of Immunology 180(4):2634-2640 (2008).

Li et al., "Modulation of Notch Signaling by Antibodies Specific for the Extracellular Negative Regulatory Region of NOTCH3" Journal of Biological Chemistry 283(12):8046-8054 (Mar. 21, 2008).

Miele et al., "Notch Signaling as a Novel Cancer Therapeutic Target" Current Cancer Drug Targets 6:313-323 (2006).

Ellisen et al., "TAN-1, the human homolog of the Drosophila notch gene, is broken by chromosomal translocations in T lymphoblastic neoplasms" Cell 66(4):649-61 (Aug. 1991).

Ersvaer et al., "Future Perspectives: Therapeutic Targeting of Notch Signalling May Become a Strategy in Patients Receiving Stem Cell Transplantation for Hematologic Malignancies" Bone Marrow Research 2011:1-16 (Jul. 2010).

Ishida et al., "Cadisil with a Novel Mutation in Exon 7 of NOTCH3 (C388Y)" Internal Medicine 45(16):981-985 (Sep. 15, 2006).

Notice of Reasons for Rejection, for Japanese Patent Application No. 2012-532248, issued Jul. 7, 2015, including English translation (6 pages).

* cited by examiner 90.7% identity in 2556 residues overlap; Score: 13215.0; Gap frequency: 1.0%

```
Human    1    MPPLLAPLLCLALLPALAARGPRCSQPGETCLNGGKCEAANGTEACVCGGAFVGPRCQDP
Mouse    1    MPRLLTPLLCLTLLPALAARGLRCSQPSGTCLNGGRCEVASGTEACVCSGAFVGQRCQDS
              ** ** ***** ******** ***** ****** ** * ****** **** **** ****
              ─────────────── ──────────────────
              Signal Peptide       EGF1

Human    61   NPCLSTPCKNAGTCHVVDRRGVADYACSCALGFSGPLCLTPLDNACLTNPCRNGGTCDLL
Mouse    61   NPCLSTPCKNAGTCHVVDHGGTVDYACSCPLGFSGPLCLTPLDNACLANPCRNGGTCDLL
              ******************  *  ****** ***************** **********
              ───────────────────────────── ──────────
                       EGF2                       EGF3

Human    121  TLTEYKCRCPPGWSGKSCQQADPCASNPCANGGQCLPFEASYICHCPPSFHGPTCRQDVN
Mouse    121  TLTEYKCRCPPGWSGKSCQQADPCASNPCANGGQCLPFESSYICRCPPGFHGPTCRQDVN
              ************************************** **** *** **********
              ────────────────────────────────────
                                 EGF4

Human    181  ECGQKPGLCRHGGTCHNEVGSYRCVCRATHTGPNCERPYVPCSPSPCQNGGTCRPTGDVT
Mouse    181  ECSQNPGLCRHGGTCHNEIGSYRCACRATHTGPHCELPYVPCSPSPCQNGGTCRPTGDTT
              ** * ************* ***** ******** ** ****************** *
              ─────────────────────────────── ──────────
                         EGF5                      EGF6

Human    241  HECACLPGFTGQNCEENIDDCPGNNCKNGGACVDGVNTYNCRCPPEWTGQYCTEDVDECQ
Mouse    241  HECACLPGFAGQNCEENVDDCPGNNCKNGGACVDGVNTYNCRCPPEWTGQYCTEDVDECQ
              ********* ******* ******************************************
              ───────────────────── ──────────────
                       EGF7                         EGF8

Human    301  LMPNACQNGGTCHNTHGGYNCVCVNGWTGEDCSENIDDCASAACFHGATCHDRVASFYCE
Mouse    301  LMPNACQNGGTCHNTHGGYNCVCVNGWTGEDCSENIDDCASAACFQGATCHDRVASFYCE
              ********************************************* **************
              ──────────────────────── ─────────
                                   EGF9

Human    361  CPHGRTGLLCHLNDACISNPCNEGSNCDTNPVNGKAICTCPSGYTGPACSQDVDECSLGA
Mouse    361  CPHGRTGLLCHLNDACISNPCNEGSNCDTNPVNGKAICTCPSGYTGPACSQDVDECALGA
              ******************************************************* ***
              ────────── ────────────────────── ──────
                 EGF10                                   EGF11

Human    421  NPCEHAGKCINTLGSFECQCLQGYTGPRCEIDVNECVSNPCQNDATCLDQIGEFQCICMP
Mouse    421  NPCEHAGKCLNTLGSFECQCLQGYTGPRCEIDVNECISNPCQNDATCLDQIGEFQCICMP
              ********* ************************** ***********************
              ──────── ─────────────────────── ─────
                                        EGF12

Human    481  GYEGVHCEVNTDECASSPCLHNGRCLDKINEFQCECPTGFTGHLCQYDVDECASTPCKNG
Mouse    481  GYEGVYCEINTDECASSPCLHNGHCMDKINEFQCQCPKGFNGHLCQYDVDECASTPCKNG
              ***** ** ************** * ******* ** ** ****************
              ─────── ────────────────── ─────────
                EGF13                                      EGF14

Human    541  AKCLDGPNTYTCVCTEGYTGTHCEVDIDECDPDPCHYGSCKDGVATFTCLCRPGYTGHHC
Mouse    541  AKCLDGPNTYTCVCTEGYTGTHCEVDIDECDPDPCHYGSCKDGVATFTCLQPGYTGHHC
              ************************************************* ********
              ──────────────────────────────────
                                 EGF15

Human    601  ETNINECSSQPCRHGGTCQDRDNAYLCFCLKGTTGPNCEINLDDCASSPCDSGTCLDKID
Mouse    601  ETNINECHSQPCRHGGTCQDRDNSYLCLCLKGTTGPNCEINLDDCASNPCDSGTCLDKID
              ******* *************** *** ******************* ***********
              ─ ──────────────────── ─────────────────
                   EGF16                        EGF17
```

*FIG. 1A*

```
Human    661  GYECACEPGYTGSMCNINIDECAGNPCHNGGTCEDGINGFTCRCPEGYHDPTCLSEVNEC
Mouse    661  GYECACEPGYTGSMCNVNIDECAGSPCHNGGTCEDGIAGFTCRCPEGYHDPTCLSEVNEC
              *************** ****** ************ ***********************
              ──────────────  ═══════════════════════════════  ──────────
                                        EGF18                    EGF19

Human    721  NSNPCVHGACRDSLNGYKCDCDPGWSGTNCDINNNECESNPCVNGGTCKDMTSGYVCTCR
Mouse    721  NSNPCIHGACRDGLNGYKCDCAPGWSGTNCDINNNECESNPCVNGGTCKDMTSGYVCTCR
              ***** ****** ******** **************************************
              ═══════════════════════════════════════
                                EGF20

Human    781  EGFSGPNCQTNINECASNPCLNQGTCIDDVAGYKCNCLLPYTGATCEVVLAPCAPSPCRN
Mouse    781  EGFSGPNCQTNINECASNPCLNQGTCIDDVAGYKCNCPLPYTGATCEVVLAPCATSPCKN
              ************************************ **************** *** *
              ──  ═══════════════════════════════  ──────────────
                        EGF21                              EGF22

Human    841  GGECRQSEDYESFSCVCPTGWQGQTCEVDINECVLSPCRHGASCQNTHGGYRCHCQAGYS
Mouse    841  SGVCKESEDYESFSCVCPTGWQGQTCEVDINECVKSPCRHGASCQNTNGSYRCLCQAGYT
              * * ****************************** ************ * *** *****
              ═════════════════════════════════════════════
                                    EGF23

Human    901  GRNCETDIDDCRPNPCHNGGSCTDGINTAFCDCLPGFRGTFCEEDINECASDPCRNGANC
Mouse    901  GRNCESDIDDCRPNPCHNGGSCTDGINTAFCDCLPGFQGAFCEEDINECASNPCQNGANC
              ***** ******************************* * ********** ** *****
              ──  ═══════════════════════════════════  ──────────────
                        EG24                                    EGF25

Human    961  TDCVDSYTCTCPAGFSGIHCENNTPDCTESSCFNGGTCVDGINSFTCLCPPGFTGSYCQH
Mouse    961  TDCVDSYTCTCPVGFNGIHCENNTPDCTESSCFNGGTCVDGINSFTCLCPPGFTGSYCQY
              ************ ** ******************************************
                          ═══════════════════════════════════════
                                        EGF26

Human   1021  DVNECDSQPCLHGGTCQDGCGSYRCTCPQGYTGPNCQNLVHWCDSSPCKNGGKCWQTHTQ
Mouse   1021  DVNECDSRPCLHGGTCQDSYGTYKCTCPQGYTGLNCQNLVRWCDSAPCKNGGRCWQTNTQ
              ******* **********   * * ******** ****** **** ****** **** **
              ═══════════════════════════════════════  ──────────────
                                EGF27                          EGF28

Human   1081  YRCECPSGWTGLYCDVPSVSCEVAAQRQGVDVARLCQHGGLCVDAGNTHHCRCQAGYTGS
Mouse   1081  YHCECRSGWTGVNCDVLSVSCEVAAQKRGIDVTLLCQHGGLCVDEGDKHYCHCQAGYTGS
              * *** ***** *** ********  * ***  *********** *  * * ********
              ──────────────────────────────────────
                                EGF29

Human   1141  YCEDLVDECSPSPCQNGATCTDYLGGYSCKCVAGYHGVNCSEEIDECLSHPCQNGGTCLD
Mouse   1141  YCEDEVDECSPNPCQNGATCTDYLGGFSCKCVAGYHGSNCSEEINECLSQPCQNGGTCID
              **** ****** ************** ********* ****** **** ******** *
              ═══  ══════════════════════════════════════
                EGF30                              EGF31

Human   1201  LPNTYKCSCPRGTQGVHCEINVDDCNPPVDPVSRSPKCFNNGTCVDQVGGYSCTCPPGFV
Mouse   1201  LTNSYKCSCPRGTQGVHCEINVDDCHPPLDPASRSPKCFNNGTCVDQVGGYTCTCPPGFV
              * * ********************* ** ** ******************* ********
              ──────────────────────────────────
                            EGF32

Human   1261  GERCEGDVNECLSNPCDARGTQNCVQRVNDFHCECRAGHTGRRCESVINGCKGKPCKNGG
Mouse   1261  GERCEGDVNECLSNPCDPRGTQNCVQRVNDFHCECRAGHTGRRCESVINGCRGKPCKNGG
              ***************** ******************************** ********
              ═════════════════════════                  ─────────────
                        EGF33                                  EGF34
```

*FIG. 1B*

```
Human  1321  TCAVASNTARGFICKCPAGFEGATCENDARTCGSLRCLNGGTCISGPRSPTCLCLGPFTG
Mouse  1321  VCAVASNTARGFICRCPAGFEGATCENDARTCGSLRCLNGGTCISGPRSPTCLCLGSFTG
             ********** *** *********************************************  ***
                                                            EGF35

Human  1381  PECQFPASSPCLGGNPCYNQGTCEPTSESPFYRCLPAKFNGLLCHILDYSFGGGAGRDI
Mouse  1381  PECQFPASSPCVGSNPCYNQGTCEPTSENPFYRCLPAKFNGLLCHILDYSFTGGAGRDI
             *********** * *************  *********************** ******
                    EGF36

Human  1441  PPPLIEEACELPECQEDAGNKVCSLQCNNHACGWDGGDCSLNFNDPWKNCTQSLQCWKYF
Mouse  1441  PPPQIEEACELPECQVDAGNKVCNLQCNNHACGWDGGDCSLNFNDPWKNCTQSLQCWKYF
             *** ********** ******* *************************************
                              LNR_A                                   LNR_B Human  1501  SDGHCDSQCNSAGCLFDGFDCQRAEGQCNPLYDQYCKDHFSDGHCDQGCNSAECEWDGLD
Mouse  1501  SDGHCDSQCNSAGCLFDGFDCQLTEGQCNPLYDQYCKDHFSDGHCDQGCNSAECEWDGLD
             ********************** **** ********************************
                                     LNR_C Human  1561  CAEHVPERLAAGTLVVVVLMPPEQLRNSSFHFLRELSRVLHTNVVFKRDAHGQQMIFPYY
Mouse  1561  CAEHVPERLAAGTLVLVVLLPPDQLRNNSFHFLRELSHVLHTNVVFKRDAQGQQMIFPYY
             *************** *** ** **** ******** ************* *********
                      HD-N Human  1621  GREEELRKHPIKRAAEGWAAPDALLGQVKASLLPGGSEGGRRRRELDPMDVRGSIVYLEI
Mouse  1621  GHEEELRKHPIKRSTVGWAT---------SSLLPGTS-GGRQRRELDPMDIRGSIVYLEI
             * **********   ***           ****  *  ***  ********* *******
                                                              S1  HD-C Human  1681  DNRQCVQASSQCFQSATDVAAFLGALASLGSLNIPYKIEAVQSETVEPPPPAQLHFMYVA
Mouse  1671  DNRQCVQSSSQCFQSATDVAAFLGALASLGSLNIPYKIEAVKSEPVEPPLPSQLHLMYVA
             ******* ******************************** ** **** *  *** ****
                                                    S2                 TM Human  1741  AAAFVLLFFVGCGVLLSRKRRRQHGQLWFPEGFKVSEASKKKKRREPLGEDSVGLKPLKNA
Mouse  1731  AAAFVLLFFVGCGVLLSRKRRRQHGQLWFPEGFKVSEASKKKKRREPLGEDSVGLKPLKNA
             ************************************************************

Human  1801  SDGALMDDNQNEWGDEDLETKKFRFEEPVVLPDLDDQTDHRQWTQQHLDAADLRMSAMAP
Mouse  1791  SDGALMDDNQNEWGDEDLETKKFRFEEPVVLPDLSDQTDHRQWTQQHLDAADLRMSAMAP
             ********************************** *************************

Human  1861  TPPQGEVDADCMDVNVRGPDGFTPLMIASCSGGGLETGNSEEEEDAPAVISDFIYQGASL
Mouse  1851  TPPQGEVDADCMDVNVRGPDGFTPLMIASCSGGGLETGNSEEEEDAPAVISDFIYQGASL
             ************************************************************

Human  1921  HNQTDRTGETALHLAARYSRSDAAKRLLEASADANIQDNMGRTPLHAAVSADAQGVFQIL
Mouse  1911  HNQTDRTGETALHLAARYSRSDAAKRLLEASADANIQDNMGRTPLHAAVSADAQGVFQIL
             ************************************************************
```

*FIG. 1C*

```
Human   1981   IRNRATDLDARMHDGTTPLILAARLAVEGMLEDLINSHADVNAVDDLGKSALHWAAAVNN
Mouse   1971   LRNRATDLDARMHDGTTPLILAARLAVEGMLEDLINSHADVNAVDDLGKSALHWAAAVNN
               ************************************************************

Human   2041   VDAAVVLLKNGANKDMQNNREETPLFLAAREGSYETAKVLLDHFANRDITDHMDRLPRDI
Mouse   2031   VDAAVVLLKNGANKDMQNNKEETPLFLAAREGSYETAKVLLDHFANRDITDHMDRLPRDI
               ******************* ****************************************

Human   2101   AQERMHHDIVRLLDEYNLVRSPQLHGAPLGGTPTLSPPLCSPNGYLGSLKPGVQGKKVRK
Mouse   2091   AQERMHHDIVRLLDEYNLVRSPQLHGTALGGTPTLSPTLCSPNGYLGNLKSATQGKKARK
               ************************** ********* ********* **  ****  *

Human   2161   PSSKGLACGSKEAKDLKARRKKSQDGKGCLLDSSGMLSPVDSLESPHGYLSDVASPPLLP
Mouse   2151   PSTKGLACGSKEAKDLKARRKKSQDGKGCLLDSSSMLSPVDSLESPHGYLSDVASPPLLP
               ** ******************************* *************************

Human   2221   SPFQQSPSVPLNHLPGMPDTHLGIGHLNVAAKPEMAALGGGGRLAFETGPPRLSHLPVAS
Mouse   2211   SPFQQSPSMPLSHLPGMPDTHLGISHLNVAAKPEMAALAGGSRLAFEPPPPRLSHLPVAS
               ******** ** ************ ************ ** ***** *  *********

Human   2281   GTSTVLGSSSGGALNFTVGGSTSLNGQCEWLSRLQSGMVPNQYNPLRGSVAPGPLSTQAP
Mouse   2271   SASTVLSTNGTGAMNFTVGAPASLNGQCEWLPRLQNGMVPSQYNPLRPGVTPGTLSTQAA
               ****   **  ***** ********** *** ***** ***** ***  * **  *****

Human   2341   SLQHGMVGPLHSSLAASALSQMMSYQGLPSTRLATQPHLVQTQQVQPQNLQMQQQNLQPA
Mouse   2331   GLQHSMMGPLHSSLSTNTLSPII-YQGLPNTRLATQPHLVQTQQVQPQNLQLQPQNLQP-
               *** * *******    **     ***** ********************* * *****

Human   2401   NIQQQQSLQPPPPPPQPHLGVSSAASGHLGRSFLSGEPSQADVQPLGPSSLAVHTILPQE
Mouse   2389   -------------PSQPHLSVSSAANGHLGRSFLSGEPSQADVQPLGPSSLPVHTILPQE
                            * **** ***** ************************* ********

Human   2461   SPALPTSLPSSLVPPVTAAQFLTPPSQHSYSS-PVDNTPSHQLQVPEHPFLTPSPESPDQ
Mouse   2436   SQALPTSLPSSMVPPMTTTQFLTPPSQHSYSSSPVDNTPSHQLQVPEHPFLTPSPESPDQ
               * ********* *** *  ************ ****************************

Human   2520   WSSSSPHSNVSDWSEGVSSPPTSMQSQIARIPEAFK
Mouse   2496   WSSSSPHSNISDWSEGISSPPTTMPSQITHIPEAFK
               ********* ****** ***** *  * *  *****
```

FIG. 1D

Amino Acid Sequence of Human Notch 3 (NP_000426)

```
   1  MGPGARGRRR RRRPMSPPPP PPPVRALPLL LLLAGPGAAA PPCLDGSPCA NGGRCTQLPS
  61  REAACLCPPG WVGERCQLED PCHSGPCAGR GVCQSSVVAG TARFSCRCPR GFRGPDCSLP
 121  DPCLSSPCAH GARCSVGPDG RFLCSCPPGY QGRSCRSDVD ECRVGEPCRH GGTCLNTPGS
 181  FRCQCPAGYT GPLCENPAVP CAPSPCRNGG TCRQSGDLTY DCACLPGFEG QNCEVNVDDC
 241  PGHRCLNGGT CVDGVNTYNC QCPPEWTGQF CTEDVDECQL QPNACHNGGT CFNTLGGHSC
 301  VCVNGWTGES CSQNIDDCAT AVCFHGATCH DRVASFYCAC PMGKTGLLCH LDDACVSNPC
 361  HEDAICDTNP VNGRAICTCP PGFTGGACDQ DVDECSIGAN PCEHLGRCVN TQGSFLCQCG
 421  RGYTGPRCET DVNECLSGPC RNQATCLDRI GQFTCICMAG FTGTYCEVDI DECQSSPCVN
 481  GGVCKDRVNG FSCTCPSGFS GSTCQLDVDE CASTPCRNGA KCVDQPDGYE CRCAEGFEGT
 541  LCDRNVDDCS PDPCHHGRCV DGIASFSCAC APGYTGTRCE SQVDECRSQP CRHGGKCLDL
 601  VDKYLCRCPS GTTGVNCEVN IDDCASNPCT FGVCRDGINR YDCVCQPGFT GPLCNVEINE
 661  CASSPCGEGG SCVDGENGFR CLCPPGSLPP LCLPPSHPCA HEPCSHGICY DAPGGFRCVC
 721  EPGWSGPRCS QSLARDACES QPCRAGGTCS SDGMGFHCTC PPGVQGRQCE LLSPCTPNPC
 781  EHGGRCESAP GQLPVCSCPQ GWQGPRCQQD VDECAGPAPC GPHGICTNLA GSFSCTCHGG
 841  YTGPSCDQDI NDCDPNPCLN GGSCQDGVGS FSCSCLPGFA GPRCARDVDE CLSNPCGPGT
 901  CTDHVASFTC TCPPGYGGFH CEQDLPDCSP SSCFNGGTCV DGVNSFSCLC RPGYTGAHCQ
 961  HEADPCLSRP CLHGGVCSAA HPGFRCTCLE SFTGPQCQTL VDWCSRQPCQ NGGRCVQTGA
1021  YCLCPPGWSG RLCDIRSLPC REAAAQIGVR LEQLCQAGGQ CVDEDSSHYC VCPEGRTGSH
1081  CEQEVDPCLA QPCQHGGTCR GYMGGYMCEC LPGYNGDNCE DDVDECASQP CQHGGSCIDL
1141  VARYLCSCPP GTLGVLCEIN EDDCGPGPPL DSGPRCLHNG TCVDLVGGFR CTCPPGYTGL
1201  RCEADINECR SGACHAAHTR DCLQDPGGGF RCLCHAGFSG PRCQTVLSPC ESQPCQHGGQ
1261  CRPSPGPGGG LTFTCHCAQP FWGPRCERVA RSCRELQCPV GVPCQQTPRG PRCACPPGLS
1321  GPSCRSFPGS PPGASNASCA AAPCLHGGSC RPAPLAPFFR CACAQGWTGP RCEAPAAAPE
1381  VSE*EPRCPRA ACQAKRGDQR CDRECNSPGC GWDGGDCSLS VGDPWRQCEA LQCWRLFNNS*
1441  *RCDPACSSPA CLYDNFDCHA GGRERTCNPV YEKYCADHFA DGRCDQGCNT EECGWDGLDC*
1501  *ASE*VPALLAR GVLVLTVLLP PEELLRSSAD FLQRLSAILR TSLRFRLDAH GQAMVFPYHR
1561  PSPGSEPRAR RELAPEVIGS VVMLEIDNRL CLQSPENDHC FPDAQSAADY LGALSAVERL
1621  DFPYPLRDVR GEPLEPPEPS VPLLPLLVAG AVLLLVILVL GVMVARRKRE HSTLWFPEGF
1681  SLHKDVASGH KGRREPVGQD ALGMKNMAKG ESLMGEVATD WMDTECPEAK RLKVEEPGMG
1741  AEEAVDCRQW TQHHLVAADI RVAPAMALTP PQGDADADGM DVNVRGPDGF TPLMLASFCG
1801  GALEPMPTEE DEADDTSASI ISDLICQGAQ LGARTDRTGE TALHLAARYA RADAAKRLLD
1861  AGADTNAQDH SGRTPLHTAV TADAQGVFQI LIRNRSTDLD ARMADGSTAL ILAARLAVEG
1921  MVEELIASHA DVNAVDELGK SALHWAAAVN NVEATLALLK NGANKDMQDS KEETPLFLAA
1981  REGSYEAAKL LLDHFANREI TDHLDRLPRD VAQERLHQDI VRLLDQPSGP RSPPGPHGLG
2041  PLLCPPGAFL PGLKAAQSGS KKSRRPPGKA GLGPQGPRGR GKKLTLACPG PLADSSVTLS
2101  PVDSLDSPRP FGGPPASPGG FPLEGPYAAA TATAVSLAQL GGPGRAGLGR QPPGGCVLSL
2161  GLLNPVAVPL DWARLPPPAP PGPSFLLPLA PGPQLLNPGT PVSPQERPPP YLAVPGHGEE
2221  YPVAGAHSSP PKARFLRVPS EHPYLTPSPE SPEHWASPSP PSLSDWSEST PSPATATGAM
2281  ATTTGALPAQ PLPLSVPSSL AQAQTQLGPQ PEVTPKRQVL A (SEQ ID NO 3)
```

*FIG. 2*

SEQUENCE LISTING

```
<160> NUMBER OF SEQ ID NOS: 4

<210> SEQ ID NO 1
<211> LENGTH: 2555
<212> TYPE: PRT
<213> ORGANISM: Homo sapiens

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
```

```
                290                 295                 300
Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Cys Phe His Gly Ala Thr Cys His Asp
                340                 345                 350

Arg Val Ala Ser Phe Tyr Cys Glu Cys Pro His Gly Arg Thr Gly Leu
                355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
                420                 425                 430

Leu Gly Ser Phe Glu Cys Gln Cys Leu Gln Gly Tyr Thr Gly Pro Arg
                435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
                500                 505                 510

Gln Cys Glu Cys Pro Thr Gly Phe Thr Gly His Leu Cys Gln Tyr Asp
                515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
                580                 585                 590

Pro Gly Tyr Thr Gly His His Cys Glu Thr Asn Ile Asn Glu Cys Ser
                595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
                675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720
```

```
Asn Ser Asn Pro Cys Val His Gly Ala Cys Arg Asp Ser Leu Asn Gly
            725                 730                 735

Tyr Lys Cys Asp Cys Asp Pro Gly Trp Ser Gly Thr Asn Cys Asp Ile
        740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
            805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
        850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
            885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Arg Gly Thr Phe Cys Glu Glu
            930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
            965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
            995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125
```

-continued

His His Cys Arg Cys Gln Ala Gly Tyr Thr Gly Ser Tyr Cys Glu
1130                1135                1140

Asp Leu Val Asp Glu Cys Ser Pro Ser Pro Cys Gln Asn Gly Ala
1145                1150                1155

Thr Cys Thr Asp Tyr Leu Gly Gly Tyr Ser Cys Lys Cys Val Ala
1160                1165                1170

Gly Tyr His Gly Val Asn Cys Ser Glu Glu Ile Asp Glu Cys Leu
1175                1180                1185

Ser His Pro Cys Gln Asn Gly Gly Thr Cys Leu Asp Leu Pro Asn
1190                1195                1200

Thr Tyr Lys Cys Ser Cys Pro Arg Gly Thr Gln Gly Val His Cys
1205                1210                1215

Glu Ile Asn Val Asp Asp Cys Asn Pro Pro Val Asp Pro Val Ser
1220                1225                1230

Arg Ser Pro Lys Cys Phe Asn Asn Gly Thr Cys Val Asp Gln Val
1235                1240                1245

Gly Gly Tyr Ser Cys Thr Cys Pro Pro Gly Phe Val Gly Glu Arg
1250                1255                1260

Cys Glu Gly Asp Val Asn Glu Cys Leu Ser Asn Pro Cys Asp Ala
1265                1270                1275

Arg Gly Thr Gln Asn Cys Val Gln Arg Val Asn Asp Phe His Cys
1280                1285                1290

Glu Cys Arg Ala Gly His Thr Gly Arg Arg Cys Glu Ser Val Ile
1295                1300                1305

Asn Gly Cys Lys Gly Lys Pro Cys Lys Asn Gly Gly Thr Cys Ala
1310                1315                1320

Val Ala Ser Asn Thr Ala Arg Gly Phe Ile Cys Lys Cys Pro Ala
1325                1330                1335

Gly Phe Glu Gly Ala Thr Cys Glu Asn Asp Ala Arg Thr Cys Gly
1340                1345                1350

Ser Leu Arg Cys Leu Asn Gly Gly Thr Cys Ile Ser Gly Pro Arg
1355                1360                1365

Ser Pro Thr Cys Leu Cys Leu Gly Pro Phe Thr Gly Pro Glu Cys
1370                1375                1380

Gln Phe Pro Ala Ser Ser Pro Cys Leu Gly Gly Asn Pro Cys Tyr
1385                1390                1395

Asn Gln Gly Thr Cys Glu Pro Thr Ser Glu Ser Pro Phe Tyr Arg
1400                1405                1410

Cys Leu Cys Pro Ala Lys Phe Asn Gly Leu Leu Cys His Ile Leu
1415                1420                1425

Asp Tyr Ser Phe Gly Gly Gly Ala Gly Arg Asp Ile Pro Pro Pro
1430                1435                1440

Leu Ile Glu Glu Ala Cys Glu Leu Pro Glu Cys Gln Glu Asp Ala
1445                1450                1455

Gly Asn Lys Val Cys Ser Leu Gln Cys Asn Asn His Ala Cys Gly
1460                1465                1470

Trp Asp Gly Gly Asp Cys Ser Leu Asn Phe Asn Asp Pro Trp Lys
1475                1480                1485

Asn Cys Thr Gln Ser Leu Gln Cys Trp Lys Tyr Phe Ser Asp Gly
1490                1495                1500

His Cys Asp Ser Gln Cys Asn Ser Ala Gly Cys Leu Phe Asp Gly
1505                1510                1515

Phe Asp Cys Gln Arg Ala Glu Gly Gln Cys Asn Pro Leu Tyr Asp

-continued

```
            1520                1525                1530
Gln Tyr Cys Lys Asp His Phe Ser Asp Gly His Cys Asp Gln Gly
            1535                1540                1545
Cys Asn Ser Ala Glu Cys Glu Trp Asp Gly Leu Asp Cys Ala Glu
            1550                1555                1560
His Val Pro Glu Arg Leu Ala Ala Gly Thr Leu Val Val Val Val
            1565                1570                1575
Leu Met Pro Pro Glu Gln Leu Arg Asn Ser Ser Phe His Phe Leu
            1580                1585                1590
Arg Glu Leu Ser Arg Val Leu His Thr Asn Val Val Phe Lys Arg
            1595                1600                1605
Asp Ala His Gly Gln Gln Met Ile Phe Pro Tyr Tyr Gly Arg Glu
            1610                1615                1620
Glu Glu Leu Arg Lys His Pro Ile Lys Arg Ala Ala Glu Gly Trp
            1625                1630                1635
Ala Ala Pro Asp Ala Leu Leu Gly Gln Val Lys Ala Ser Leu Leu
            1640                1645                1650
Pro Gly Gly Ser Glu Gly Gly Arg Arg Arg Glu Leu Asp Pro
            1655                1660                1665
Met Asp Val Arg Gly Ser Ile Val Tyr Leu Glu Ile Asp Asn Arg
            1670                1675                1680
Gln Cys Val Gln Ala Ser Ser Gln Cys Phe Gln Ser Ala Thr Asp
            1685                1690                1695
Val Ala Ala Phe Leu Gly Ala Leu Ala Ser Leu Gly Ser Leu Asn
            1700                1705                1710
Ile Pro Tyr Lys Ile Glu Ala Val Gln Ser Glu Thr Val Glu Pro
            1715                1720                1725
Pro Pro Pro Ala Gln Leu His Phe Met Tyr Val Ala Ala Ala Ala
            1730                1735                1740
Phe Val Leu Leu Phe Phe Val Gly Cys Gly Val Leu Leu Ser Arg
            1745                1750                1755
Lys Arg Arg Arg Gln His Gly Gln Leu Trp Phe Pro Glu Gly Phe
            1760                1765                1770
Lys Val Ser Glu Ala Ser Lys Lys Arg Arg Glu Pro Leu Gly
            1775                1780                1785
Glu Asp Ser Val Gly Leu Lys Pro Leu Lys Asn Ala Ser Asp Gly
            1790                1795                1800
Ala Leu Met Asp Asp Asn Gln Asn Glu Trp Gly Asp Glu Asp Leu
            1805                1810                1815
Glu Thr Lys Lys Phe Arg Phe Glu Glu Pro Val Val Leu Pro Asp
            1820                1825                1830
Leu Asp Asp Gln Thr Asp His Arg Gln Trp Thr Gln Gln His Leu
            1835                1840                1845
Asp Ala Ala Asp Leu Arg Met Ser Ala Met Ala Pro Thr Pro Pro
            1850                1855                1860
Gln Gly Glu Val Asp Ala Asp Cys Met Asp Val Asn Val Arg Gly
            1865                1870                1875
Pro Asp Gly Phe Thr Pro Leu Met Ile Ala Ser Cys Ser Gly Gly
            1880                1885                1890
Gly Leu Glu Thr Gly Asn Ser Glu Glu Glu Glu Asp Ala Pro Ala
            1895                1900                1905
Val Ile Ser Asp Phe Ile Tyr Gln Gly Ala Ser Leu His Asn Gln
            1910                1915                1920
```

-continued

```
Thr Asp Arg Thr Gly Glu Thr Ala Leu His Leu Ala Ala Arg Tyr
1925                1930                1935

Ser Arg Ser Asp Ala Ala Lys Arg Leu Leu Glu Ala Ser Ala Asp
1940                1945                1950

Ala Asn Ile Gln Asp Asn Met Gly Arg Thr Pro Leu His Ala Ala
1955                1960                1965

Val Ser Ala Asp Ala Gln Gly Val Phe Gln Ile Leu Ile Arg Asn
1970                1975                1980

Arg Ala Thr Asp Leu Asp Ala Arg Met His Asp Gly Thr Thr Pro
1985                1990                1995

Leu Ile Leu Ala Ala Arg Leu Ala Val Glu Gly Met Leu Glu Asp
2000                2005                2010

Leu Ile Asn Ser His Ala Asp Val Asn Ala Val Asp Asp Leu Gly
2015                2020                2025

Lys Ser Ala Leu His Trp Ala Ala Ala Val Asn Asn Val Asp Ala
2030                2035                2040

Ala Val Val Leu Leu Lys Asn Gly Ala Asn Lys Asp Met Gln Asn
2045                2050                2055

Asn Arg Glu Glu Thr Pro Leu Phe Leu Ala Ala Arg Glu Gly Ser
2060                2065                2070

Tyr Glu Thr Ala Lys Val Leu Leu Asp His Phe Ala Asn Arg Asp
2075                2080                2085

Ile Thr Asp His Met Asp Arg Leu Pro Arg Asp Ile Ala Gln Glu
2090                2095                2100

Arg Met His His Asp Ile Val Arg Leu Leu Asp Glu Tyr Asn Leu
2105                2110                2115

Val Arg Ser Pro Gln Leu His Gly Ala Pro Leu Gly Gly Thr Pro
2120                2125                2130

Thr Leu Ser Pro Pro Leu Cys Ser Pro Asn Gly Tyr Leu Gly Ser
2135                2140                2145

Leu Lys Pro Gly Val Gln Gly Lys Lys Val Arg Lys Pro Ser Ser
2150                2155                2160

Lys Gly Leu Ala Cys Gly Ser Lys Glu Ala Lys Asp Leu Lys Ala
2165                2170                2175

Arg Arg Lys Lys Ser Gln Asp Gly Lys Gly Cys Leu Leu Asp Ser
2180                2185                2190

Ser Gly Met Leu Ser Pro Val Asp Ser Leu Glu Ser Pro His Gly
2195                2200                2205

Tyr Leu Ser Asp Val Ala Ser Pro Pro Leu Leu Pro Ser Pro Phe
2210                2215                2220

Gln Gln Ser Pro Ser Val Pro Leu Asn His Leu Pro Gly Met Pro
2225                2230                2235

Asp Thr His Leu Gly Ile Gly His Leu Asn Val Ala Ala Lys Pro
2240                2245                2250

Glu Met Ala Ala Leu Gly Gly Gly Gly Arg Leu Ala Phe Glu Thr
2255                2260                2265

Gly Pro Pro Arg Leu Ser His Leu Pro Val Ala Ser Gly Thr Ser
2270                2275                2280

Thr Val Leu Gly Ser Ser Ser Gly Gly Ala Leu Asn Phe Thr Val
2285                2290                2295

Gly Gly Ser Thr Ser Leu Asn Gly Gln Cys Glu Trp Leu Ser Arg
2300                2305                2310
```

```
Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 2
<211> LENGTH: 2531
<212> TYPE: PRT
<213> ORGANISM: Mus musculus

<400> SEQUENCE: 2

Met Pro Arg Leu Leu Thr Pro Leu Leu Cys Leu Thr Leu Leu Pro Ala
1               5                   10                  15

Leu Ala Ala Arg Gly Leu Arg Cys Ser Gln Pro Ser Gly Thr Cys Leu
                20                  25                  30

Asn Gly Gly Arg Cys Glu Val Ala Asn Gly Thr Glu Ala Cys Val Cys
            35                  40                  45

Ser Gly Ala Phe Val Gly Gln Arg Cys Gln Asp Ser Asn Pro Cys Leu
        50                  55                  60

Ser Thr Pro Cys Lys Asn Ala Gly Thr Cys His Val Val Asp His Gly
65                  70                  75                  80

Gly Thr Val Asp Tyr Ala Cys Ser Cys Pro Leu Gly Phe Ser Gly Pro
                85                  90                  95

Leu Cys Leu Thr Pro Leu Asp Asn Ala Cys Leu Ala Asn Pro Cys Arg
            100                 105                 110
```

-continued

```
Asn Gly Gly Thr Cys Asp Leu Leu Thr Leu Thr Glu Tyr Lys Cys Arg
    115                 120                 125
Cys Pro Pro Gly Trp Ser Gly Lys Ser Cys Gln Gln Ala Asp Pro Cys
    130                 135                 140
Ala Ser Asn Pro Cys Ala Asn Gly Gly Gln Cys Leu Pro Phe Glu Ser
145                 150                 155                 160
Ser Tyr Ile Cys Arg Cys Pro Pro Gly Phe His Gly Pro Thr Cys Arg
                165                 170                 175
Gln Asp Val Asn Glu Cys Ser Gln Asn Pro Gly Leu Cys Arg His Gly
            180                 185                 190
Gly Thr Cys His Asn Glu Ile Gly Ser Tyr Arg Cys Ala Cys Arg Ala
        195                 200                 205
Thr His Thr Gly Pro His Cys Glu Leu Pro Tyr Val Pro Cys Ser Pro
    210                 215                 220
Ser Pro Cys Gln Asn Gly Gly Thr Cys Arg Pro Thr Gly Asp Thr Thr
225                 230                 235                 240
His Glu Cys Ala Cys Leu Pro Gly Phe Ala Gly Gln Asn Cys Glu Glu
                245                 250                 255
Asn Val Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe Gln Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ala Leu Gly Ala Asn Pro Cys Glu His Ala Gly Lys Cys Leu Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Ile Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val Tyr Cys Glu Ile Asn Thr Asp Glu Cys Ala Ser
                485                 490                 495
Ser Pro Cys Leu His Asn Gly His Cys Met Asp Lys Ile Asn Glu Phe
            500                 505                 510
Gln Cys Gln Cys Pro Lys Gly Phe Asn Gly His Leu Cys Gln Tyr Asp
        515                 520                 525
```

-continued

```
Val Asp Glu Cys Ala Ser Thr Pro Cys Lys Asn Gly Ala Lys Cys Leu
530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
        595                 600                 605

Ser Gln Pro Cys Arg His Gly Thr Cys Gln Asp Arg Asp Asn Ser
610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
        675                 680                 685

Asn Gly Gly Thr Cys Glu Asp Gly Ile Ala Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
            820                 825                 830

Cys Ala Thr Ser Pro Cys Lys Asn Ser Gly Val Cys Lys Glu Ser Glu
        835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                885                 890                 895

Ala Gly Tyr Thr Gly Arg Asn Cys Glu Ser Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Gln Gly Ala Phe Cys Glu Glu
930                 935                 940

Asp Ile Asn Glu Cys Ala Ser Asn Pro Cys Gln Asn Gly Ala Asn Cys
```

```
                                    -continued
945               950               955               960
Thr Asp Cys Val Asp Ser Tyr Thr Cys Thr Cys Pro Val Gly Phe Asn
                965               970               975
Gly Ile His Cys Glu Asn Asn Thr Pro Asp Cys Thr Glu Ser Ser Cys
                980               985               990
Phe Asn Gly Gly Thr Cys Val Asp Gly Ile Asn Ser Phe Thr Cys Leu
                995              1000              1005
Cys Pro Pro Gly Phe Thr Gly Ser Tyr Cys Gln Tyr Asp Val Asn
            1010              1015              1020
Glu Cys Asp Ser Arg Pro Cys Leu His Gly Gly Thr Cys Gln Asp
            1025              1030              1035
Ser Tyr Gly Thr Tyr Lys Cys Thr Cys Pro Gln Gly Tyr Thr Gly
            1040              1045              1050
Leu Asn Cys Gln Asn Leu Val Arg Trp Cys Asp Ser Ala Pro Cys
            1055              1060              1065
Lys Asn Gly Gly Arg Cys Trp Gln Thr Asn Thr Gln Tyr His Cys
            1070              1075              1080
Glu Cys Arg Ser Gly Trp Thr Gly Val Asn Cys Asp Val Leu Ser
            1085              1090              1095
Val Ser Cys Glu Val Ala Ala Gln Lys Arg Gly Ile Asp Val Thr
            1100              1105              1110
Leu Leu Cys Gln His Gly Gly Leu Cys Val Asp Glu Gly Asp Lys
            1115              1120              1125
His Tyr Cys His Cys Gln Ala Gly Tyr Thr Gly Ser Tyr Cys Glu
            1130              1135              1140
Asp Glu Val Asp Glu Cys Ser Pro Asn Pro Cys Gln Asn Gly Ala
            1145              1150              1155
Thr Cys Thr Asp Tyr Leu Gly Gly Phe Ser Cys Lys Cys Val Ala
            1160              1165              1170
Gly Tyr His Gly Ser Asn Cys Ser Glu Glu Ile Asn Glu Cys Leu
            1175              1180              1185
Ser Gln Pro Cys Gln Asn Gly Gly Thr Cys Ile Asp Leu Thr Asn
            1190              1195              1200
Ser Tyr Lys Cys Ser Cys Pro Arg Gly Thr Gln Gly Val His Cys
            1205              1210              1215
Glu Ile Asn Val Asp Asp Cys His Pro Pro Leu Asp Pro Ala Ser
            1220              1225              1230
Arg Ser Pro Lys Cys Phe Asn Asn Gly Thr Cys Val Asp Gln Val
            1235              1240              1245
Gly Gly Tyr Thr Cys Thr Cys Pro Pro Gly Phe Val Gly Glu Arg
            1250              1255              1260
Cys Glu Gly Asp Val Asn Glu Cys Leu Ser Asn Pro Cys Asp Pro
            1265              1270              1275
Arg Gly Thr Gln Asn Cys Val Gln Arg Val Asn Asp Phe His Cys
            1280              1285              1290
Glu Cys Arg Ala Gly His Thr Gly Arg Arg Cys Glu Ser Val Ile
            1295              1300              1305
Asn Gly Cys Arg Gly Lys Pro Cys Lys Asn Gly Gly Val Cys Ala
            1310              1315              1320
Val Ala Ser Asn Thr Ala Arg Gly Phe Ile Cys Arg Cys Pro Ala
            1325              1330              1335
Gly Phe Glu Gly Ala Thr Cys Glu Asn Asp Ala Arg Thr Cys Gly
            1340              1345              1350
```

```
Ser Leu Arg Cys Leu Asn Gly Gly Thr Cys Ile Ser Gly Pro Arg
    1355                1360                1365

Ser Pro Thr Cys Leu Cys Leu Gly Ser Phe Thr Gly Pro Glu Cys
    1370                1375                1380

Gln Phe Pro Ala Ser Ser Pro Cys Val Gly Ser Asn Pro Cys Tyr
    1385                1390                1395

Asn Gln Gly Thr Cys Glu Pro Thr Ser Glu Asn Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Thr Gly Gly Ala Gly Arg Asp Ile Pro Pro Pro
    1430                1435                1440

Gln Ile Glu Glu Ala Cys Glu Leu Pro Glu Cys Gln Val Asp Ala
    1445                1450                1455

Gly Asn Lys Val Cys Asn Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Leu Thr Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Leu Val Val
    1565                1570                1575

Leu Leu Pro Pro Asp Gln Leu Arg Asn Asn Ser Phe His Phe Leu
    1580                1585                1590

Arg Glu Leu Ser His Val Leu His Thr Asn Val Val Phe Lys Arg
    1595                1600                1605

Asp Ala Gln Gly Gln Gln Met Ile Phe Pro Tyr Tyr Gly His Glu
    1610                1615                1620

Glu Glu Leu Arg Lys His Pro Ile Lys Arg Ser Thr Val Gly Trp
    1625                1630                1635

Ala Thr Ser Ser Leu Leu Pro Gly Thr Ser Gly Gly Arg Gln Arg
    1640                1645                1650

Arg Glu Leu Asp Pro Met Asp Ile Arg Gly Ser Ile Val Tyr Leu
    1655                1660                1665

Glu Ile Asp Asn Arg Gln Cys Val Gln Ser Ser Gln Cys Phe
    1670                1675                1680

Gln Ser Ala Thr Asp Val Ala Ala Phe Leu Gly Ala Leu Ala Ser
    1685                1690                1695

Leu Gly Ser Leu Asn Ile Pro Tyr Lys Ile Glu Ala Val Lys Ser
    1700                1705                1710

Glu Pro Val Glu Pro Pro Leu Pro Ser Gln Leu His Leu Met Tyr
    1715                1720                1725

Val Ala Ala Ala Ala Phe Val Leu Leu Phe Phe Val Gly Cys Gly
    1730                1735                1740
```

-continued

```
Val Leu Leu Ser Arg Lys Arg Arg Gln His Gly Gln Leu Trp
1745                1750                1755

Phe Pro Glu Gly Phe Lys Val Ser Glu Ala Ser Lys Lys Arg
1760                1765                1770

Arg Glu Pro Leu Gly Glu Asp Ser Val Gly Leu Lys Pro Leu Lys
1775                1780                1785

Asn Ala Ser Asp Gly Ala Leu Met Asp Asn Gln Asn Glu Trp
1790                1795                1800

Gly Asp Glu Asp Leu Glu Thr Lys Lys Phe Arg Phe Glu Glu Pro
1805                1810                1815

Val Val Leu Pro Asp Leu Ser Asp Gln Thr Asp His Arg Gln Trp
1820                1825                1830

Thr Gln Gln His Leu Asp Ala Ala Asp Leu Arg Met Ser Ala Met
1835                1840                1845

Ala Pro Thr Pro Pro Gln Gly Glu Val Asp Ala Asp Cys Met Asp
1850                1855                1860

Val Asn Val Arg Gly Pro Asp Gly Phe Thr Pro Leu Met Ile Ala
1865                1870                1875

Ser Cys Ser Gly Gly Leu Glu Thr Gly Asn Ser Glu Glu Glu
1880                1885                1890

Glu Asp Ala Pro Ala Val Ile Ser Asp Phe Ile Tyr Gln Gly Ala
1895                1900                1905

Ser Leu His Asn Gln Thr Asp Arg Thr Gly Glu Thr Ala Leu His
1910                1915                1920

Leu Ala Ala Arg Tyr Ser Arg Ser Asp Ala Ala Lys Arg Leu Leu
1925                1930                1935

Glu Ala Ser Ala Asp Ala Asn Ile Gln Asp Asn Met Gly Arg Thr
1940                1945                1950

Pro Leu His Ala Ala Val Ser Ala Asp Ala Gln Gly Val Phe Gln
1955                1960                1965

Ile Leu Leu Arg Asn Arg Ala Thr Asp Leu Asp Ala Arg Met His
1970                1975                1980

Asp Gly Thr Thr Pro Leu Ile Leu Ala Ala Arg Leu Ala Val Glu
1985                1990                1995

Gly Met Leu Glu Asp Leu Ile Asn Ser His Ala Asp Val Asn Ala
2000                2005                2010

Val Asp Asp Leu Gly Lys Ser Ala Leu His Trp Ala Ala Ala Val
2015                2020                2025

Asn Asn Val Asp Ala Ala Val Val Leu Leu Lys Asn Gly Ala Asn
2030                2035                2040

Lys Asp Met Gln Asn Asn Lys Glu Glu Thr Pro Leu Phe Leu Ala
2045                2050                2055

Ala Arg Glu Gly Ser Tyr Glu Thr Ala Lys Val Leu Leu Asp His
2060                2065                2070

Phe Ala Asn Arg Asp Ile Thr Asp His Met Asp Arg Leu Pro Arg
2075                2080                2085

Asp Ile Ala Gln Glu Arg Met His His Asp Ile Val Arg Leu Leu
2090                2095                2100

Asp Glu Tyr Asn Leu Val Arg Ser Pro Gln Leu His Gly Thr Ala
2105                2110                2115

Leu Gly Gly Thr Pro Thr Leu Ser Pro Thr Leu Cys Ser Pro Asn
2120                2125                2130

Gly Tyr Leu Gly Asn Leu Lys Ser Ala Thr Gln Gly Lys Lys Ala
```

-continued

```
            2135                2140                2145
Arg Lys Pro Ser Thr Lys Gly Leu Ala Cys Gly Ser Lys Glu Ala
        2150                2155                2160
Lys Asp Leu Lys Ala Arg Arg Lys Lys Ser Gln Asp Gly Lys Gly
        2165                2170                2175
Cys Leu Leu Asp Ser Ser Ser Met Leu Ser Pro Val Asp Ser Leu
        2180                2185                2190
Glu Ser Pro His Gly Tyr Leu Ser Asp Val Ala Ser Pro Pro Leu
        2195                2200                2205
Leu Pro Ser Pro Phe Gln Gln Ser Pro Ser Met Pro Leu Ser His
        2210                2215                2220
Leu Pro Gly Met Pro Asp Thr His Leu Gly Ile Ser His Leu Asn
        2225                2230                2235
Val Ala Ala Lys Pro Glu Met Ala Ala Leu Ala Gly Gly Ser Arg
        2240                2245                2250
Leu Ala Phe Glu Pro Pro Pro Pro Arg Leu Ser His Leu Pro Val
        2255                2260                2265
Ala Ser Ser Ala Ser Thr Val Leu Ser Thr Asn Gly Thr Gly Ala
        2270                2275                2280
Met Asn Phe Thr Val Gly Ala Pro Ala Ser Leu Asn Gly Gln Cys
        2285                2290                2295
Glu Trp Leu Pro Arg Leu Gln Asn Gly Met Val Pro Ser Gln Tyr
        2300                2305                2310
Asn Pro Leu Arg Pro Gly Val Thr Pro Gly Thr Leu Ser Thr Gln
        2315                2320                2325
Ala Ala Gly Leu Gln His Ser Met Met Gly Pro Leu His Ser Ser
        2330                2335                2340
Leu Ser Thr Asn Thr Leu Ser Pro Ile Ile Tyr Gln Gly Leu Pro
        2345                2350                2355
Asn Thr Arg Leu Ala Thr Gln Pro His Leu Val Gln Thr Gln Gln
        2360                2365                2370
Val Gln Pro Gln Asn Leu Gln Leu Gln Pro Gln Asn Leu Gln Pro
        2375                2380                2385
Pro Ser Gln Pro His Leu Ser Val Ser Ser Ala Ala Asn Gly His
        2390                2395                2400
Leu Gly Arg Ser Phe Leu Ser Gly Glu Pro Ser Gln Ala Asp Val
        2405                2410                2415
Gln Pro Leu Gly Pro Ser Ser Leu Pro Val His Thr Ile Leu Pro
        2420                2425                2430
Gln Glu Ser Gln Ala Leu Pro Thr Ser Leu Pro Ser Ser Met Val
        2435                2440                2445
Pro Pro Met Thr Thr Thr Gln Phe Leu Thr Pro Pro Ser Gln His
        2450                2455                2460
Ser Tyr Ser Ser Ser Pro Val Asp Asn Thr Pro Ser His Gln Leu
        2465                2470                2475
Gln Val Pro Glu His Pro Phe Leu Thr Pro Ser Pro Glu Ser Pro
        2480                2485                2490
Asp Gln Trp Ser Ser Ser Pro His Ser Asn Ile Ser Asp Trp
        2495                2500                2505
Ser Glu Gly Ile Ser Ser Pro Pro Thr Thr Met Pro Ser Gln Ile
        2510                2515                2520
Thr His Ile Pro Glu Ala Phe Lys
        2525                2530
```

<210> SEQ ID NO 3
<211> LENGTH: 2321
<212> TYPE: PRT
<213> ORGANISM: Homo sapiens

<400> SEQUENCE: 3

```
Met Gly Pro Gly Ala Gly Arg Arg Arg Arg Pro Met Ser
1               5                   10              15

Pro Pro Pro Pro Pro Pro Val Arg Ala Leu Pro Leu Leu Leu
                20                  25                  30

Leu Ala Gly Pro Gly Ala Ala Pro Pro Cys Leu Asp Gly Ser Pro
            35                  40                  45

Cys Ala Asn Gly Gly Arg Cys Thr Gln Leu Pro Ser Arg Glu Ala Ala
        50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Pro Gly Phe Thr
```

```
              370                 375                 380
Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Pro Arg Cys Glu Thr Asp Val
            420                 425                 430

Asn Glu Cys Leu Ser Gly Pro Cys Arg Asn Gln Ala Thr Cys Leu Asp
                435                 440                 445

Arg Ile Gly Gln Phe Thr Cys Ile Cys Met Ala Gly Phe Thr Gly Thr
            450                 455                 460

Tyr Cys Glu Val Asp Ile Asp Glu Cys Gln Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
                500                 505                 510

Ser Thr Pro Cys Arg Asn Gly Ala Lys Cys Val Asp Gln Pro Asp Gly
                515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
                660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
                740                 745                 750

Gly Met Gly Phe His Cys Thr Cys Pro Pro Gly Val Gln Gly Arg Gln
                755                 760                 765

Cys Glu Leu Leu Ser Pro Cys Thr Pro Asn Pro Cys Glu His Gly Gly
            770                 775                 780

Arg Cys Glu Ser Ala Pro Gly Gln Leu Pro Val Cys Ser Cys Pro Gln
785                 790                 795                 800
```

-continued

```
Gly Trp Gln Gly Pro Arg Cys Gln Gln Asp Val Asp Glu Cys Ala Gly
            805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
            885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
            965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
            995                 1000                1005

Cys Gln Asn Gly Gly Arg Cys Val Gln Thr Gly Ala Tyr Cys Leu
    1010                1015                1020

Cys Pro Pro Gly Trp Ser Gly Arg Leu Cys Asp Ile Arg Ser Leu
    1025                1030                1035

Pro Cys Arg Glu Ala Ala Ala Gln Ile Gly Val Arg Leu Glu Gln
    1040                1045                1050

Leu Cys Gln Ala Gly Gly Gln Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Asp Val Asp Glu Cys Ala Ser
    1115                1120                1125

Gln Pro Cys Gln His Gly Gly Ser Cys Ile Asp Leu Val Ala Arg
    1130                1135                1140

Tyr Leu Cys Ser Cys Pro Pro Gly Thr Leu Gly Val Leu Cys Glu
    1145                1150                1155

Ile Asn Glu Asp Asp Cys Gly Pro Gly Pro Pro Leu Asp Ser Gly
    1160                1165                1170

Pro Arg Cys Leu His Asn Gly Thr Cys Val Asp Leu Val Gly Gly
    1175                1180                1185

Phe Arg Cys Thr Cys Pro Pro Gly Tyr Thr Gly Leu Arg Cys Glu
    1190                1195                1200
```

```
Ala Asp Ile Asn Glu Cys Arg Ser Gly Ala Cys His Ala Ala His
1205                 1210                1215

Thr Arg Asp Cys Leu Gln Asp Pro Gly Gly Phe Arg Cys Leu
1220                 1225                1230

Cys His Ala Gly Phe Ser Gly Pro Arg Cys Gln Thr Val Leu Ser
1235                 1240                1245

Pro Cys Glu Ser Gln Pro Cys Gln His Gly Gly Gln Cys Arg Pro
1250                 1255                1260

Ser Pro Gly Pro Gly Gly Leu Thr Phe Thr Cys His Cys Ala
1265                 1270                1275

Gln Pro Phe Trp Gly Pro Arg Cys Glu Arg Val Ala Arg Ser Cys
1280                 1285                1290

Arg Glu Leu Gln Cys Pro Val Gly Val Pro Cys Gln Gln Thr Pro
1295                 1300                1305

Arg Gly Pro Arg Cys Ala Cys Pro Pro Gly Leu Ser Gly Pro Ser
1310                 1315                1320

Cys Arg Ser Phe Pro Gly Ser Pro Pro Gly Ala Ser Asn Ala Ser
1325                 1330                1335

Cys Ala Ala Ala Pro Cys Leu His Gly Gly Ser Cys Arg Pro Ala
1340                 1345                1350

Pro Leu Ala Pro Phe Phe Arg Cys Ala Cys Ala Gln Gly Trp Thr
1355                 1360                1365

Gly Pro Arg Cys Glu Ala Pro Ala Ala Ala Pro Glu Val Ser Glu
1370                 1375                1380

Glu Pro Arg Cys Pro Arg Ala Ala Cys Gln Ala Lys Arg Gly Asp
1385                 1390                1395

Gln Arg Cys Asp Arg Glu Cys Asn Ser Pro Gly Cys Gly Trp Asp
1400                 1405                1410

Gly Gly Asp Cys Ser Leu Ser Val Gly Asp Pro Trp Arg Gln Cys
1415                 1420                1425

Glu Ala Leu Gln Cys Trp Arg Leu Phe Asn Asn Ser Arg Cys Asp
1430                 1435                1440

Pro Ala Cys Ser Ser Pro Ala Cys Leu Tyr Asp Asn Phe Asp Cys
1445                 1450                1455

His Ala Gly Gly Arg Glu Arg Thr Cys Asn Pro Val Tyr Glu Lys
1460                 1465                1470

Tyr Cys Ala Asp His Phe Ala Asp Gly Arg Cys Asp Gln Gly Cys
1475                 1480                1485

Asn Thr Glu Glu Cys Gly Trp Asp Gly Leu Asp Cys Ala Ser Glu
1490                 1495                1500

Val Pro Ala Leu Leu Ala Arg Gly Val Leu Val Leu Thr Val Leu
1505                 1510                1515

Leu Pro Pro Glu Glu Leu Leu Arg Ser Ser Ala Asp Phe Leu Gln
1520                 1525                1530

Arg Leu Ser Ala Ile Leu Arg Thr Ser Leu Arg Phe Arg Leu Asp
1535                 1540                1545

Ala His Gly Gln Ala Met Val Phe Pro Tyr His Arg Pro Ser Pro
1550                 1555                1560

Gly Ser Glu Pro Arg Ala Arg Arg Glu Leu Ala Pro Glu Val Ile
1565                 1570                1575

Gly Ser Val Val Met Leu Glu Ile Asp Asn Arg Leu Cys Leu Gln
1580                 1585                1590

Ser Pro Glu Asn Asp His Cys Phe Pro Asp Ala Gln Ser Ala Ala
```

-continued

```
            1595                1600                1605

Asp Tyr Leu Gly Ala Leu Ser Ala Val Glu Arg Leu Asp Phe Pro
            1610                1615                1620

Tyr Pro Leu Arg Asp Val Arg Gly Glu Pro Leu Glu Pro Pro Glu
            1625                1630                1635

Pro Ser Val Pro Leu Leu Pro Leu Leu Val Ala Gly Ala Val Leu
            1640                1645                1650

Leu Leu Val Ile Leu Val Leu Gly Val Met Val Ala Arg Arg Lys
            1655                1660                1665

Arg Glu His Ser Thr Leu Trp Phe Pro Glu Gly Phe Ser Leu His
            1670                1675                1680

Lys Asp Val Ala Ser Gly His Lys Gly Arg Arg Glu Pro Val Gly
            1685                1690                1695

Gln Asp Ala Leu Gly Met Lys Asn Met Ala Lys Gly Glu Ser Leu
            1700                1705                1710

Met Gly Glu Val Ala Thr Asp Trp Met Asp Thr Glu Cys Pro Glu
            1715                1720                1725

Ala Lys Arg Leu Lys Val Glu Glu Pro Gly Met Gly Ala Glu Glu
            1730                1735                1740

Ala Val Asp Cys Arg Gln Trp Thr Gln His His Leu Val Ala Ala
            1745                1750                1755

Asp Ile Arg Val Ala Pro Ala Met Ala Leu Thr Pro Pro Gln Gly
            1760                1765                1770

Asp Ala Asp Ala Asp Gly Met Asp Val Asn Val Arg Gly Pro Asp
            1775                1780                1785

Gly Phe Thr Pro Leu Met Leu Ala Ser Phe Cys Gly Gly Ala Leu
            1790                1795                1800

Glu Pro Met Pro Thr Glu Glu Asp Glu Ala Asp Asp Thr Ser Ala
            1805                1810                1815

Ser Ile Ile Ser Asp Leu Ile Cys Gln Gly Ala Gln Leu Gly Ala
            1820                1825                1830

Arg Thr Asp Arg Thr Gly Glu Thr Ala Leu His Leu Ala Ala Arg
            1835                1840                1845

Tyr Ala Arg Ala Asp Ala Ala Lys Arg Leu Leu Asp Ala Gly Ala
            1850                1855                1860

Asp Thr Asn Ala Gln Asp His Ser Gly Arg Thr Pro Leu His Thr
            1865                1870                1875

Ala Val Thr Ala Asp Ala Gln Gly Val Phe Gln Ile Leu Ile Arg
            1880                1885                1890

Asn Arg Ser Thr Asp Leu Asp Ala Arg Met Ala Asp Gly Ser Thr
            1895                1900                1905

Ala Leu Ile Leu Ala Ala Arg Leu Ala Val Glu Gly Met Val Glu
            1910                1915                1920

Glu Leu Ile Ala Ser His Ala Asp Val Asn Ala Val Asp Glu Leu
            1925                1930                1935

Gly Lys Ser Ala Leu His Trp Ala Ala Ala Val Asn Asn Val Glu
            1940                1945                1950

Ala Thr Leu Ala Leu Leu Lys Asn Gly Ala Asn Lys Asp Met Gln
            1955                1960                1965
```

```
Asp Ser Lys Glu Glu Thr Pro Leu Phe Leu Ala Ala Arg Glu Gly
    1970                1975                1980

Ser Tyr Glu Ala Ala Lys Leu Leu Leu Asp His Phe Ala Asn Arg
    1985                1990                1995

Glu Ile Thr Asp His Leu Asp Arg Leu Pro Arg Asp Val Ala Gln
    2000                2005                2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
    2030                2035                2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
    2060                2065                2070

Pro Gln Gly Pro Arg Gly Arg Gly Lys Lys Leu Thr Leu Ala Cys
    2075                2080                2085

Pro Gly Pro Leu Ala Asp Ser Ser Val Thr Leu Ser Pro Val Asp
    2090                2095                2100

Ser Leu Asp Ser Pro Arg Pro Phe Gly Gly Pro Ala Ser Pro
    2105                2110                2115

Gly Gly Phe Pro Leu Glu Gly Pro Tyr Ala Ala Ala Thr Ala Thr
    2120                2125                2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
    2150                2155                2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
    2180                2185                2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Val
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250

His Trp Ala Ser Pro Ser Pro Pro Ser Leu Ser Asp Trp Ser Glu
    2255                2260                2265

Ser Thr Pro Ser Pro Ala Thr Ala Thr Gly Ala Met Ala Thr Thr
    2270                2275                2280

Thr Gly Ala Leu Pro Ala Gln Pro Leu Pro Leu Ser Val Pro Ser
    2285                2290                2295

Ser Leu Ala Gln Ala Gln Thr Gln Leu Gly Pro Gln Pro Glu Val
    2300                2305                2310

Thr Pro Lys Arg Gln Val Leu Ala
    2315                2320

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
      peptide

<400> SEQUENCE: 4

Val Met Val Ala Arg Arg Lys Arg Glu His Ser Thr Leu Trp
1               5                   10
```

METHODS OF TREATING CANCER USING NOTCH1 AND NOTCH3 ANTAGONISTS

RELATED APPLICATIONS

This application claims the benefit under 35 USC 119(e) of provisional application No. 61/247,298 filed Sep. 30, 2009, the contents of which are incorporated herein by reference.

FIELD OF THE INVENTION

The present invention relates to methods of treating cancer in general, and leukemia in particular, using Notch1 and Notch3 antagonists singly or in combination. Compositions and methods for the treatment and diagnosis of Notch-associated cancers are also provided.

SEQUENCE LISTING

The present application contains a Sequence Listing which has been submitted in ASCII format via EFS-Web and is hereby incorporated by reference in its entirety. Said ASCII copy, created on Sep. 3, 2010, is named P4371.txt and is 65,600 bytes in size.

BACKGROUND

The Notch receptor family is a class of evolutionarily conserved transmembrane receptors that transmit signals affecting development in organisms as diverse as sea urchins and humans. Notch receptors and their ligands Delta and Serrate (known as Jagged in mammals) are transmembrane proteins with large extracellular domains that contain epidermal growth factor (EGF)-like repeats. The number of Notch paralogues differs between species. For example, there are four Notch receptors in mammals (Notch1-Notch4), two in *Caenorhabditis elegans* (LIN-12 and GLP-1) and one in *Drosophila melanogaster* (Notch). Notch receptors are proteolytically processed during transport to the cell surface by a furin-like protease at a site S1, which is N-terminal to the transmembrane domain, producing an extracellular Notch (ECN) subunit and a Notch transmembrane subunit (NTM). These two subunits remain non-covalently associated and constitute the mature heterodimeric cell-surface receptor.

Notch1 ECN subunits contain 36 N-terminal EGF-like repeats followed by three tandemly repeated Lin 12/Notch Repeat (LNR) modules that precede the S1 site. Notch3 ECN has a similar structure, but with 34 EGF-like repeats. Each LNR module contains three disulfide bonds and a group of conserved acidic and polar residues predicted to coordinate a calcium ion. Within the EGF repeat region lie binding sites for the activating ligands. The Notch1 and Notch3 NTMs comprises an extracellular region (which harbors the S2 cleavage site), a transmembrane segment (which harbors the S3 cleavage site), and a large intracellular region (ICN or ICD) that includes a RAM domain, ankyrin repeats, a transactivation domain and a carboxy-terminal PEST domain. Stable association of the ECN and NTM subunits depends upon a heterodimerization domain (HD) comprising the carboxy-terminal end of the ECN (termed HD-N) and the extracellular amino-terminal end of NTM (termed HD-C). Before ligand-induced activation, Notch is maintained in a resting conformation by a negative regulatory region (NRR), which comprises the three LNRs and the HD domain.

Binding of a Notch ligand to the ECN subunit initiates two successive proteolytic cleavages that occur through regulated intramembrane proteolysis. The first cleavage by a metalloprotease (ADAM17) at site S2 renders the Notch transmembrane subunit susceptible to the second cleavage at site S3 close to the inner leaflet of the plasma membrane. Site S3 cleavage, which is catalyzed by a multiprotein complex containing presenilin and nicastrin and promoting γ-secretase activity, liberates the intracellular portion of the Notch transmembrane subunit, allowing it to translocate to the nucleus and activate transcription of target genes. (For review of the proteolytic cleavage of Notch, see, e.g., Sisodia et al., *Nat. Rev. Neurosci.* 3:281-290, 2002.)

Five Notch ligands of the Jagged and Delta-like classes have been identified in humans (Jagged1 (also termed Serrate1), Jagged2 (also termed Serrate2), Delta-like1 (also termed DLL1), Delta-like3 (also termed DLL3), and Delta-like4 (also termed DLL4)). Each of the ligands is a single-pass transmembrane protein with a conserved N-terminal Delta, Serrate, LAG-2 (DSL) motif essential for binding Notch. A series of EGF-like modules C-terminal to the DSL motif precede the membrane-spanning segment. Unlike the Notch receptors, the ligands have short cytoplasmic tails of 70-215 amino acids at the C-terminus. In addition, other types of ligands have been reported (e.g., DNER, NB3, and F3/Contactin). (For review of Notch ligands and ligand-mediated Notch activation, see, e.g., D'Souza et al., *Oncogene* 27:5148-5167, 2008.)

The Notch pathway functions during diverse developmental and physiological processes including those affecting neurogenesis in flies and vertebrates. In general, Notch signaling is involved in lateral inhibition, lineage decisions, and the establishment of boundaries between groups of cells. (See, e.g., Bray, *Mol. Cell Biol.* 7:678-679, 2006.) A variety of human diseases, including cancers and neurodegenerative disorders have been shown to result from mutations in genes encoding Notch receptors or their ligands. (See, e.g., Nam et al., *Curr. Opin. Chem. Biol.* 6:501-509, 2002.)

The role of Notch1 as an oncoprotein was demonstrated in leukemia involving T-cell progenitors. This role was first recognized in human acute lymphoblastic leukemia (T-ALL). (See, e.g., Aster et al., *Annu. Rev. Pathol. Mech. Dis.* 3:587-613, 2008.) T-ALL is an aggressive leukemia that preferentially afflicts children and adolescents. A recurrent t(7; 9)(q34; q34.3) chromosomal translocation, which creates a truncated, constitutively active variant of human Notch1, was identified in a subset of T-ALLs. In addition to the (7; 9) translocation, frequent gain-of-function mutations in human Notch1 were later discovered in more than 50% of all human T-ALLs. (See Weng et al., *Science,* 306:269-271, 2004.) Those mutations occur in the extracellular HD domain and the intracellular PEST domain. Other studies showed that retroviral-based expression of Notch1 ICN in bone marrow cells caused T-ALL in mouse models that received the transplanted bone marrow cells. (See Aster et al., *Mol. Cell Biol.* 20:7505-7515, 2000.)

Consistent with this role for Notch1 in leukemia involving T cell progenitors, Notch1 signaling has been shown to be essential for T cell development in mouse models, and Notch1-mediated signals promote T cell development at the expense of B cell development. (See, e.g., Wilson et al., *J. Exp. Med.* 194:1003-1012, 2001.) Further roles for Notch1 in leukemia have been described. Activating mutations in the Notch1 PEST domain have been reported at low frequency in human acute myeloid leukemia (AML) and in lineage switch leukemias, suggesting that activating mutations in Notch1 may occur in a leukemic stem cell that precedes myeloid and T-lineage commitment. (See Palomero et al., *Leukemia* 20:1963-1966, 2006.)

Prior to the discovery of the frequent Notch1 gain-of-function mutations in T-ALL, it was observed that enforced expression of Notch3 ICN in the thymus caused T-cell leukemia/lymphoma in transgenic mice. (See Bellavia et al., *EMBO J.* 19:3337-3348, 2000.) Notch3 mRNA was also reported as being expressed in all of thirty T-ALL patient samples analyzed, whereas it was not detected in normal peripheral blood T lymphocytes and non-T cell leukemias. (See Bellavia et al., *Proc. Nat'l Acad. Sci. USA* 99:3788-3793, 2002.)

Notch1 and Notch3 are also associated with a variety of other cancers. For instance, in solid tumors, increased Notch1 expression has been observed in human cancers of the cervix, colon, lung, pancreas, skin, and brain (see, e.g., Leong et al., *Blood* 107:2223-2233, 2006), and elevated expression of Notch1 is correlated with poor outcome in breast cancer (see, e.g., Parr et al., *Int. J. Mol. Med.* 14:779-786, 2004; Reedijk et al., *Cancer Res.* 65:8530-8537, 2005). A chromosomal translocation (15; 19) has been identified in a subset of non-small cell lung tumors, and the translocation is thought to elevate Notch3 transcription. In ovarian cancer, Notch3 gene amplification was found to occur in ~19% of tumors, and overexpression of Notch3 was found in more than half of ovarian serous carcinomas. Overexpression of activated Notch1 and Notch3 in transgenic mice induces mouse breast tumors, and overexpression of Notch3 is sufficient to induce choroid plexus tumor formation in a mouse model, suggesting a role for Notch3 in the development of certain brain tumors. (For review of Notch3 in cancer, see Shih et al. *Cancer Res.* 67:1879-1882, 2007.)

Certain anti-Notch1 antagonist antibodies having therapeutic efficacy have been described. (See U.S. Patent Application Publication No. US 2009/0081238 A1, expressly incorporated by reference in its entirety herein.) For example, such antibodies bind to the negative regulatory region (NRR) of Notch1, block Notch1 signaling, disrupt angiogenesis and vascularization, and inhibit tumor growth in mouse xenograft models of non small cell lung carcinoma and colon adenocarcinoma. Certain antibodies described therein bind to LNR-A and LNR-B (the first and second of the three LIN12/Notch Repeats) and HD-C of Notch1 NRR. Other anti-Notch1 antibodies that bind to the EGF repeat region of Notch1 and block Notch1 activity, perhaps by blocking ligand binding, have also been described. (See International Publication No. WO 2008/091641.)

Certain anti-Notch3 antagonist antibodies have also been described. (See U.S. Patent Application Publication No. US 2008/0226621 A1, expressly incorporated by reference in its entirety herein.) Such antibodies bind to the negative regulatory region (NRR) of Notch3 and block Notch3 signaling. Certain antibodies described therein bind to LNR-A (the first of the three LIN12/Notch Repeats) and HD-C (referred to alternatively as the second dimerization domain in US 2008/0226621 A1) of Notch3 NRR. Other anti-Notch3 antibodies that bind to the EGF-like repeat region of Notch3 and block Notch3 activity, perhaps by blocking ligand binding, have also been described. (See Li et al., *J. Biol. Chem.* 283:8046-8054, 2008.)

Gamma-secretase inhibitors (GSIs), which are pan-Notch inhibitors that inhibit multiple Notch receptors, have been proposed for treatment of Notch-related diseases, and in fact have been used in clinical trials for the treatment of T-ALL. (See Roy et al., *Curr. Opin. Genet. Dev.* 17:52-59, 2007; Deangelo et al., *J. Clin. Oncol.* 2006 *ASCO Annual Meeting Proceedings Part I* 24:6586, 2006.) However, GSIs cause weight loss and intestinal goblet cell metaplasia, reflecting the role that Notch plays in determining cell fate by maintaining proliferation of intestinal crypt progenitor cells and prohibiting differentiation to a secretory cell fate. (See van Es et al., *Nature* 435:959-963, 2005). Although these side effects of pan-Notch inhibition may be manageable in a clinical setting, inhibitors that target individual Notch receptors, and therefore minimize or reduce these side effects, may be advantageous.

There is a need in the art for further therapeutic methods of treating cancer by targeting Notch receptors. The invention described herein meets the above-described needs and provides other benefits.

SUMMARY

The present invention relates to the treatment of cancer using Notch antagonists singly or in combination. The present invention specifically relates, in part, to the characterization of different classes of T-ALL. One class of T-ALL is sensitive to treatment with GSI and is also sensitive to treatment with a Notch1-specific antagonist. In contrast, another class of T-ALL is sensitive to treatment with GSI, but insensitive (i.e., resistant) to treatment with a Notch1-specific antagonist. As shown herein, the latter class of T-ALL is partially sensitive to treatment with a Notch3-specific antagonist, and even more sensitive to a combination of a Notch1-specific antagonist and a Notch3-specific antagonist. These results suggest a role for both Notch1 and Notch3 in leukemias, particularly T cell progenitor leukemias such as T-ALL.

In one aspect, a method of treating a GSI-responsive cancer that does not respond to a Notch1-specific antagonist is provided, the method comprising administering to a patient having such cancer an effective amount of a Notch3-specific antagonist. In certain embodiments, the cancer is T-cell leukemia. In certain embodiments, the T-cell leukemia is a lymphoblastic leukemia. In certain embodiments, the T-cell leukemia is T-ALL. In certain embodiments, the Notch3-specific antagonist is an anti-Notch3 antagonist antibody. In certain embodiments, the anti-Notch3 antagonist antibody is an anti-Notch3 NRR antibody. In certain embodiments, the anti-Notch3 NRR antibody binds to the LNR-A and HD-C domains of Notch3 NRR. In certain embodiments, the anti-Notch3 NRR antibody comprises the heavy and light chain variable region CDRs of antibody 256A-4 or 256A-8. In certain embodiments, the anti-Notch3 NRR antibody is a humanized form of antibody 256A-4 or 256A-8. In certain embodiments, the anti-Notch3 antagonist antibody is an anti-Notch3 antibody that binds to one or more EGF-like repeats of Notch3.

In a further embodiment, the method further comprises administering an effective amount of a Notch1-specific antagonist. In certain embodiments, the Notch1-specific antagonist that is administered is an anti-Notch1 antagonist antibody. In certain embodiments, the anti-Notch1 antagonist antibody is an anti-Notch1 NRR antibody. In certain embodiments, the anti-Notch1 NRR antibody binds to the LNR-A, LNR-B, and HD-C domains of Notch1 NRR. In certain embodiments, the anti-Notch1 NRR antibody is selected from Antibody A, A-1, A-2, and A-3. In certain embodiments, the anti-Notch1 NRR antibody comprises the heavy and light chain variable region CDRs of an antibody selected from Antibody A, A-1, A-2, and A-3. In certain embodiments, the anti-Notch1 antagonist antibody is an anti-Notch1 antibody that binds to one or more EGF-like repeats of Notch1.

In a further aspect of the invention, an antibody that binds to activated Notch3 ICD is provided. In certain embodiments, the antibody binds to the peptide of SEQ ID NO:4. In certain embodiments, the antibody is polyclonal. In certain embodiments, the antibody is monoclonal.

In a further aspect of the invention, a method of identifying a cancer that is suitable for treatment with an antagonist of Notch3 is provided, the method comprising contacting a sample of the cancer with the antibody of claim 15, and determining whether significantly increased levels of activated Notch3 are present in the sample, wherein the presence of significantly increased levels of activated Notch3 indicates that the cancer is suitable for treatment with an antagonist of Notch3. In certain embodiments, the cancer is GSI-responsive.

The above and further aspects and embodiments of the invention are provided herein.

BRIEF DESCRIPTION OF THE FIGURES

FIG. 1A-1D shows an alignment of human Notch1 (SEQ ID NO:1) and mouse Notch1 (SEQ ID NO:2), with motifs and other features indicated.

FIG. 2 shows the sequence of human Notch3 (SEQ ID NO:3). The EGF repeat region extends from amino acid residue 43 to 1383; the LNR modules extend from amino acid residue 1384 to 1503, with LNR-A extending from amino acid residues 1384-1422; and the dimerization domain extends from amino acid residue 1504 to 1640, with HD-C extending from amino acid residues 1572-1640.

FIG. 8, right panel, shows that decreased staining for Ki-67 (i.e., decreased proliferation) correlates inversely with the number of Annexin V/7-AAD double negative (i.e., non-apoptotic) cells.

DETAILED DESCRIPTION OF EMBODIMENTS

I. Definitions

Figure 3A:
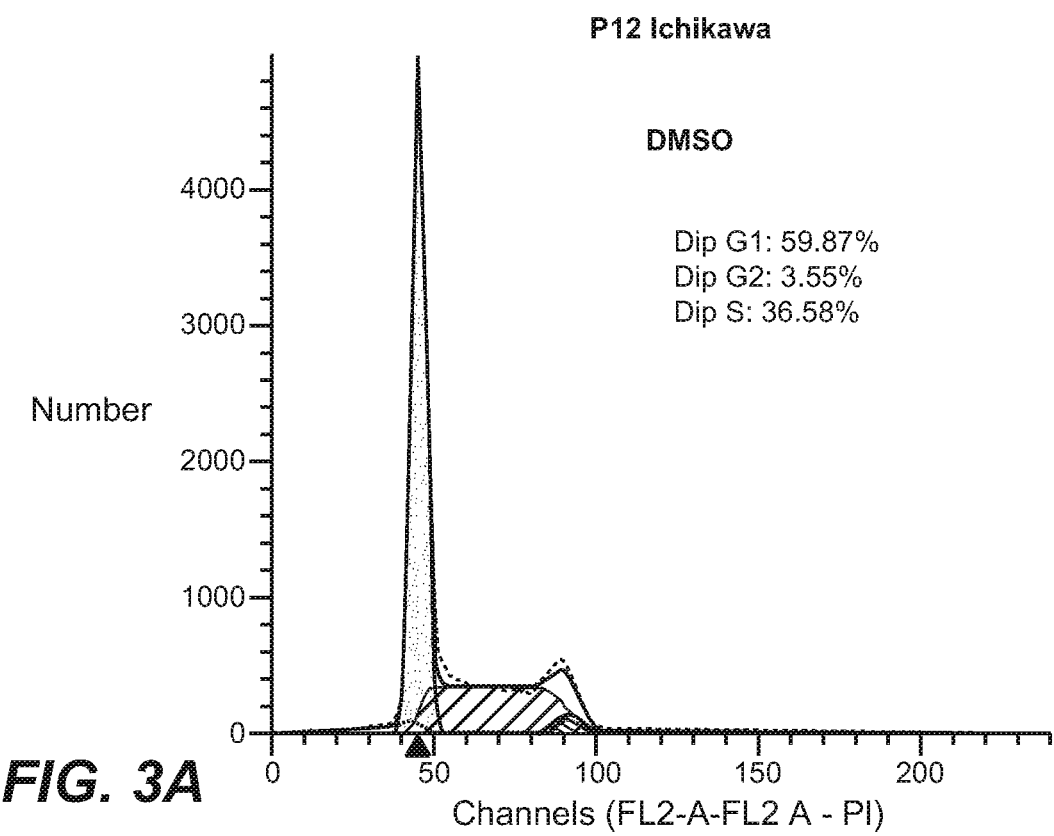
FIG. 3A-3D shows that the T-ALL cell line, P-12 Ichikawa, is resistant to both GSI (DAPT) and anti-NRR1 (α-N1).
Figure 3B:
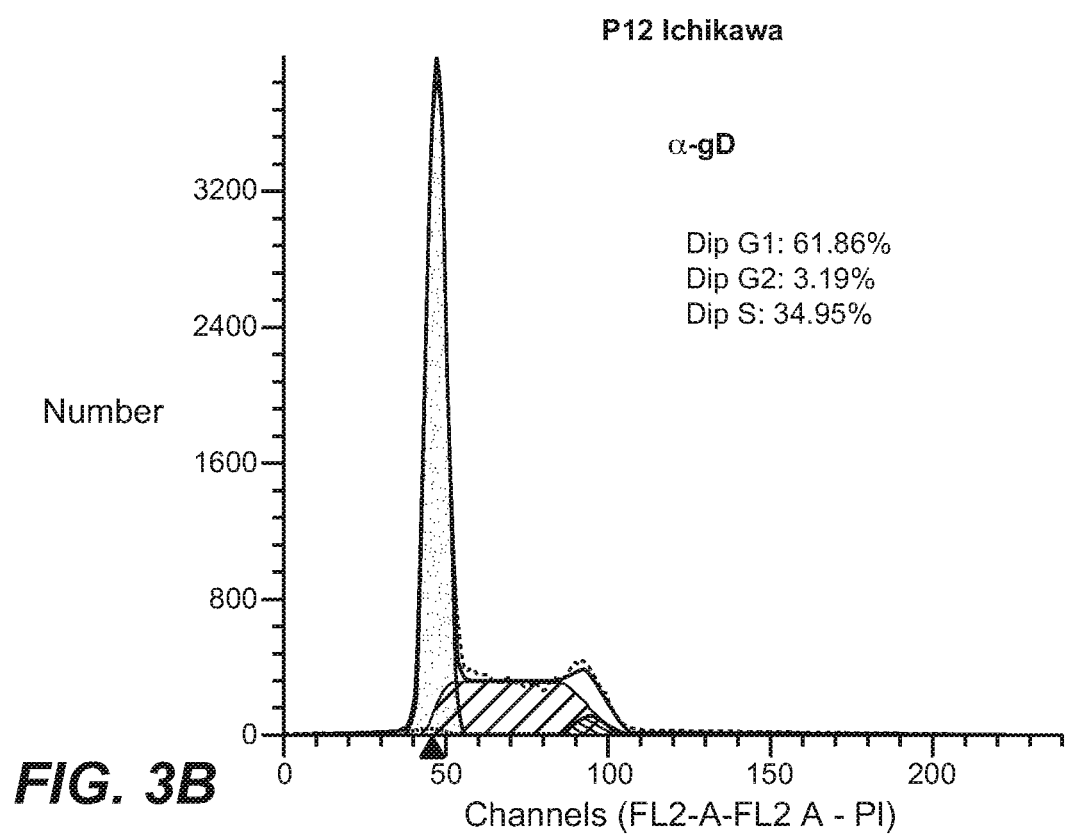
Figure 3C:
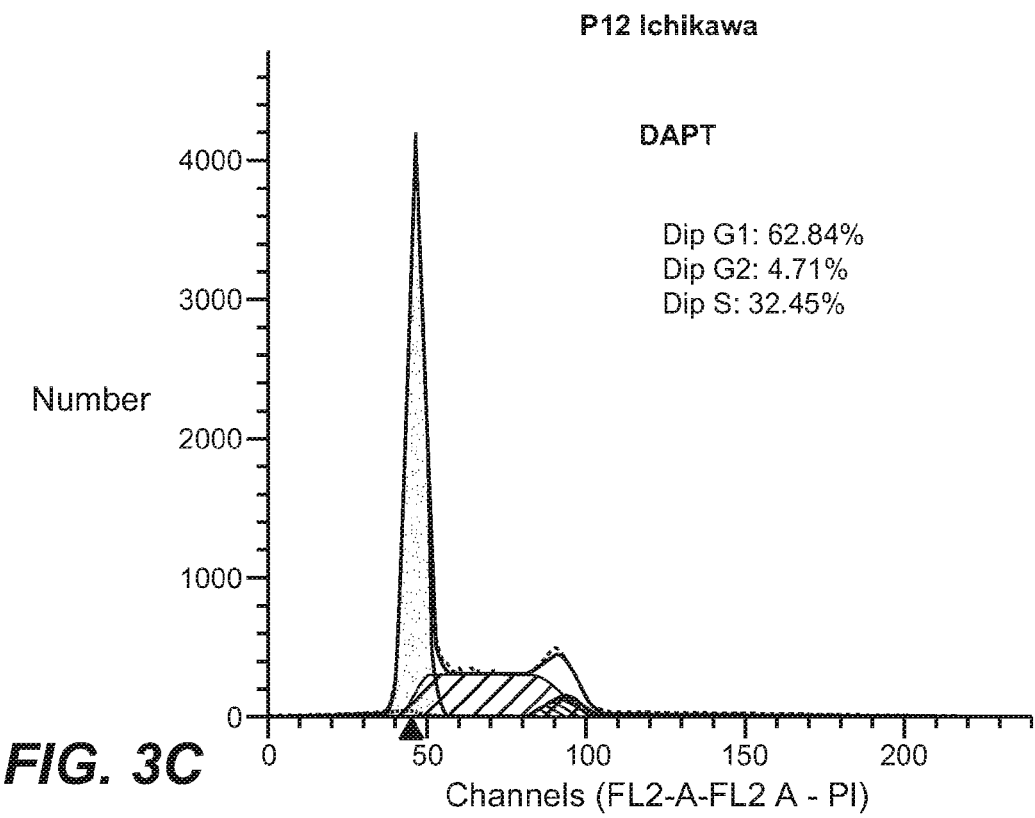
Figure 3D:
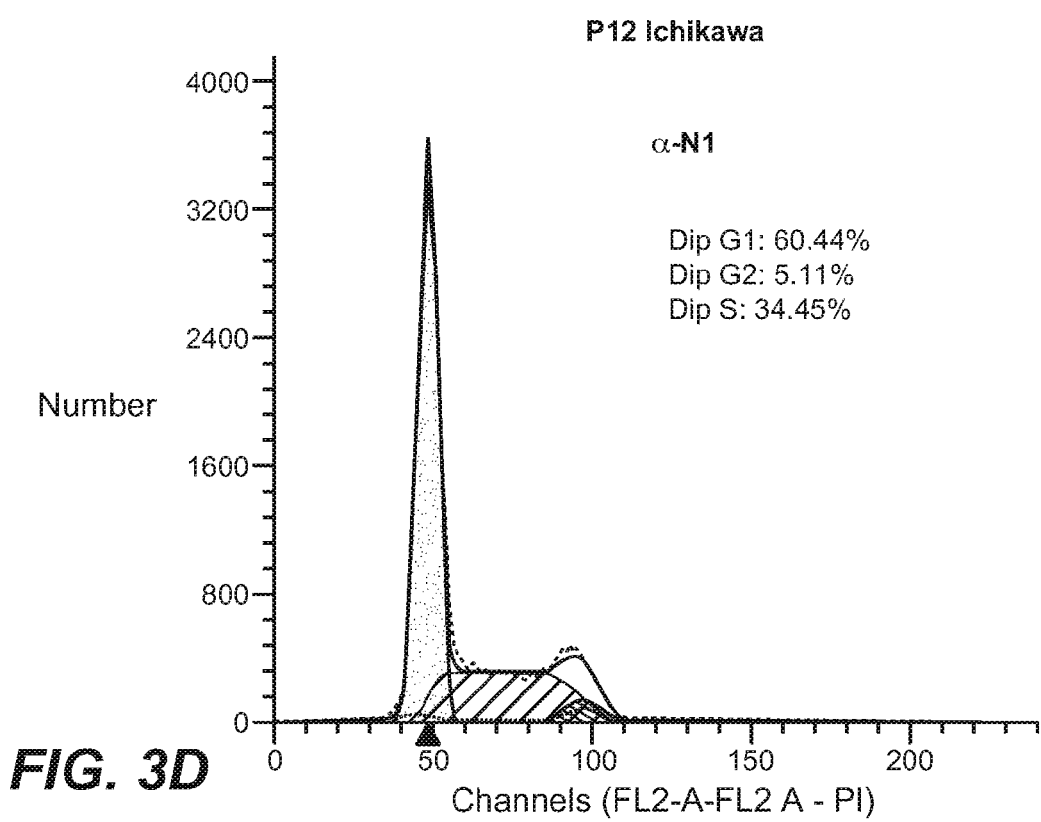
Figure 4A:
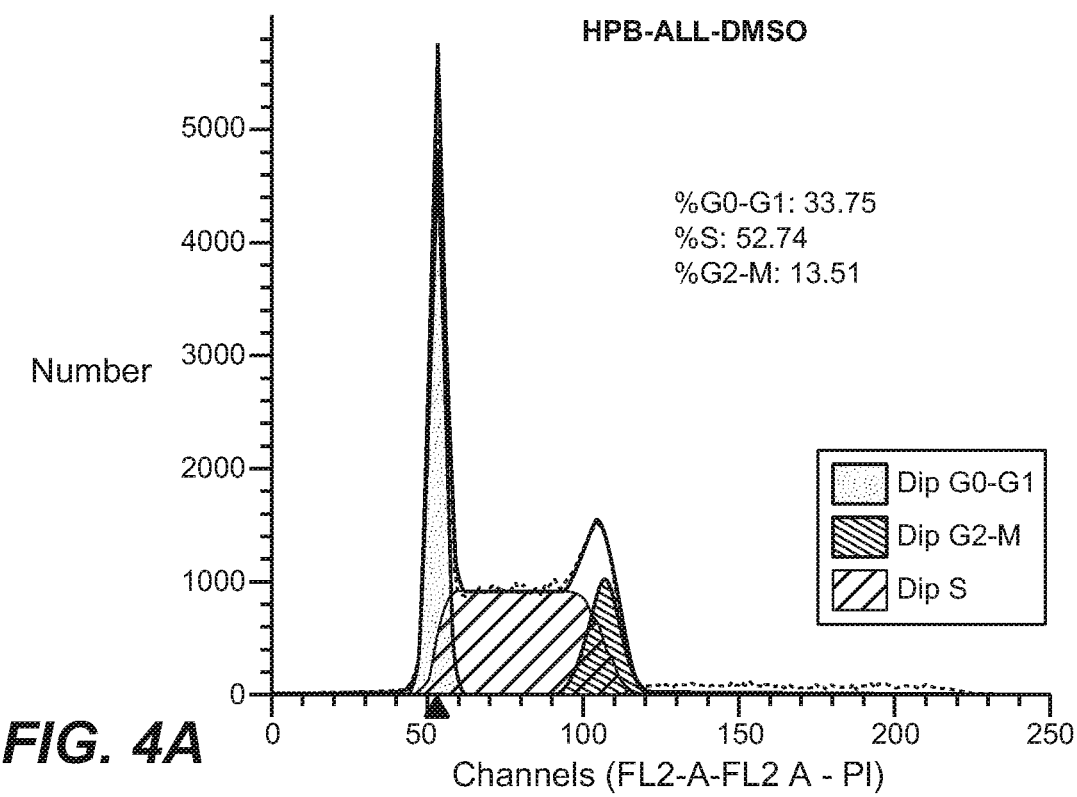
FIG. 4A-4D shows that the T-ALL cell line, HPB-ALL, is sensitive to both GSI (DAPT) and anti-NRR1 (α-N1), as evidenced by the accumulation of cells in G0/G1 and the reduction of cells in S/G2/M, relative to control cells.
Figure 4B:
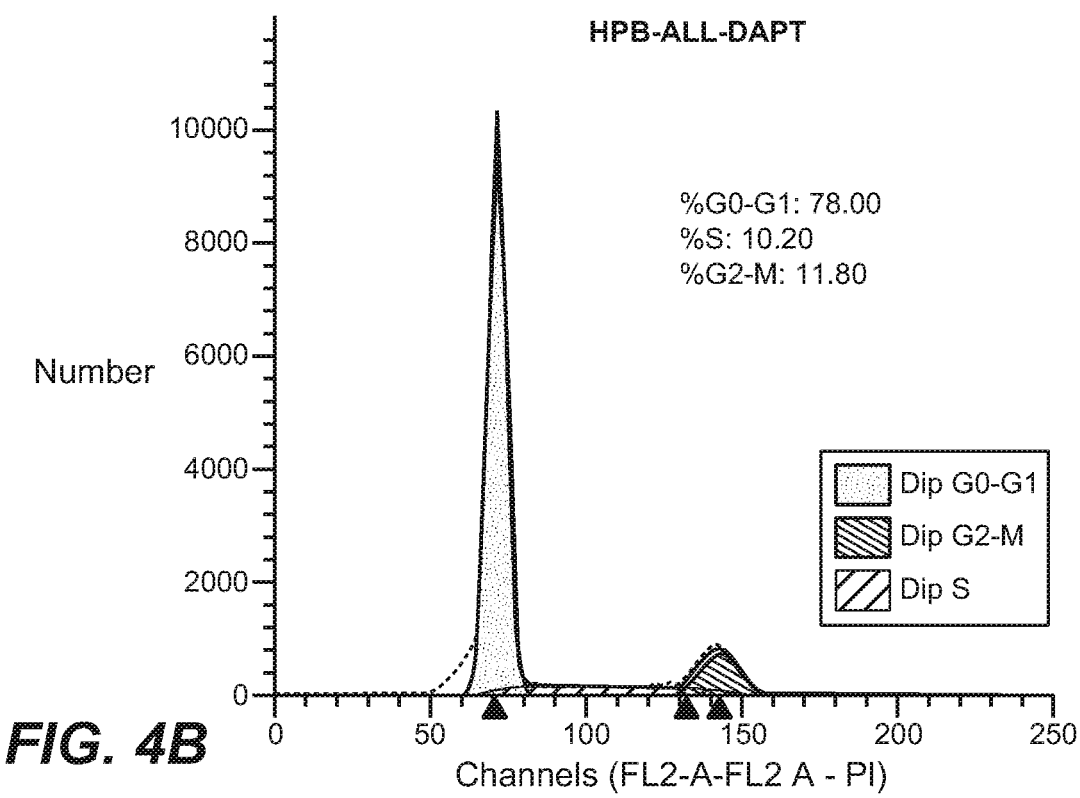
Figure 4C:
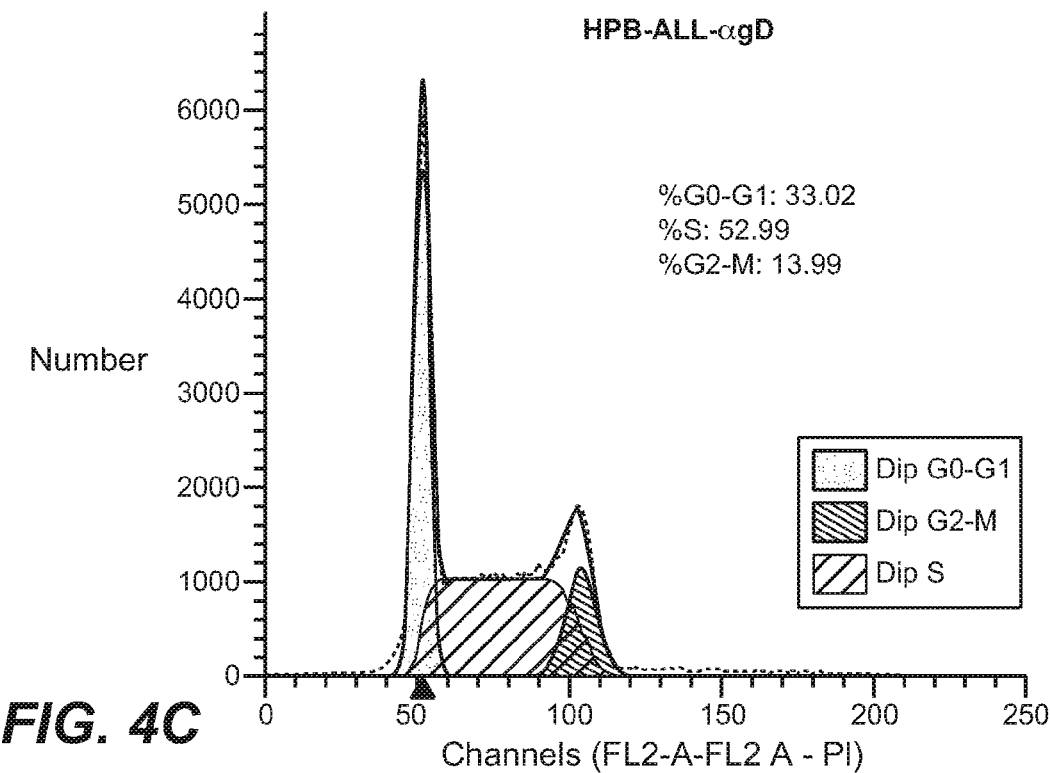
Figure 4D:
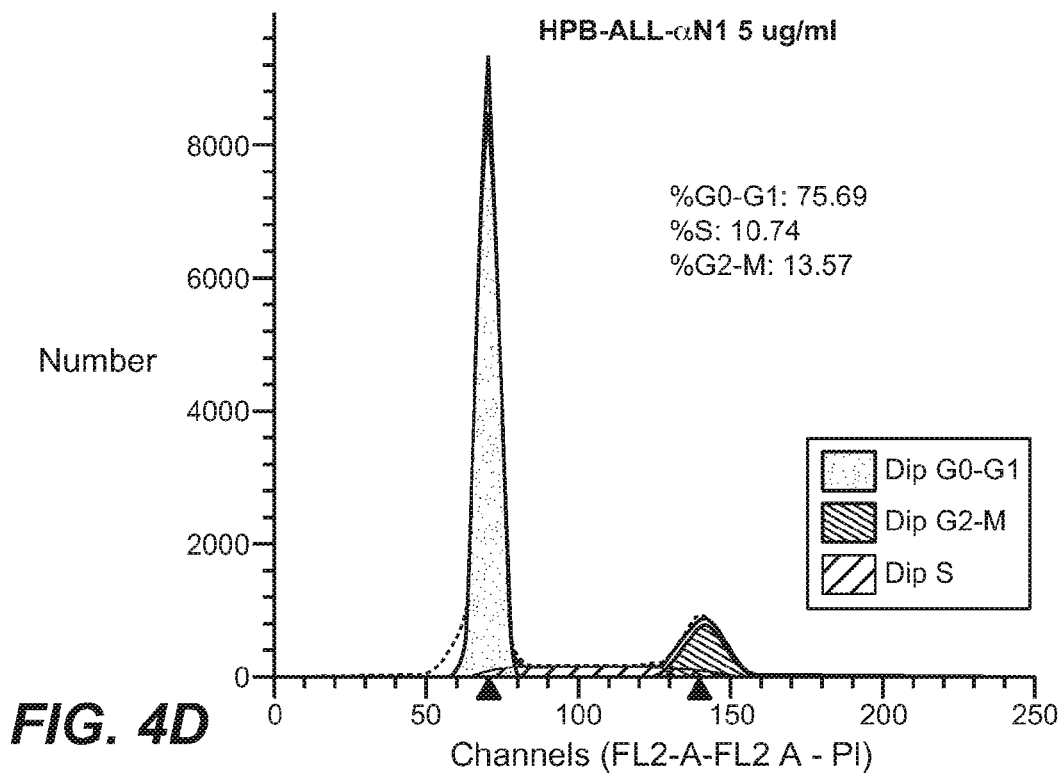
Figure 5A:
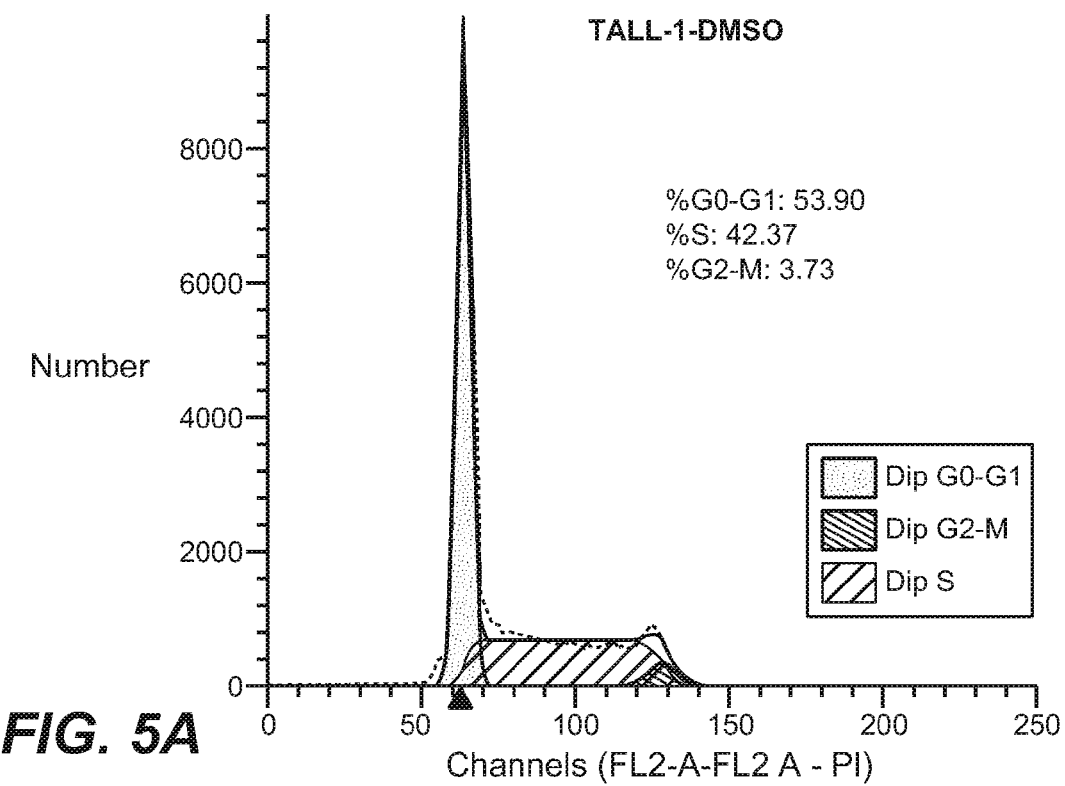
FIG. 5A-5D shows that the T-ALL cell line, TALL-1, is sensitive to GSI but resistant to anti-NRR1 (α-N1).
Figure 5B:
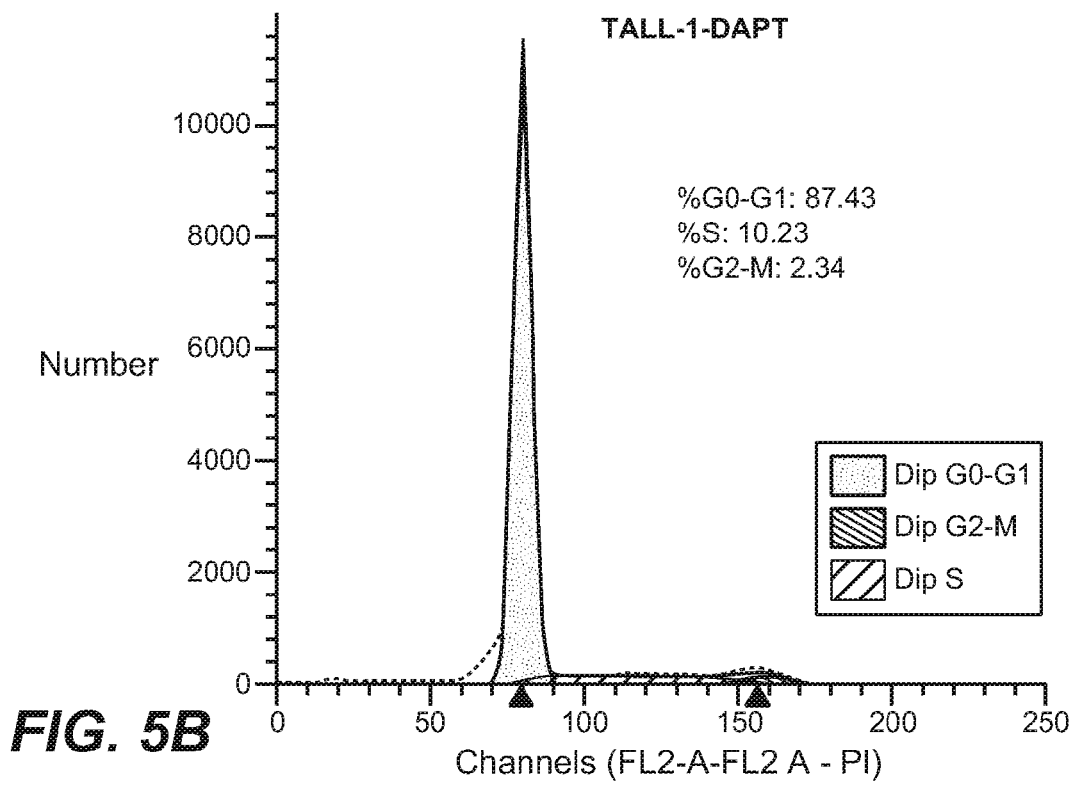
Figure 5C:
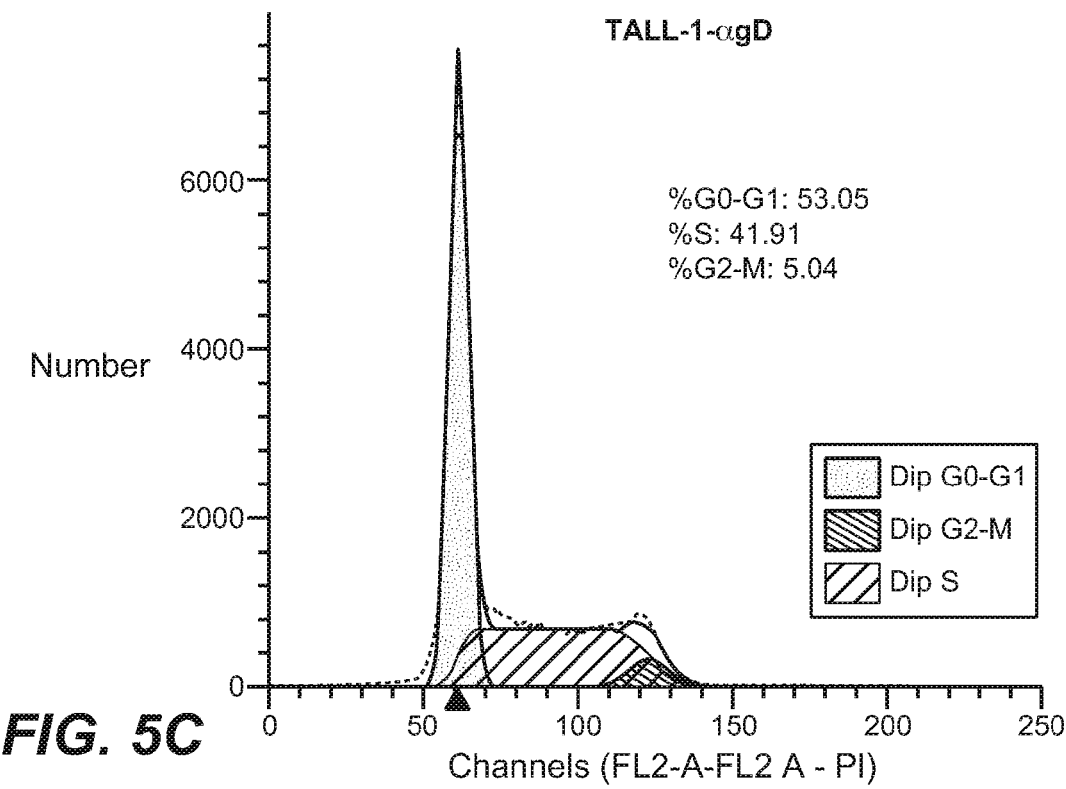
Figure 5D:
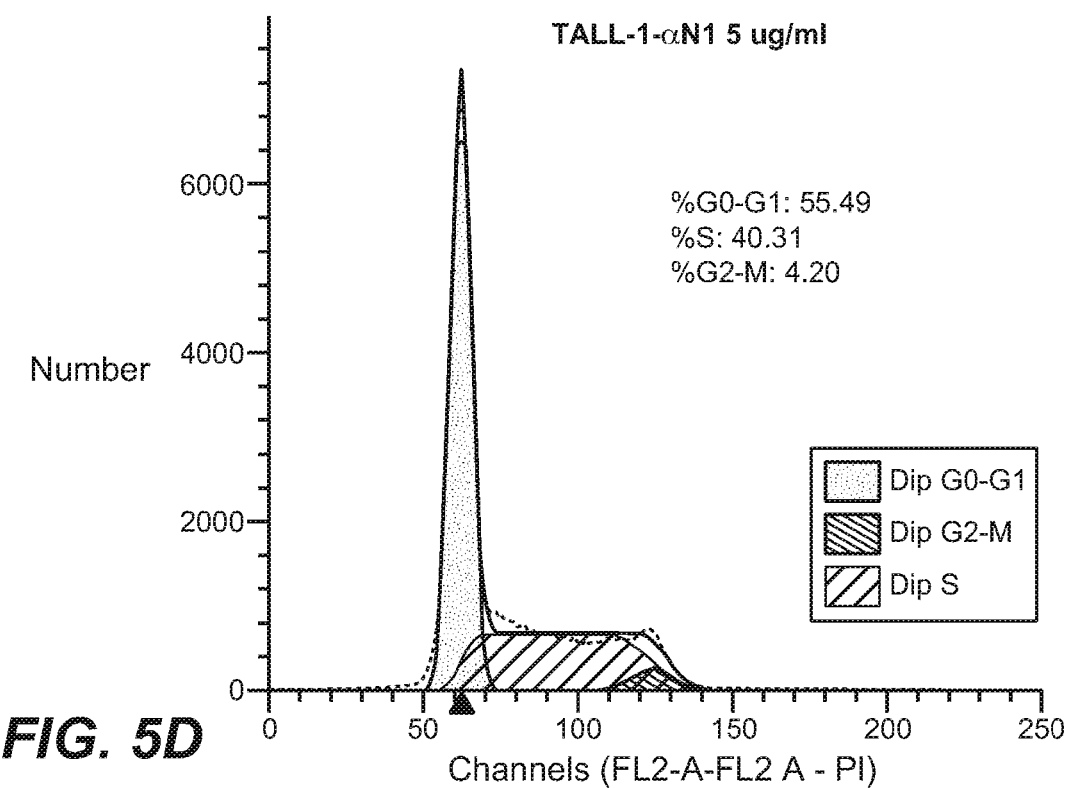

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

The term "Notch," as used herein, refers, unless specifically or contextually indicated otherwise, to any native or variant (whether native or synthetic) Notch polypeptide (Notch1-4). The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch" generally refers to a polypeptide comprising an amino acid sequence of a naturally occurring, non-mutated Notch protein. The term "wild-type Notch sequence" generally refers to an amino acid sequence found in a naturally occurring, non-mutated Notch.

The term "Notch1," as used herein, refers, unless specifically or contextually indicated otherwise, to any native or variant (whether native or synthetic) Notch1 polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch1" generally refers to a polypeptide comprising an amino acid sequence of a naturally occurring, non-mutated Notch1 protein. The term "wild type Notch1 sequence" generally refers to an amino acid sequence found in a naturally occurring, non-mutated Notch1.

The term "Notch1 ligand," as used herein, refers, unless specifically or contextually indicated otherwise, to any native or variant (whether native or synthetic) Notch1 ligand (for example, Jagged1, Jagged2, Delta-like1, Delta-like3, and/or Delta-like4) polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch1 ligand" generally refers to a polypeptide comprising an amino acid sequence of a naturally occurring, non-mutated Notch1 ligand. The term "wild type Notch1 ligand sequence" generally refers to an amino acid sequence found in a naturally occurring, non-mutated Notch1 ligand.

The term "Notch1 NRR," as used herein, refers, unless specifically or contextually indicated otherwise, to any native or variant (whether native or synthetic) polypeptide region of Notch1 consisting of the 3 LNR modules and the amino acid sequences extending from the carboxy-terminus of the LNR modules to the transmembrane domain, such sequences including the HD domain (HD-N and HD-C). Exemplary Notch1 NRRs consist of the region from about amino acid 1446 to about amino acid 1735 of the human Notch1 amino acid sequence (SEQ ID NO:1, FIG. 1), and the region from about amino acid 1446 to about amino acid 1725 of the mouse Notch1 amino acid sequence (SEQ ID NO:2, FIG. 1). The term "native sequence Notch1 NRR" specifically encompasses naturally occurring truncated forms, naturally occurring variant forms (e.g., alternatively spliced forms) and naturally-occurring allelic variants of a Notch1 NRR. The term "wild-type Notch1 NRR" generally refers to a naturally occurring, non-mutated Notch1 NRR. In some embodiments, a Notch1 NRR is contained in a Notch1, such as, for example, a Notch1 processed at the 51, S2 and/or S3 site(s), or an unprocessed Notch1. In some embodiments, a Notch1 NRR contains two or more non-covalently linked fragments of a Notch1 NRR amino acid sequence, e.g., a fragment containing amino acids 1446 to 1664 of SEQ ID NO:1 non-covalently linked to a fragment containing amino acids 1665 to 1735 of SEQ ID NO:1. In another embodiment, a fragment containing amino acids 1446 to 1654 of SEQ ID NO:2 is non-covalently linked to a fragment containing amino acids 1655 to 1725 of SEQ ID NO:2.

The term "increased Notch1 signaling," as used herein, refers to an increase in Notch1 signaling that is significantly above the level of Notch1 signaling observed in a control under substantially identical conditions. In certain embodiments, the increase in Notch1 signaling is at least two fold, three fold, four fold, five fold, or ten fold above the level observed in the control.

The term "decreased Notch1 signaling," as used herein, refers to a decrease in Notch1 signaling that is significantly below the level of Notch1 signaling observed in a control under substantially identical conditions. In certain embodiments, the decrease in Notch1 signaling is at least two fold, three fold, four fold, five fold, or ten fold below the level observed in the control.

In certain embodiments, Notch1 signaling (i.e., increased or decreased Notch1 signaling) is assessed using a suitable reporter assay, e.g, as described in Example 5 of U.S. Patent Application Publication No. US 2009/0081238 A1. In certain embodiments, Notch1 signaling is assessed using an in vitro activity assay, such as the C2C12 myoblast differentiation assay or the HUVEC cell sprouting assay, as described in Examples 5 and 7, respectively, of US 2009/0081238 A1. In certain embodiments, Notch1 signaling is assessed using an in vivo xenograft model, such as the Calu6 and HM7 models described in Example 8 of US 2009/0081238 A1.

The terms "Notch1 activating mutation" and "mutation that activates Notch1 signaling" refer to an insertion of one or more amino acids, a deletion of one or more amino acids, or a substitution of one or more amino acids relative to a Notch1 wild-type amino acid sequence that results in increased Notch1 signaling as compared with Notch1 signaling from the corresponding Notch1 wild-type amino acid sequence, or to an insertion of one or more nucleotides, a deletion of one or more nucleotides, a translocation of one or more nucleotides, or a substitution of one or more nucleotides relative to a Notch1 wild-type nucleic acid sequence that results in increased Notch1 signaling in a cell containing the mutant nucleic acid sequence as compared with Notch1 signaling in a cell containing the corresponding Notch1 wild-type nucleic acid sequence. Notch1 signaling from a Notch1 receptor containing an activating mutation may be ligand dependent or ligand independent.

The term "anti-Notch1 antibody" or "an antibody that binds to Notch1" refers to an antibody that is capable of binding Notch1 with sufficient affinity such that the antibody is useful as a diagnostic and/or therapeutic agent in targeting Notch1. Preferably, the extent of binding of an anti-Notch1 antibody to an unrelated, non-Notch protein is less than about 10% of the binding of the antibody to Notch1 as measured, e.g., by a radioimmunoassay (RIA). In certain embodiments, an antibody that binds to Notch1 has a dissociation constant (Kd) of $\leq 1$ µM, $\leq 0.5$ µM, $\leq 100$ nM, $\leq 50$ nM, $\leq 10$ nM, $\leq 5$ nM, $\leq 1$ nM, $\leq 0.5$ nM, or $\leq 0.1$ nM. In certain embodiments, an anti-Notch1 antibody binds to an epitope of Notch1 that is conserved among Notch1 from different species, e.g., rodents (mice, rats) and primates.

The term "anti-Notch1 NRR antibody" or "an antibody that binds to Notch1 NRR" refers to an antibody that is capable of binding Notch1 NRR with sufficient affinity such that the antibody is useful as a diagnostic and/or therapeutic agent in targeting Notch1. Preferably, the extent of binding of an anti-Notch1 NRR antibody antibody to an unrelated, non-Notch protein is less than about 10% of the binding of the antibody to Notch1 NRR as measured, e.g., by a radioimmunoassay (RIA). In certain embodiments, an antibody that binds to Notch1 NRR has a dissociation constant (Kd) of $\leq 1$ µM, $\leq 0.5$ µM, $\leq 100$ nM, $\leq 50$ nM, $\leq 10$ nM, $\leq 5$ nM, $\leq 1$ nM, $\leq 0.5$ nM, or $\leq 0.1$ nM. In certain embodiments, an anti-Notch1 NRR antibody binds to an epitope of Notch that is conserved among Notch from different species, e.g., rodents (mice, rats) and primates.

The term "Notch1-specific antagonist" refers to an agent that effects decreased Notch1 signaling, as defined above, and does not significantly affect signaling by another Notch receptor (Notch2, 3, or 4 in mammals).

An "anti-Notch1 antagonist antibody" is an anti-Notch1 antibody (including an anti-Notch1 NRR antibody) that effects decreased Notch1 signaling, as defined above.

Reference to "Antibody A, A-1, A-2, and A-3," singly or in any combination, means the heavy and light chain variable regions of the phage and reformatted antibodies designated Antibody A, A-1, A-2, and A-3 in U.S. Patent Application Publication No. US 2009/0081238 A1, unless otherwise indicated.

The term "Notch3," as used herein, refers, unless specifically or contextually indicated otherwise, to any native or variant (whether native or synthetic) Notch3 polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch3" generally refers to a polypeptide comprising an amino acid sequence of a naturally occurring, non-mutated Notch3 protein. The term "wild type Notch3 sequence" generally refers to an amino acid sequence found in a naturally occurring, non-mutated Notch3.

The term "Notch3 ligand," as used herein, refers, unless specifically or contextually indicated otherwise, to any native or variant (whether native or synthetic) Notch3 ligand (for example, Jagged1, Jagged2, Delta-like1, Delta-like3, and/or Delta-like4) polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch3 ligand" generally refers to a polypeptide comprising an amino acid sequence of a naturally occurring, non-mutated Notch3 ligand. The term "wild type Notch3 ligand sequence" generally refers to an amino acid sequence found in a naturally occurring, non-mutated Notch3 ligand.

The term "activated Notch3 ICD" refers to the Notch3 cleavage product that results from cleavage at site S3 and that is capable of translocating to the nucleus. In certain embodiments, activated Notch3 ICD consists of amino acids 1662-2321 of human Notch3 (SEQ ID NO:3).

The term "Notch3 NRR," as used herein, refers, unless specifically or contextually indicated otherwise, to any native or variant (whether native or synthetic) polypeptide region of Notch3 consisting of the 3 LNR modules and the amino acid sequences extending from the carboxy-terminus of the LNR modules to the transmembrane domain, such sequences including the HD domain (HD-N and HD-C). Exemplary Notch3 NRRs consist of the region from about amino acid 1384 to about amino acid 1640 of the human Notch3 amino acid sequence (SEQ ID NO:3, FIG. 2). The term "native sequence Notch3 NRR" specifically encompasses naturally occurring truncated forms, naturally occurring variant forms (e.g., alternatively spliced forms) and naturally-occurring allelic variants of a Notch3 NRR. The term "wild-type Notch3 NRR" generally refers to a naturally occurring, non-mutated Notch3 NRR. In some embodiments, a Notch3 NRR is contained in a Notch3, such as, for example, a Notch3 processed at the S1, S2 and/or S3 site(s), or an unprocessed Notch3. In some embodiments, a Notch3 NRR contains two or more non-covalently linked fragments of a Notch3 NRR amino acid sequence, e.g., a fragment containing amino acids 1384 to 1571 of human Notch3 (SEQ ID NO:3) non-covalently linked to a fragment containing amino acids 1572 to 1640 of human Notch3 (SEQ ID NO:3).

The term "increased Notch3 signaling," as used herein refers to an increase in Notch3 signaling that is significantly above the level of Notch3 signaling observed in a control under substantially identical conditions. In certain embodiments, the increase in Notch3 signaling is at least two fold, three fold, four fold, five fold, or ten fold above the level observed in the control.

The term "decreased Notch3 signaling," as used herein refers to a decrease in Notch3 signaling that is significantly below the level of Notch3 signaling observed in a control under substantially identical conditions. In certain embodiments, the decrease in Notch3 signaling is at least two fold, three fold, four fold, five fold, or ten fold below the level observed in the control.

In certain embodiments, Notch3 signaling (i.e., increased or decreased Notch3 signaling) is assessed using a suitable reporter assay, e.g, as described in Example 5 of U.S. Patent Application Publication No. US 2008/0226621 A1. In certain embodiments, Notch3 signaling is assessed using an in vitro activity assay, such as the apoptosis, cell migration, invasion, and morphology assays described in Example 7 of U.S. Patent Application Publication No. US 2008/0226621 A1. In certain embodiments, Notch3 signaling is assessed using an in vivo xenograft model, such as those described in Example 11 of US 2008/0226621 A1.

The term "anti-Notch3 antibody" or "an antibody that binds to Notch3" refers to an antibody that is capable of binding Notch3 with sufficient affinity such that the antibody is useful as a diagnostic and/or therapeutic agent in targeting Notch3. Preferably, the extent of binding of an anti-Notch3 antibody to an unrelated, non-Notch protein is less than about 10% of the binding of the antibody to Notch3 as measured, e.g., by a radioimmunoassay (RIA). In certain embodiments, an antibody that binds to Notch3 NRR has a dissociation constant (Kd) of ≤1 µM, ≤0.5 µM, ≤100 nM, ≤50 nM, ≤10 nM, ≤5 nM, ≤1 nM, ≤0.5 nM, or ≤0.1 nM. In certain embodiments, an anti-Notch3 antibody binds to an epitope of Notch3 that is conserved among Notch3 from different species, e.g., rodents (mice, rats) and primates.

The term "anti-Notch3 NRR antibody" or "an antibody that binds to Notch3 NRR" refers to an antibody that is capable of binding Notch3 NRR with sufficient affinity such that the antibody is useful as a diagnostic and/or therapeutic agent in targeting Notch3. Preferably, the extent of binding of an anti-Notch3 NRR antibody to an unrelated, non-Notch protein is less than about 10% of the binding of the antibody to Notch3 NRR as measured, e.g., by a radioimmunoassay (RIA). In certain embodiments, an antibody that binds to Notch3 NRR has a dissociation constant (Kd) of ≤1 µM, ≤0.5 µM, ≤100 nM, ≤50 nM, ≤10 nM, ≤5 nM, ≤1 nM, ≤0.5 nM, or ≤0.1 nM. In certain embodiments, an anti-Notch3 NRR antibody binds to an epitope of Notch3 that is conserved among Notch3 from different species, e.g., rodents (mice, rats) and primates.

The term "Notch3-specific antagonist" refers to an agent that effects decreased Notch3 signaling, as defined above, and does not significantly affect signaling by another Notch receptor (Notch1, 2, or 4 in mammals).

An "anti-Notch3 antagonist antibody" is an anti-Notch3 antibody (including an anti-Notch3 NRR antibody) that effects decreased Notch3 signaling, as defined above.

Reference to "antibody 256A-4 and 256A-8," singly or in combination, means the mouse monoclonal antibodies designated 256A-4 and 256A-8 in U.S. Patent Application Publication No. 2008/0226621 A1.

The term "antagonist" refers to an agent that significantly inhibits (either partially or completely) the biological activity of a target molecule.

An "antibody that binds activated Notch3 ICD" refers to an antibody that binds activated Notch3 ICD such that the antibody is useful in distinguishing activated Notch3 ICD from Notch3 comprising an intact NTM.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147 (1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 03:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Application Publication US 2008/0181888 A1, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describe affinity maturation by VH and VL domain shuffling. Random mutagenesis of HVR and/or framework residues is described by, for example, in Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226: 889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

A "disorder" is any condition or disease that would benefit from treatment with a composition or method of the invention. This includes chronic and acute disorders including those pathological conditions which predispose the mammal to the disorder in question. Non-limiting examples of disorders to be treated herein include conditions such as cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all precancerous and cancerous cells and tissues. The terms "cancer," "cancerous," "cell proliferative disorder," "proliferative disorder," and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The term "leukemia" refers to an acute or chronic disease characterized by an abnormal increase in the number of white blood cells (leukocytes) in hemopoietic tissues, other organs, and often in the blood. Leukemias include, but are not limited to, acute lymphoblastic leukemia (ALL), including T-lineage acute lymphoblastic leukemia (T-ALL) as well as other lymphocytic leukemias; adult T-cell leukemia/lymphoma; chronic myeloid (myelogenous) leukemia (CML), acute myeloid (myelogenous) leukemia (AML), and other granulocytic leukemias; and lineage switch leukemias.

The term "T-cell leukemia" refers to a leukemia characterized by an abnormal increase in the number of T-lineage lymphoblasts or T-lymphocytes.

The term "T-cell progenitor leukemia" refers to a leukemia characterized by an abnormal increase in the number of T-lineage lymphoblasts.

A "GSI-responsive cancer" is a cancer (such as a leukemia) that responds to a gamma secretase inhibitor or that would respond to a gamma secretase inhibitor if treated with such.

A cancer that "responds" to a therapeutic agent is one that shows a significant decrease in cancer or tumor progression, including but not limited to, (1) inhibition, to some extent, of tumor growth, including slowing down and complete growth arrest; (2) reduction in the number of cancer or tumor cells; (3) reduction in tumor size; (4) inhibition (i.e., reduction, slowing down or complete stopping) of cancer cell infiltration into adjacent peripheral organs and/or tissues; and/or (5) inhibition (i.e. reduction, slowing down or complete stopping) of metastasis.

A cancer that "does not respond to a Notch1-specific antagonist" is a cancer that does not respond to treatment with a Notch1-specific antagonist (in the absence of any other Notch antagonist, i.e., a Notch2, Notch3 or Notch4 antagonist), or that would not respond to such treatment if given.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile.

An "effective amount" refers to an amount effective, at dosages and for periods of time necessary, to achieve the desired therapeutic or prophylactic result.

II. Embodiments of the Invention

The present invention relates, in part, to the characterization of different classes of T-ALL. One class of T-ALL is sensitive to treatment with GSI, which is a pan-Notch inhibitor, and is also sensitive to treatment with a Notch1-specific antagonist, indicating that Notch1 specifically drives this class of T-ALL. Another class of T-ALL is sensitive to treatment with GSI, but insensitive (i.e., resistant) to treatment with a Notch1-specific antagonist, indicating that an alternative or additional Notch receptor may drive this class of T-ALL. As shown herein, the inventors have discovered that this latter class of T-ALL is partially sensitive to treatment with a Notch3-specific antagonist, and even more sensitive to a combination of a Notch1-specific antagonist and a Notch3-specific antagonist. These results suggest a role for both Notch1 and Notch3 in leukemias, particularly T-cell and T-cell progenitor leukemias such as T-ALL.

A. Methods of Treatment

1. Treatment of Cancer with a Notch3-Specific Antagonist, Singly or in Combination with a Notch1-Specific Antagonist In various aspects of the invention, methods of treating a GSI-responsive cancer are provided, the method comprising administering to a patient having such cancer an effective amount of a Notch3-specific antagonist. In certain embodiments, the GSI-responsive cancer is leukemia. In certain embodiments, the GSI-responsive cancer does not respond to a Notch1-specific antagonist, e.g., the cancer has significantly increased levels of activated Notch3 and/or the cancer has absent or reduced levels of activated Notch1. In a further embodiment, the method further comprises administering an effective amount of a Notch1-specific antagonist. These and further aspects of the invention are described below.

In a particular aspect of the invention, a method of treating a GSI-responsive leukemia that does not respond to a Notch1-specific antagonist is provided, the method comprising administering to a patient having such leukemia an effective amount of a Notch3-specific antagonist.

A GSI-responsive leukemia may be identified by various ways. For example, a patient having leukemia may be treated with a GSI to determine whether or not the leukemia is GSI-responsive. Such a GSI may include any GSI that significantly inhibits Notch receptors. Such a GSI includes, but is not limited to, N—[N-(3,5-difluorophenacetyl)-L-alanyl]-S-phenylglycine t-butyl ester (DAPT); dibenzazepine; MK-0752 (Merck); the tripeptide z-Leu-Leu-Nle-CHO (Curry et al., Oncogene 24:6333-6344); and cbz-IL-CHO (Weijzen et al., Nat. Med. 8:979-986, 2002). It is noted, however, that a patient having leukemia need not have been treated with a GSI in order to determine whether the leukemia is GSI-responsive. Other methods may be employed. For example, leukemic cells removed from the patient may be assessed for cell proliferation or survival in the presence of a GSI, such as any of those listed above. In a further example, leukemic cells removed from the patient may be examined for increased Notch signaling by one or more Notch receptors, which would predict that the cells are GSI-responsive. For example, the cells may be assessed for the presence of a mutated, overexpressed, or activated Notch receptor. Methods similar to those described above may be used to determine whether any cancer is GSI-responsive.

A leukemia (e.g., a GSI-responsive leukemia) may be identified as one that does not respond to a Notch1-specific antagonist by various ways. For example, a patient having a leukemia may be treated with a Notch1-specific antagonist to determine whether or not the leukemia responds to the Notch1-specific antagonist. In certain embodiments, the Notch1-specific antagonist to which a leukemia does not respond is an anti-Notch1 antagonist antibody. In one such embodiment, the anti-Notch1 antagonist antibody is an antibody that binds to the extracellular domain of Notch1 and effects decreased Notch1 signaling. In one such embodiment, the anti-Notch1 antagonist antibody is an anti-Notch1 NRR antibody. Anti-Notch1 NRR antibodies include, but are not limited to, any of the anti-Notch1 NRR antibodies disclosed in U.S. Application Publication No. US 2009/0081238 A1, which is expressly incorporated by reference herein in its entirety. Such antibodies include, but are not limited to, anti-Notch1 NRR antibodies that bind to Notch1 NRR with an affinity of ≤0.1 µM; anti-Notch1 NRR antibodies that bind to LNR-A, LNR-B and HD-C of the Notch1 NRR; or a combination of the foregoing. Exemplary anti-Notch1 NRR antibodies include but are not limited to Antibodies A, A-1, A-2, and A-3 as described in US 2009/0081238 A1, or antibodies comprising the heavy and light chain variable region CDRs of an antibody selected from Antibody A, A-1, A-2, and A-3. In another such embodiment, an anti-Notch1 antagonist antibody is an anti-Notch1 antibody that binds to one or more EGF-like repeats of Notch1. Examples of such antibodies are described in International Publication No. WO 2008/091641. In certain embodiments, an anti-Notch1 antibody that binds to one or more EGF-like repeats of Notch1 effects decreased Notch1 signaling by significantly blocking binding of ligand to Notch1.

It is noted, however, that a patient having leukemia need not have been treated with a Notch1-specific antagonist in order to determine whether the leukemia is one that does not respond to a Notch1-specific antagonist. Other methods may be employed. For example, leukemic cells removed from the patient may be assessed for absent or reduced Notch1 activation, or in certain embodiments, the presence of wild-type Notch1, which would predict that the leukemia is one that does not respond to a Notch1-specific antagonist. For example, the cells may be assessed for absent or reduced Notch1 signaling by assessing absent or reduced transcription of Notch1 target genes, such as Hey1 and Hey2. In a further example, the cells may be assessed for absent or reduced Notch1 signaling by detecting absent or reduced levels of an activated form of Notch1, e.g., by using an antibody specific for activated Notch1 such as anti-active Notch1 Val1744 (commercially available from Cell Signaling Technologies). In certain embodiments, a suitable comparator cell (positive control) may be a leukemic cell that responds to a Notch1-specific antagonist, e.g., a leukemic cell in which the Notch1 pathway is activated. Such a comparator cell may include, e.g., a T-ALL cell in which Notch1 is known to be overexpressed, mutated (e.g., having a Notch1 activating mutation) or activated (e.g., constitutively activated), such as an HPB-ALL cell. If leukemic cells removed from a patient have absent or significantly reduced levels of activated Notch1 compared to the comparator cell, then the patient's leukemia is presumptively one that does not respond to a Notch1-specific antagonist.

Leukemic cells may also be assessed for activation of Notch3, indicating that the Notch3 pathway is activated and that the leukemia is therefore predicted to be one that does not respond to a Notch1-specific antagonist. In one embodiment, leukemic cells may be examined for the presence of overexpressed, mutated or activated Notch3. In certain embodiments, a suitable comparator cell (negative control) for purposes of assessing Notch3 activation status may be a leukemic cell that responds to a Notch1-specific antagonist, e.g., a leukemic cell in which the Notch1 pathway is activated. Such a comparator cell may include, e.g., a T-ALL cell in which Notch1 is known to be overexpressed, mutated or activated such as an HPB-ALL cell. In such a cell, Notch3 is not expected to be significantly activated. Therefore, if leukemic cells removed from a patient have significantly increased levels of activated Notch3 compared to the comparator cell, then the patient's leukemia is presumptively one that does not respond to a Notch1-specific antagonist. In certain other embodiments, a suitable comparator cell (positive control) may be a leukemic cell in which Notch3 is known to be overexpressed, mutated or activated, such as a TALL-1 cell. In such a cell, Notch3 is expected to have significantly increased levels of activated Notch3. Therefore, if leukemic cells removed from a patient have comparable levels of activated Notch3 compared to the comparator cell, then the patient's leukemia is presumptively one that does not respond to a Notch1-specific antagonist. Methods similar to those described above can be used to determine whether any cancer is one that does not respond to a Notch1-specific antagonist.

A useful tool for assessing Notch3 activation status is the new anti-Notch3 ICD antibody described in the Examples, which binds to activated Notch3 ICD.

In certain embodiments, the Notch3-specific antagonist that is administered is an anti-Notch3 antagonist antibody. In one such embodiment, the anti-Notch3 antagonist antibody is an antibody that binds to the extracellular domain of Notch3 and effects decreased Notch3 signaling. In one such embodiment, the anti-Notch3 antagonist antibody is an anti-Notch3 NRR antibody. Anti-Notch3 NRR antibodies include, but are not limited to, any of the anti-Notch3 NRR antibodies disclosed in U.S. Patent Application Publication No. US 2008/0226621 A1, which is expressly incorporated by reference herein in its entirety. Such antibodies include, but are not limited to anti-Notch3 NRR antibodies that bind to the LNR-A and HD-C domains of Notch3 NRR. Exemplary anti-Notch3 NRR antibodies are monoclonal antibodies 256A-4 and 256A-8, as described in US 2008/0226621 A1, and humanized forms thereof, as well as anti-Notch3 NRR antibodies comprising the heavy and light chain variable region CDRs of antibody 256A-4 or 256A-8. In another such embodiment, an anti-Notch3 antagonist antibody is an anti-Notch3 antibody that binds to one or more EGF-like repeats of Notch3. Examples of such antibodies are described in Li et al., *J. Biol. Chem.* 283:8046-8054, 2008. In certain embodiments, an anti-Notch3 antibody that binds to one or more EGF-like repeats of Notch3 effects decreased Notch3 signaling by significantly blocking binding of ligand to Notch3.

In certain embodiments, a leukemia is a T-cell leukemia. In certain such embodiments, a T-cell leukemia is a T-cell progenitor leukemia. In certain such embodiments, a T-cell progenitor leukemia is T-ALL.

In further embodiments, a method of treating a GSI-responsive cancer that does not respond to a Notch1-specific antagonist is provided, the method comprising administering to a patient having such cancer an effective amount of a Notch3-specific antagonist, and further comprising administering to such patient an effective amount of a Notch-1 specific antagonist. In certain embodiments, the GSI-responsive cancer is a GSI-responsive leukemia. In certain embodiments, the Notch1-specific antagonist to be administered is an anti-Notch1 antagonist antibody. In one such embodiment, the anti-Notch1 antagonist antibody is an antibody that binds to the extracellular domain of Notch1 and effects decreased Notch1 signaling. In one such embodiment, the anti-Notch1 antagonist antibody is an anti-Notch1 NRR antibody. Anti-Notch1 NRR antibodies include, but are not limited to, any of the anti-Notch1 NRR antibodies disclosed in U.S. Application Publication No. US 2009/0081238 A1, which is expressly incorporated by reference herein. Such antibodies include, but are not limited to, anti-Notch1 NRR antibodies that bind to Notch1 NRR with an affinity of ≤0.1 μM; anti-Notch1 NRR antibodies that bind to LNR-A, LNR-B and HD-C of the Notch1 NRR; or a combination of the foregoing. Exemplary anti-Notch1 NRR antibodies include but are not limited to Antibodies A, A-1, A-2, and A-3 as described in US 2009/0081238 A1, or antibodies comprising the heavy and light chain variable region CDRs of an antibody selected from Antibody A, A-1, A-2, and A-3. In another such embodiment, the anti-Notch1 antagonist antibody is an anti-Notch1 antibody that binds to one or more EGF-like repeats of Notch1. Examples of such antibodies are described in International Publication No. WO 2008/091641. In certain embodiments, an anti-Notch1 antibody that binds to one or more EGF-like repeats of Notch1 effects decreased Notch1 signaling by significantly blocking binding of ligand to Notch1.

2. Treatment of Leukemia with a Notch1-Specific Antagonist

Further aspects of the invention are based, in part, on the identification of a class of T-ALL that is responsive to GSI and is also responsive to a Notch1-specific antagonist, but is not responsive to a Notch3-specific antagonist, indicating that Notch1 drives the T-ALL. In various aspects of the invention, methods of treating a GSI-responsive cancer are provided, the method comprising administering to a patient having such cancer an effective amount of a Notch1-specific antagonist. In certain embodiments, the GSI-responsive cancer is leukemia. In certain embodiments, the GSI-responsive cancer does not respond to a Notch3-specific antagonist, e.g., the cancer has absent or reduced levels of activated Notch3 (e.g., as compared to a comparator cell that responds to a Notch3-specific antagonist) and/or has significantly increased levels of activated Notch1 (e.g., as compared to a comparator cell that does not respond to a Notch1-specific antagonist).

In certain embodiments, the leukemia belongs to a class of leukemias characterized by sensitivity to GSI and sensitivity to a Notch1-specific antagonist. In one embodiment, the leukemia is a T-cell leukemia. In one such embodiment, the T-cell leukemia is a T-cell progenitor leukemia. In one such embodiment, the T-cell leukemia is T-ALL. In another embodiment, the leukemia is characterized by a Notch1 activating mutation.

In certain embodiments, a Notch1-specific antagonist is any of those provided above. In further embodiments, a Notch3-specific antagonist is any of those provided above.

B. Compositions and Diagnostic Methods

The invention further provides an antibody that binds activated human Notch3 ICD. In one embodiment, the antibody binds to the peptide sequence VMVARRKREHSTLW (SEQ ID NO:4). In one embodiment, the antibody is monoclonal. In one embodiment, the antibody is polyclonal. The above embodiments may be present alone or in combination.

Such an antibody is useful in diagnostic methods, e.g., to identify patient populations suitable for treatment with a Notch3-specific antagonist, as described above. Accordingly, in certain embodiments, a method of identifying a cancer suitable for treatment with an antagonist of Notch3 is provided, the method comprising determining whether Notch3 is activated in the cancer. In one embodiment, the cancer is a GSI-responsive cancer. In another embodiment, the cancer is a leukemia. In another embodiment, the leukemia is a T-cell leukemia. In one such embodiment, the T-cell leukemia is a T-cell progenitor leukemia. In one such embodiment, the T-cell leukemia is T-ALL.

In further embodiments, determining whether Notch3 is activated in the cancer comprises contacting a sample of the cancer with an antibody that binds activated Notch3 ICD, and determining whether significantly increased levels of activated Notch3 (as reflected by levels of activated Notch3 ICD) are present, wherein the presence of significantly increased levels of activated Notch3 indicates that the cancer is suitable for treatment with an antagonist of Notch3. To determine whether significantly increased levels of activated Notch3 are present in the sample, an appropriate comparator (positive control) may be, e.g., a sample from a cancer known to respond to an antagonist of Notch3. If the "test" sample and the "control" sample contain comparable levels of activated Notch3, then the cancer from which the "test" sample was obtained is suitable for treatment with an antagonist of Notch3. Another appropriate comparator (negative control) may be, e.g., a sample from a cancer that does not respond to an antagonist of Notch3. If the "test" sample contains significantly increased levels of activated Notch3 compared to the control sample, then the cancer from which the "test" sample was obtained is suitable for treatment with an antagonist of Notch3.

In certain embodiments of the above methods, an antagonist of Notch3 is a Notch3-specific antagonist. In certain embodiments, a Notch3-specific antagonist is any of those discussed above.

III. Examples

A. T-ALL Falls into Three Classes

Previous studies have shown that T-ALL cell lines may be sensitive or insensitive to treatment with GSI. For example, certain T-ALL cell lines are resistant to GSI despite expression of activating Notch1 mutations, possibly due to activation of a non-Notch pathway, e.g., a pathway that circumvents the need for Notch. (See, e.g., Palomero et al., *Nat. Med.* 13:1203-1210, 2007.) However, in one study, five of thirty T-ALL cell lines were GSI-sensitive, showing cell cycle arrest in response to GSI. (See Weng et al., *Science,* 306:269-271, 2004.) The studies reported below further explored the response of T-ALL cell lines not only to GSI, but also to Notch1- and Notch3-specific antagonists.

Three classes of T-ALL were characterized based on their sensitivity to GSI and to a Notch1-specific antagonist. The Notch1-specific antagonist used in the following studies was the anti-Notch1 NRR antibody, "Antibody A-2," the isolation and characterization of which are discussed in U.S. Patent Application Publication No. US 2009/0081238 A1. For convenience, "Antibody A-2" is referred to herein as "anti-NRR1," and is also referred to as "α-Notch1," "aNotch1," or "α-N1" in the figures.

FIGS. 3-5 presents the classification of three representative human T-ALL cell lines. Those cell lines include the P-12 Ichikawa cell line, the HPB-ALL cell line, and the TALL-1 cell line. The cells were grown for eight days in control conditions (DMSO alone (the vehicle for DAPT) or anti-gD (an isotype control antibody)); in the presence of the gamma-secretase inhibitor, DAPT (5 µM); or in the presence of anti-NRR1 (5 µg/ml). The cells were fixed, stained with propidium iodide and prepared for FACS to analyze the cell cycle status, according to standard procedures. Growth sensitivity was assessed by examining whether a given treatment caused an increase in the percentage of cells in G0/G1 with a corresponding decrease in the percentage of cells in S/G2/M. The results show that P-12 Ichikawa cells are resistant to both DAPT and anti-NRR1 (FIG. 3A-3D), with no significant difference in cell cycle status among DAPT-treated, anti-NRR1-treated, and control (DMSO- and anti-gD-treated) cells. HPB-ALL cells are sensitive to both DAPT and anti-NRR1 (FIG. 4A-4D), with DAPT- and anti-NRR1-treated cells showing about 78% and 76% of cells in G0/G1, respectively, compared to about 33-34% of the control cells. TALL-1 cells are sensitive to DAPT but resistant to anti-NRR1 (FIG. 5A-5D), with about 87% of DAPT-treated cells in G0/G1, compared to about 55% of anti-NRR1-treated cells and about 53-54% of control cells. It is noted that Notch1 is not mutated in TALL-1 cells. Further studies revealed that a fourth cell line, CCRF-CEM, fell into the same class as P-12 Ichikawa cells (i.e., resistant to both GSI and anti-NRR1). (Data not shown and FIG. 10.)

Figure 6:
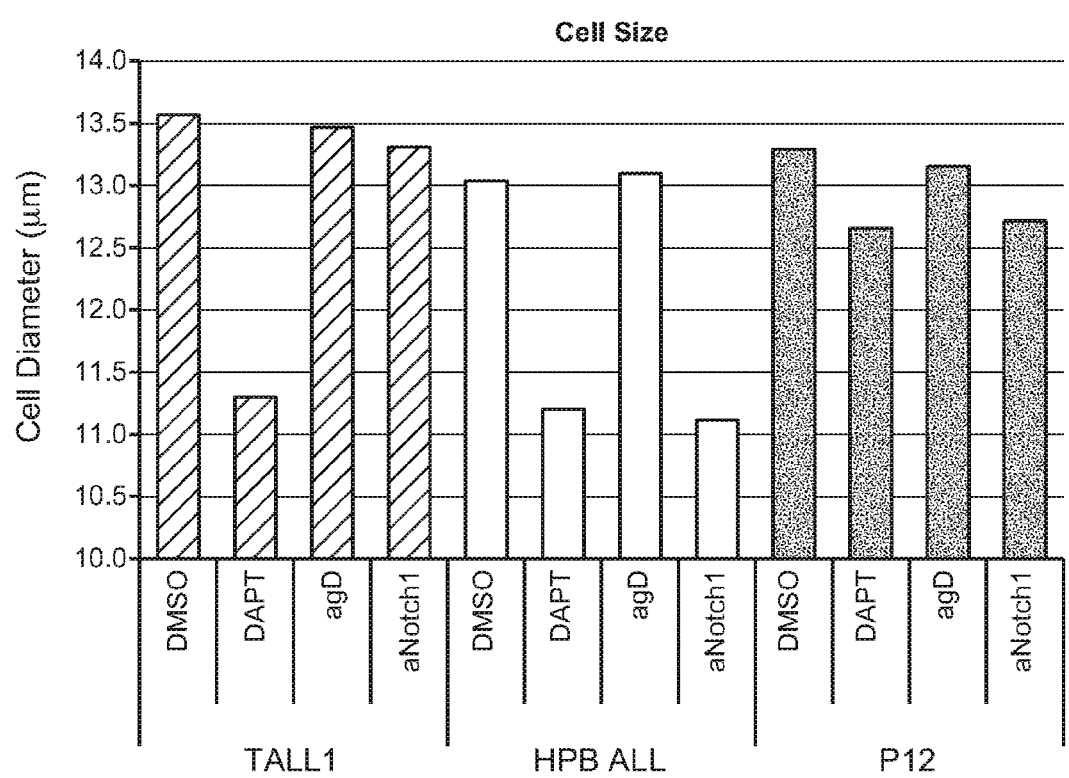
FIG. 6 shows that cell size measurements reflect the three classes of T-ALL identified in FIGS. 3-5.

As shown in FIG. 6, cell size measurements reflect these three classes of T-ALL. The P-12 Ichikawa cell line, the HPB-ALL cell line, and the TALL-1 cell line were grown for approximately one week in control conditions (DMSO alone (the vehicle for DAPT) or anti-gD (an isotype control antibody)); in the presence of the gamma-secretase inhibitor, DAPT (5 μM); or in the presence of anti-NRR1 (5 μg/ml). Cell diameter was measured using a cell counter (Vi-Cell, Beckman Coulter). Consistent with the growth inhibition studies, the P-12 Ichikawa line is resistant to both DAPT and anti-NRR1, as indicated by relatively consistent cell diameter among treated and control cells. HPB-ALL is sensitive to both DAPT and anti-NRR1, as indicated by the significantly smaller size of cells treated with those agents, respectively. TALL-1 is sensitive to DAPT but resistant to anti-NRR1, as indicated by the significantly smaller size of cells treated with DAPT but not with anti-NRR1 or control agents. These results are consistent with the growth studies described above.

Figure 7:
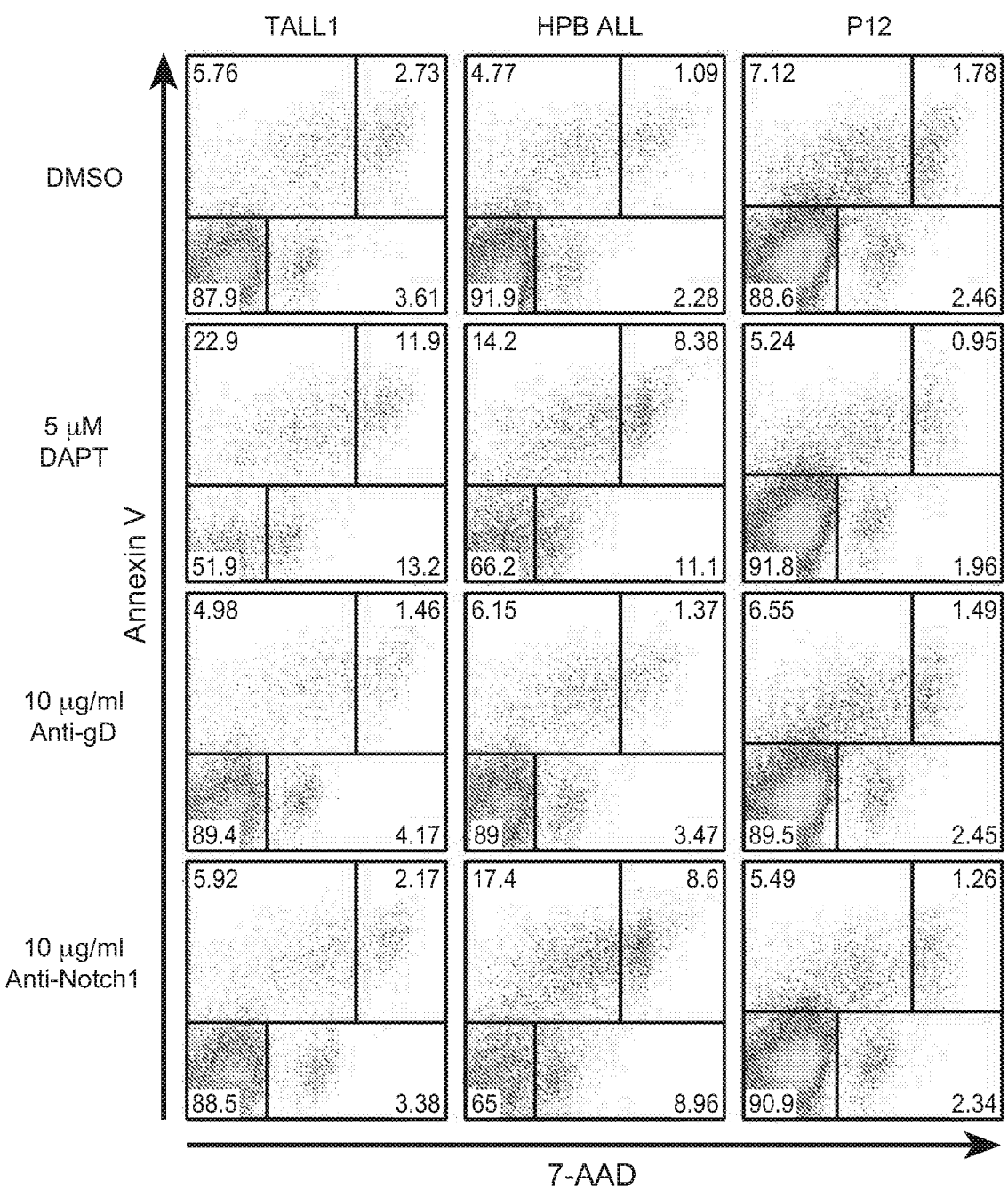
FIG. 7 shows that staining with Annexin V (marker for apoptosis) and 7-AAD (marker for cell death) reflects the three classes of T-ALL identified in FIGS. 3-5.

As shown in FIG. 7, apoptosis measurements also reflect these three classes of T-ALL. The P-12 Ichikawa cell line, the HPB-ALL cell line, and the TALL-1 cell line were treated as described above for FIG. 6. The cells were analyzed by FACS, with staining for 7-AAD (cell death marker) on the x-axis of FIG. 7, and staining for Annexin V (marker for apoptosis) on the y-axis of FIG. 7. Based on the percentage of cells in the double positive population, treatment with either DAPT or anti-NRR1 increases apoptotic cell death in HPB-ALL cells. In contrast, P-12 Ichikawa cells are resistant to both treatments, whereas TALL-1 cells are sensitive to DAPT but not to anti-NRR1. These results are consistent with the growth studies and cell diameter measurements described above.

Figure 8:
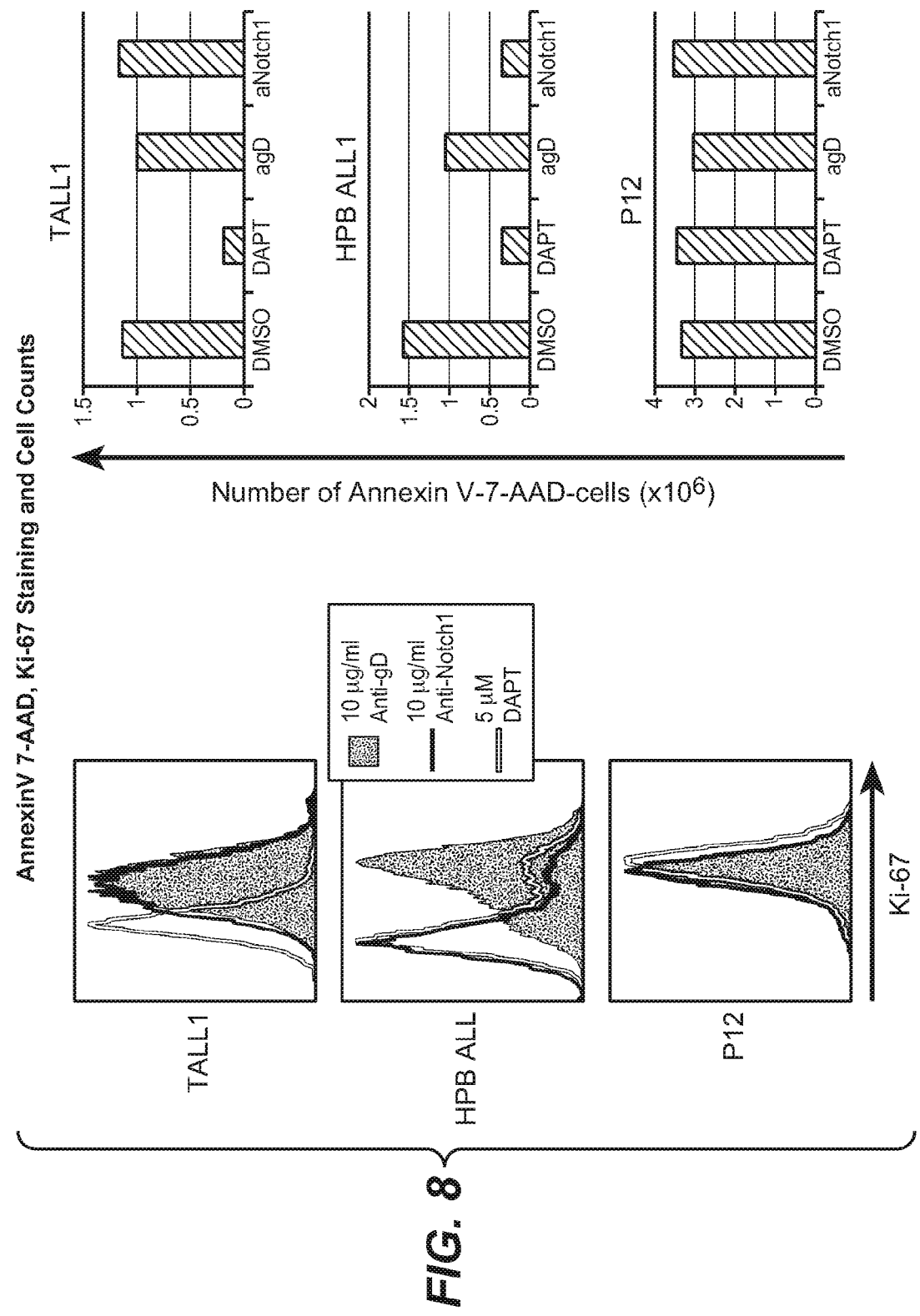
FIG. 8, left panel, shows that Ki-67 staining (marker for cell proliferation) reflects the three classes of T-ALL identified in FIGS. 3-5. Left-shifted peaks indicate lower staining for Ki-67 and decreased proliferation relative to right-shifted peaks.
Figure 9A:
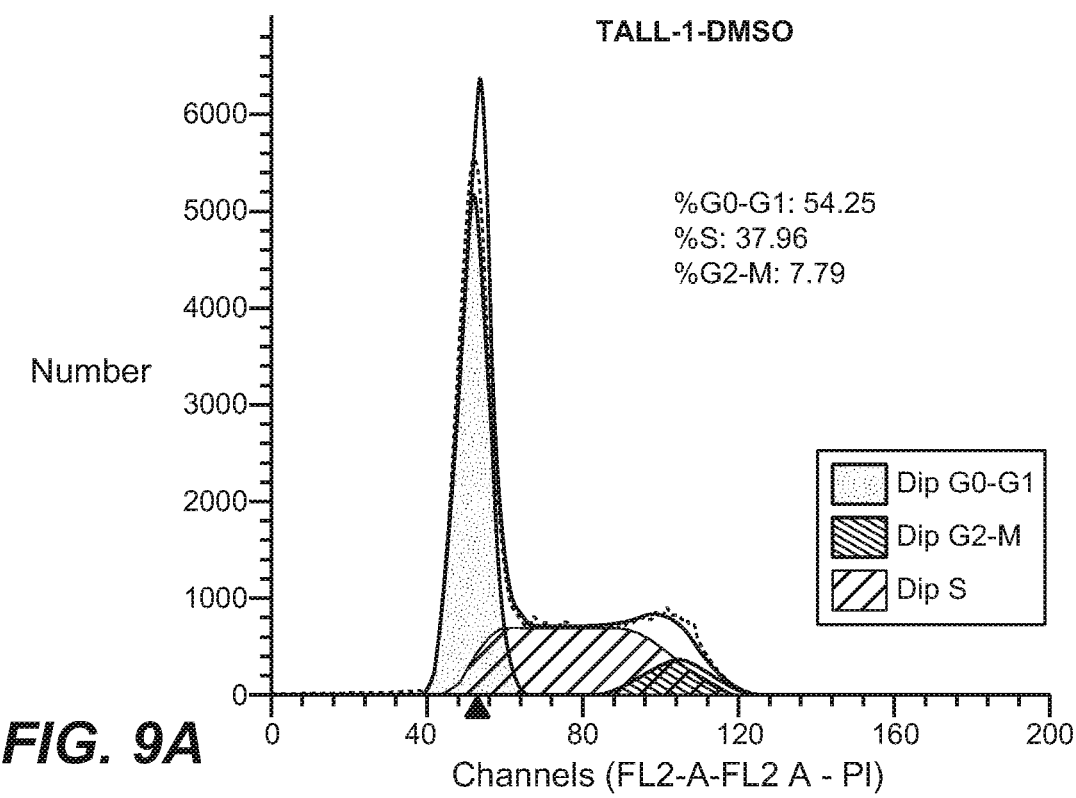
FIG. 9A-9F shows that the TALL-1 cell line is partially sensitive to anti-NRR3 (α-N3) and sensitive to treatment with anti-NRR1 (α-N1) and anti-NRR3.
Figure 9B:
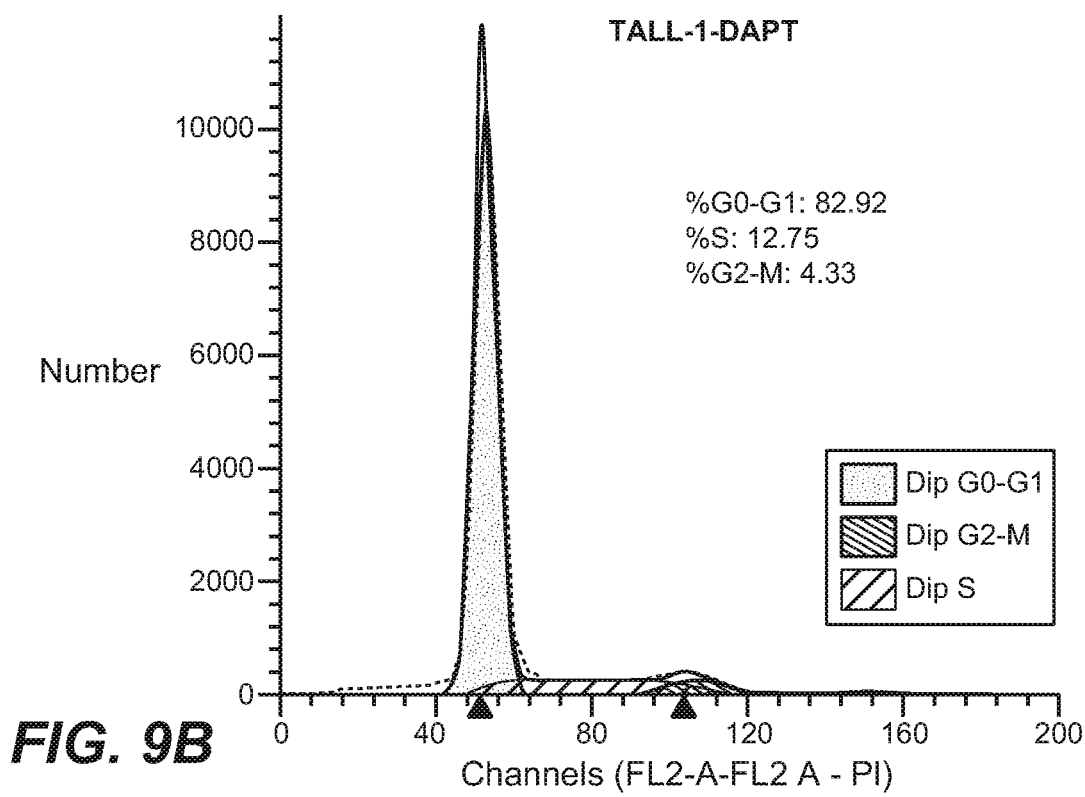
Figure 9C:
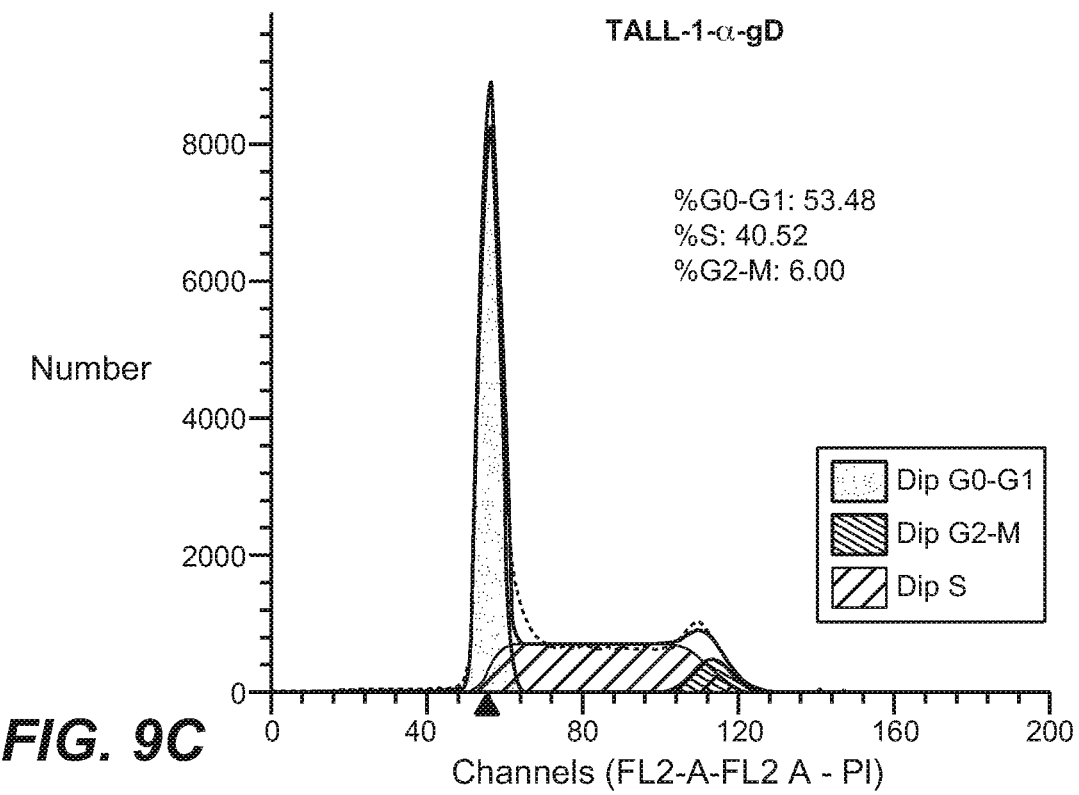
Figure 9D:
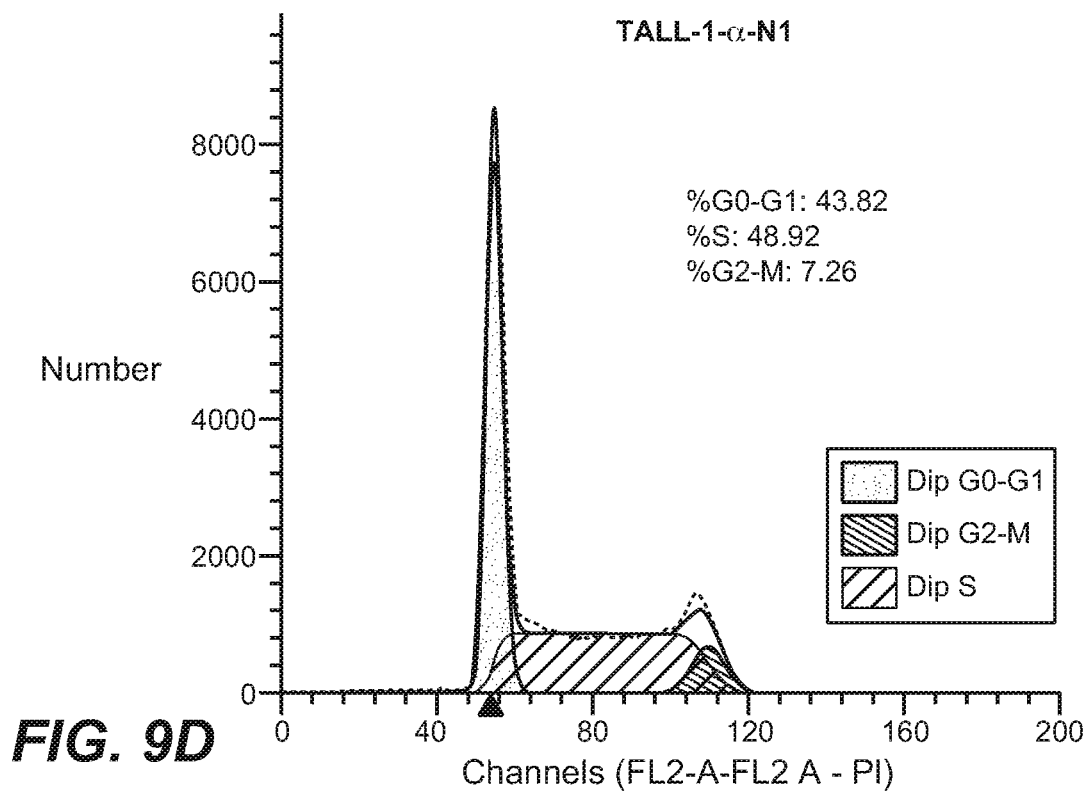
Figure 9E:
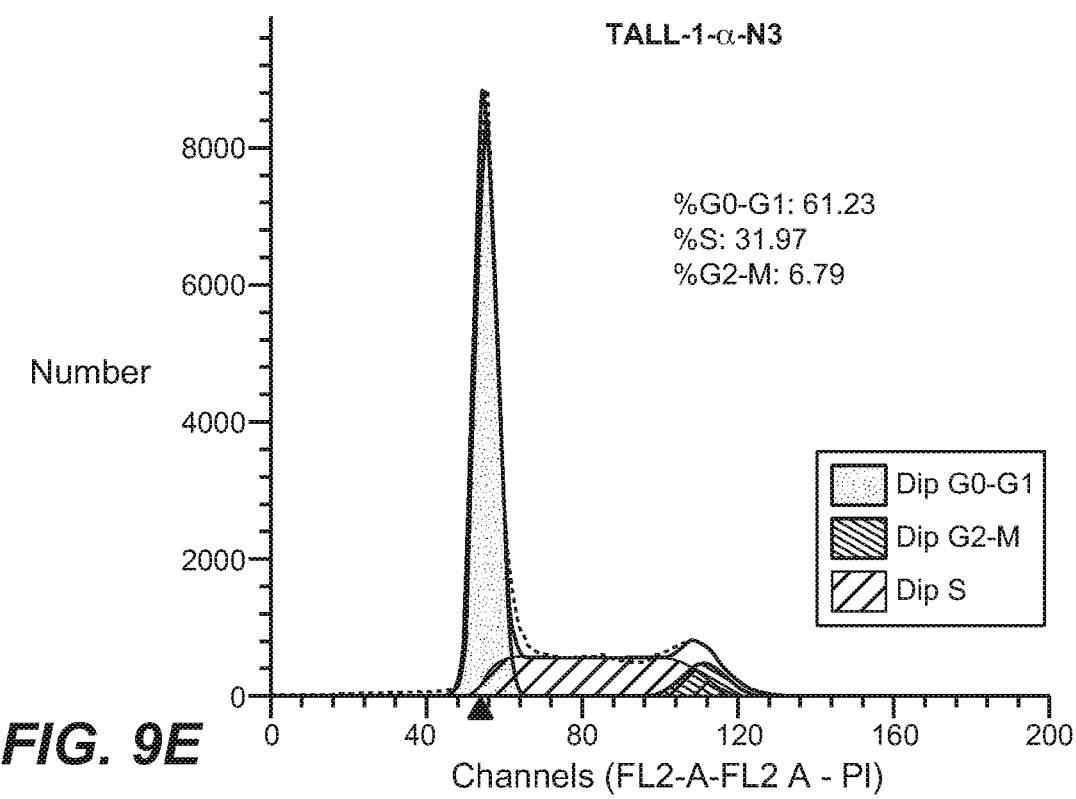
Figure 9F:
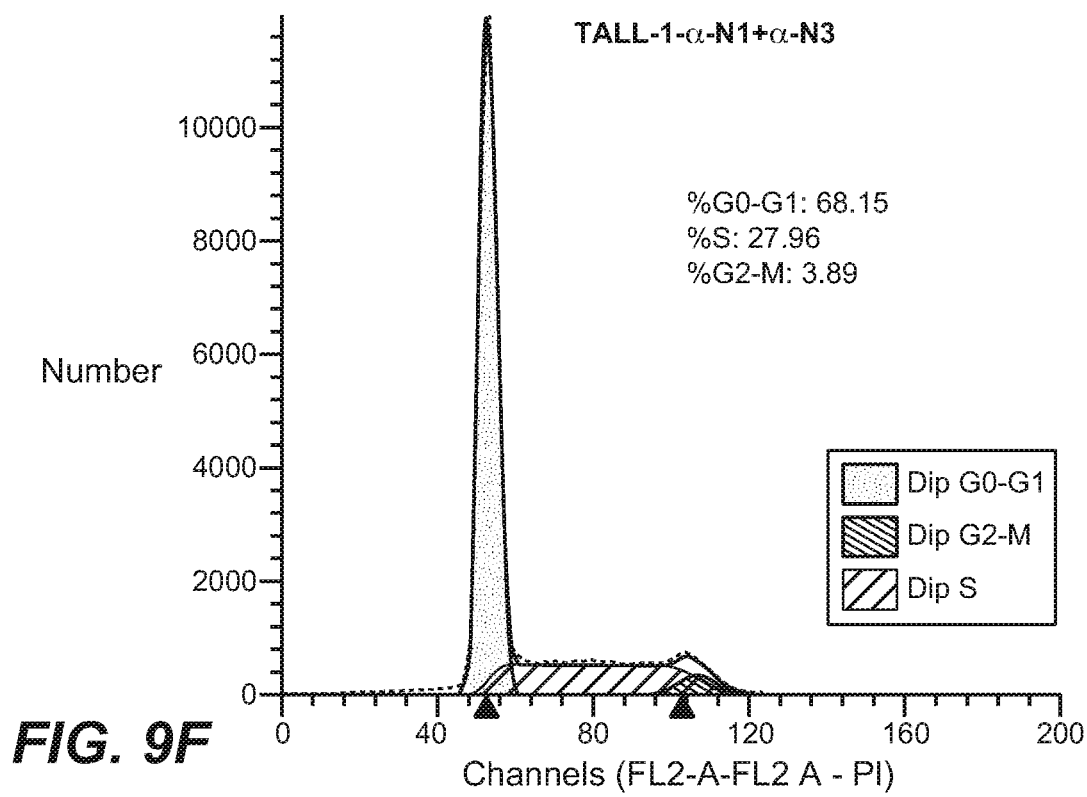
Figure 10A:
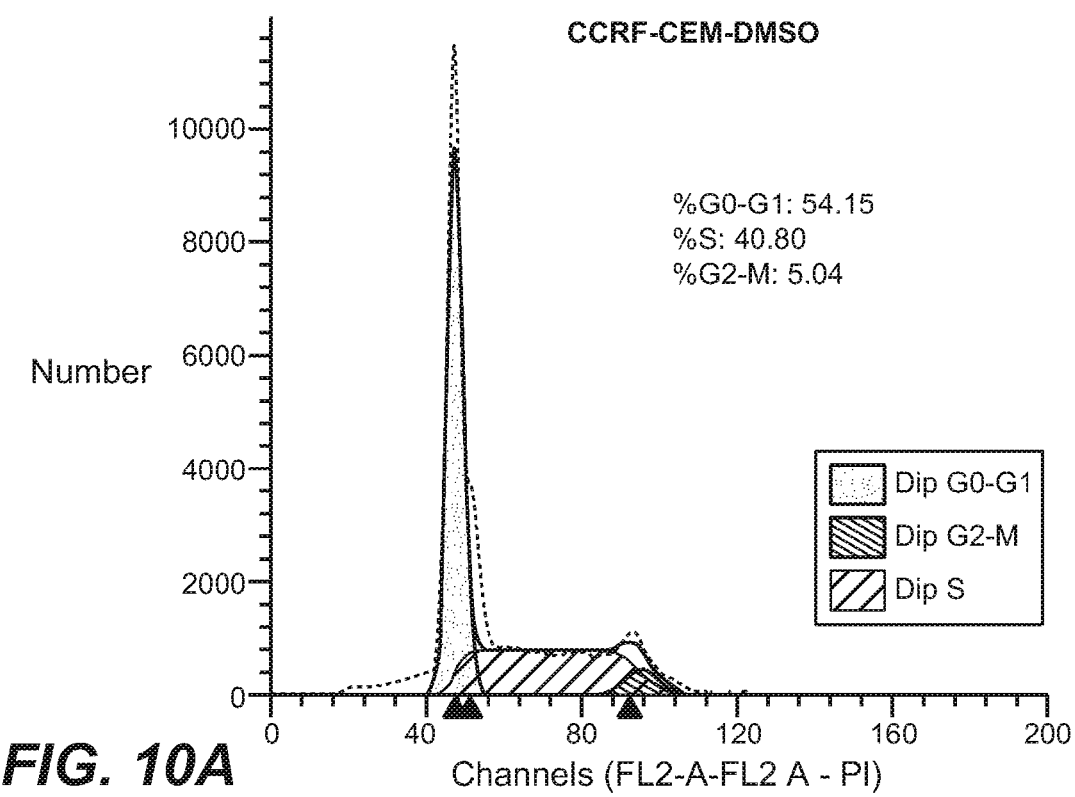
FIG. 10A-10F shows that the T-ALL cell line, CCRF-CEM, is resistant to both GSI, anti-NRR1 (α-N1) and anti-NRR3 (α-N3).
Figure 10B:
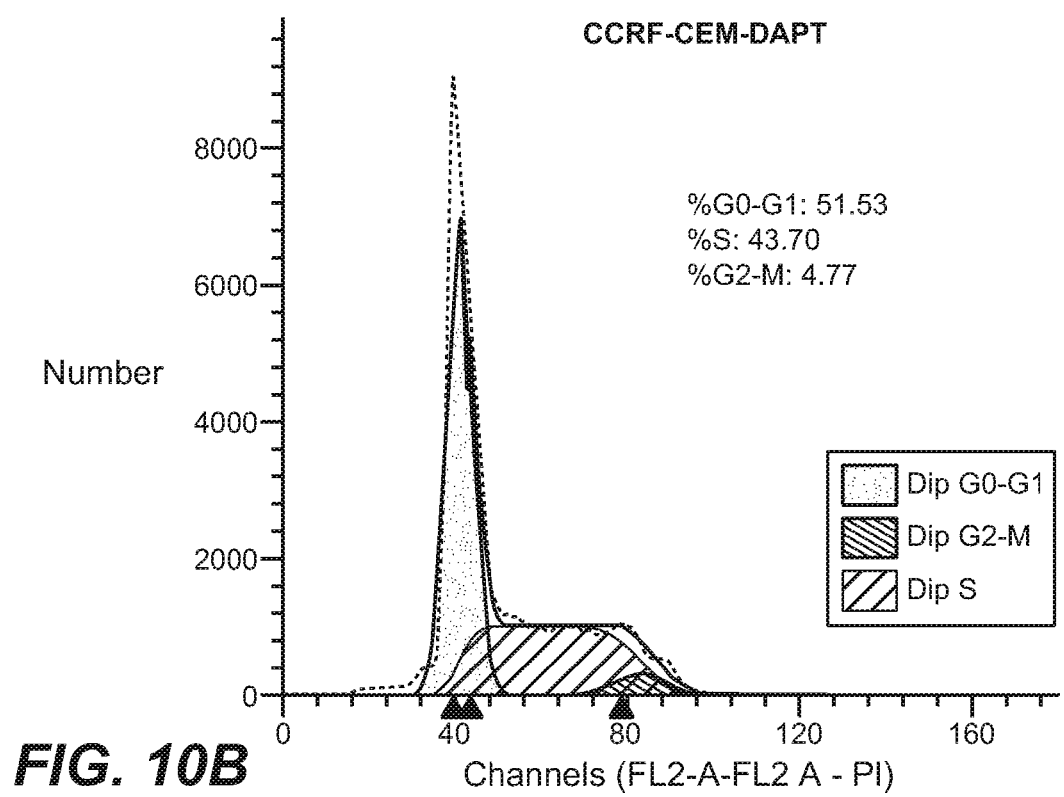
Figure 10C:
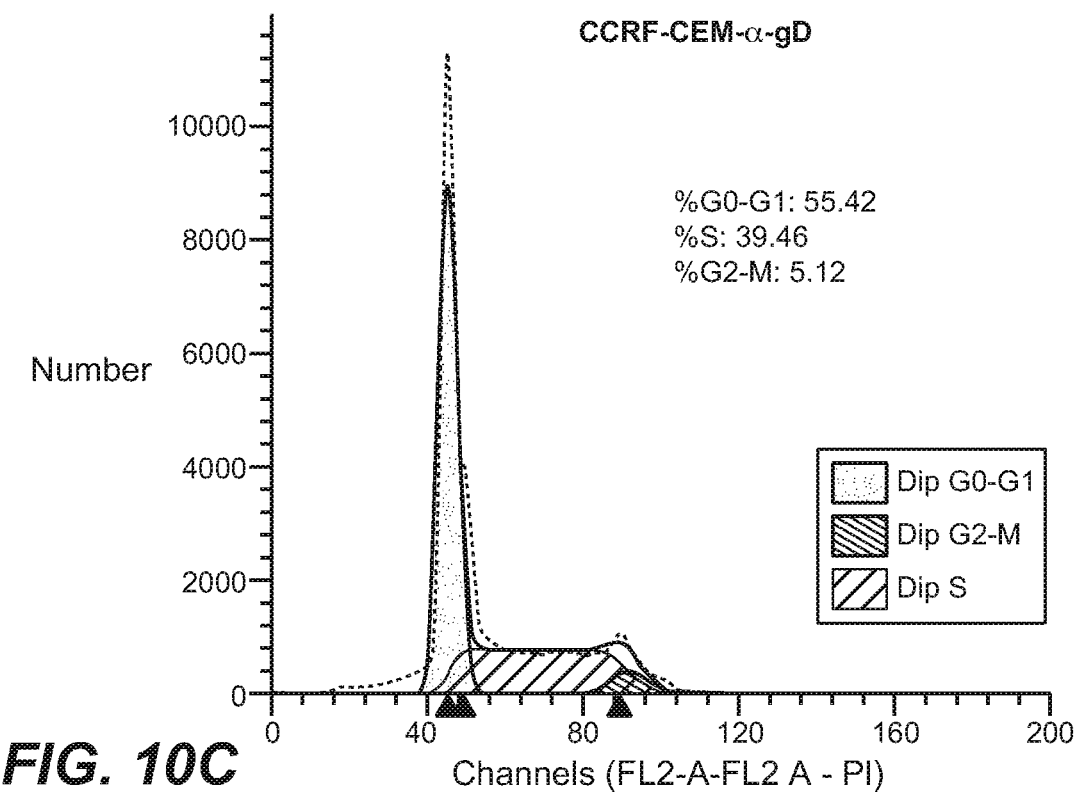
Figure 10D:
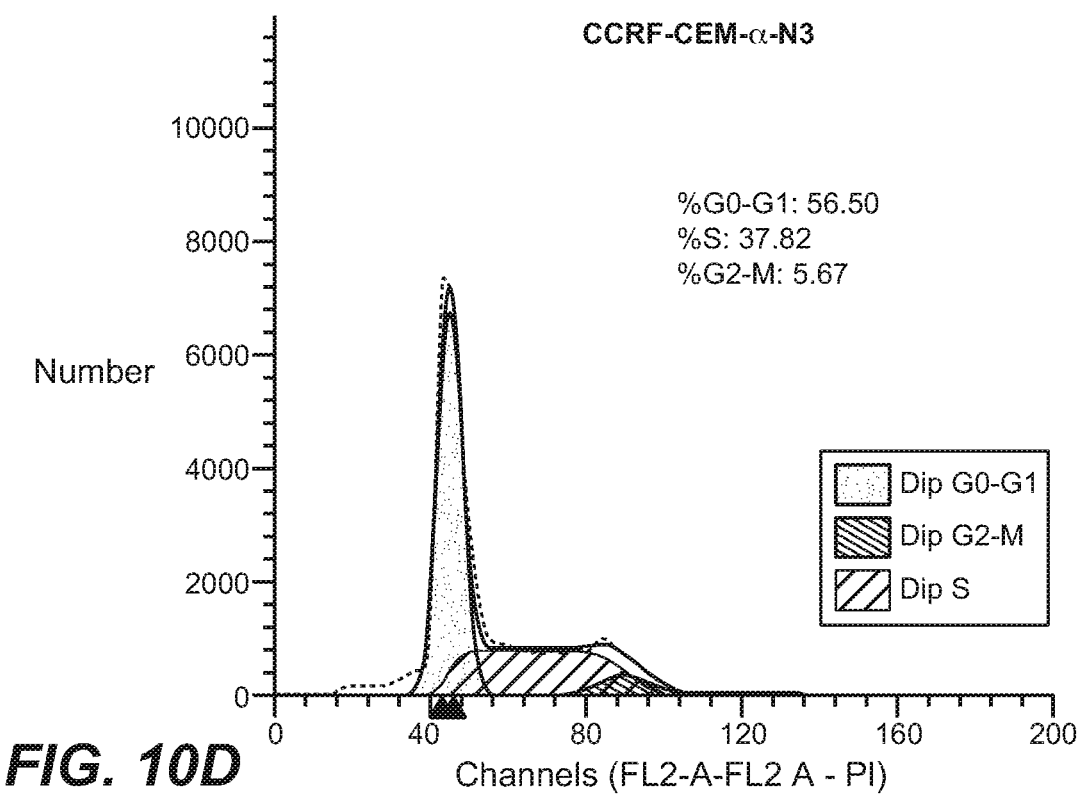
Figure 10E:
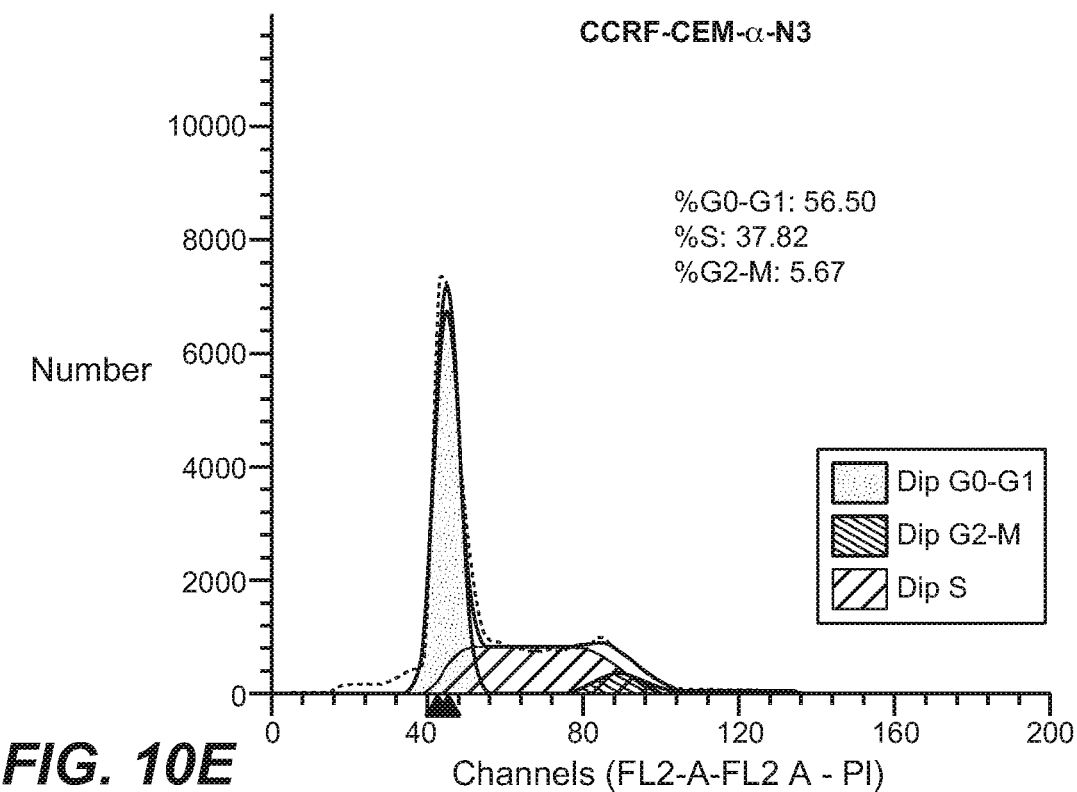
Figure 10F:
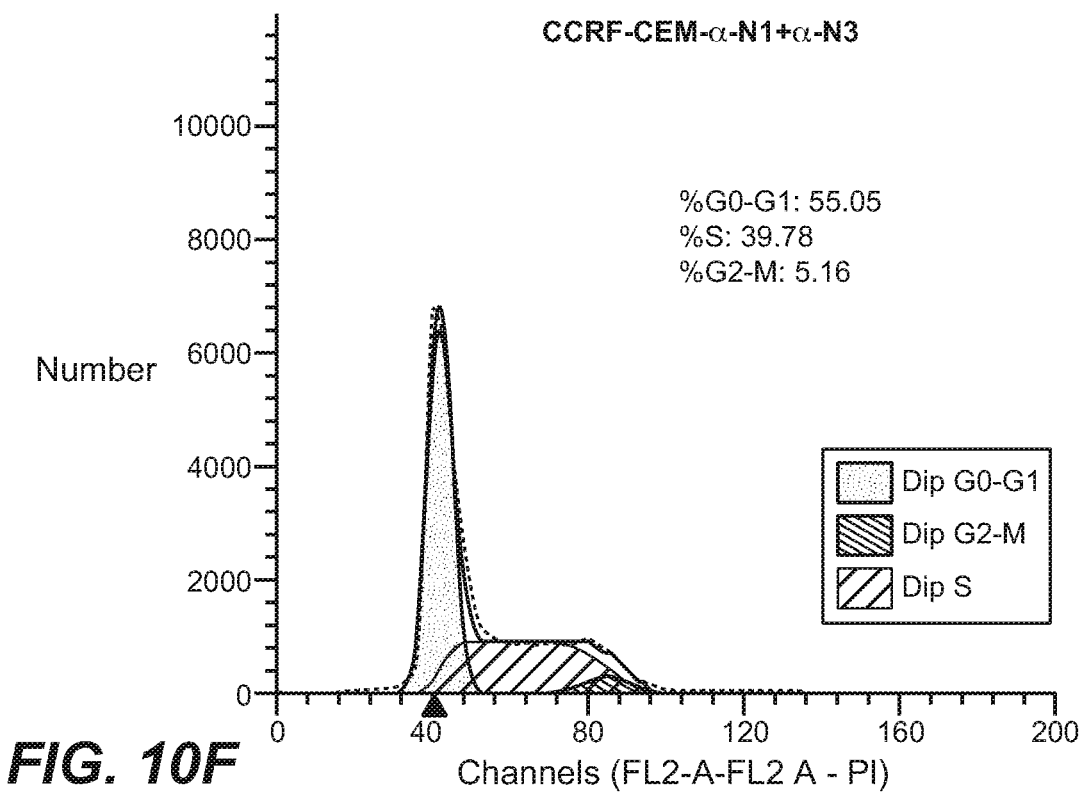
Figure 11A:
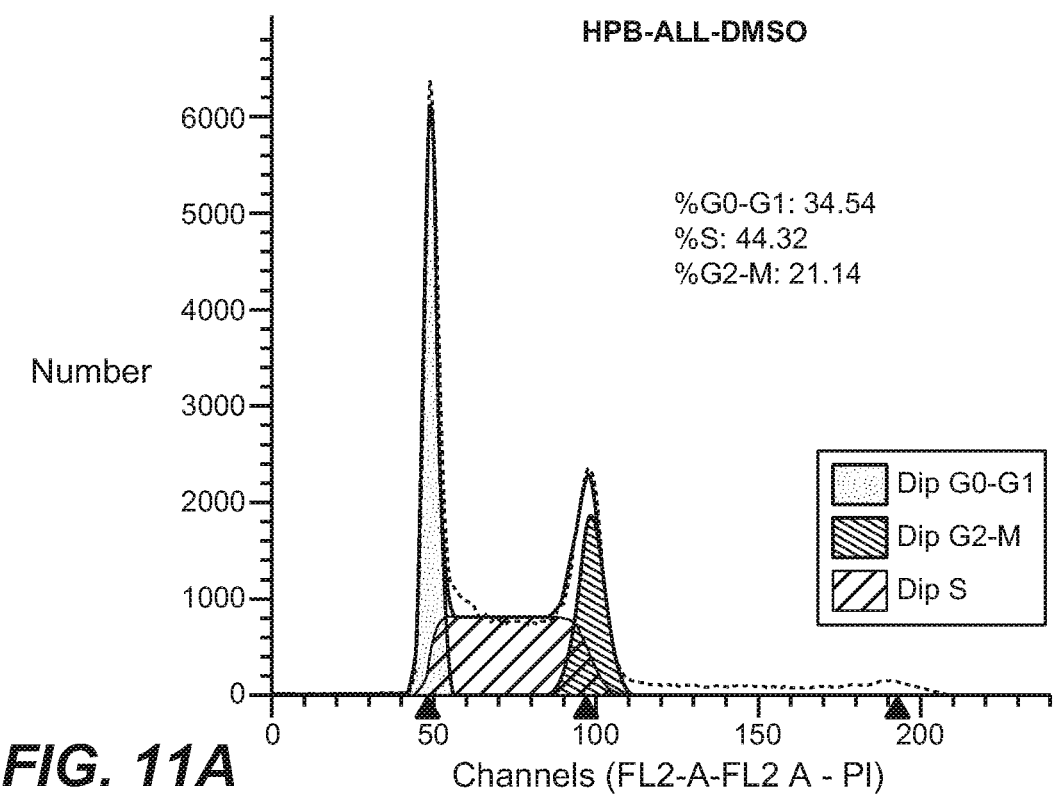
FIG. 11A-11F shows that the HPB-ALL cell line is sensitive to anti-NRR1 (α-N1) but not anti-NRR3 (α-N3).
Figure 11B:
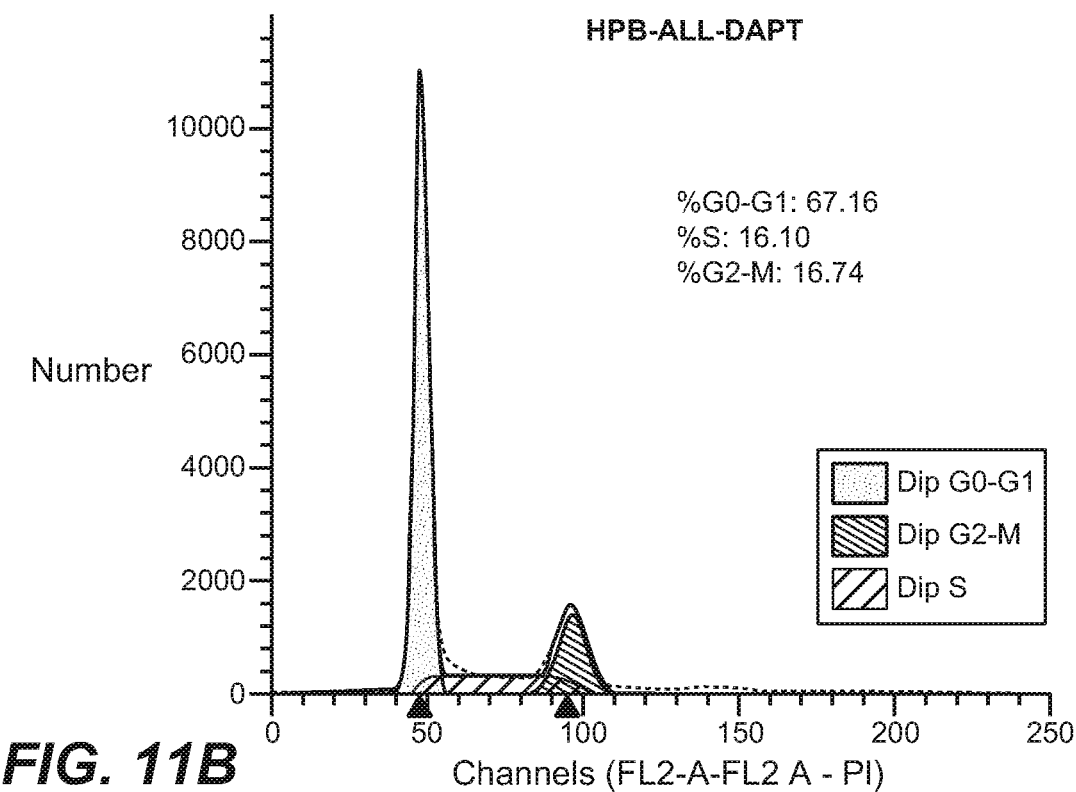
Figure 11C:
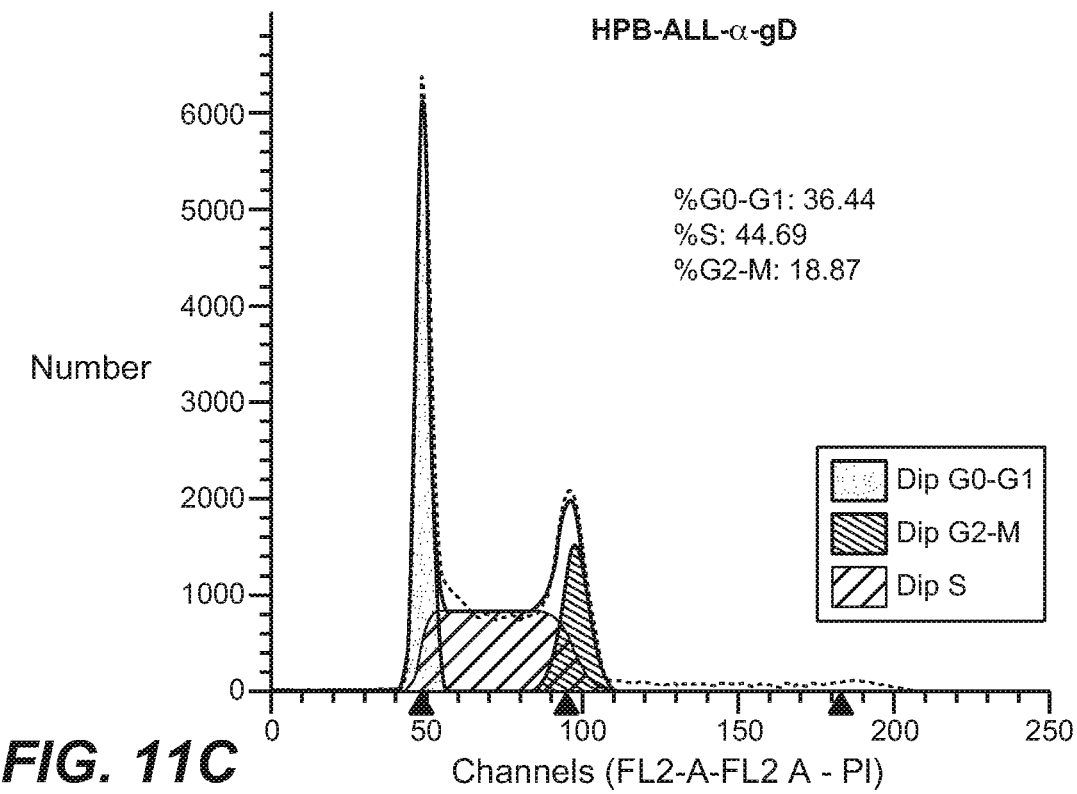
Figure 11D:
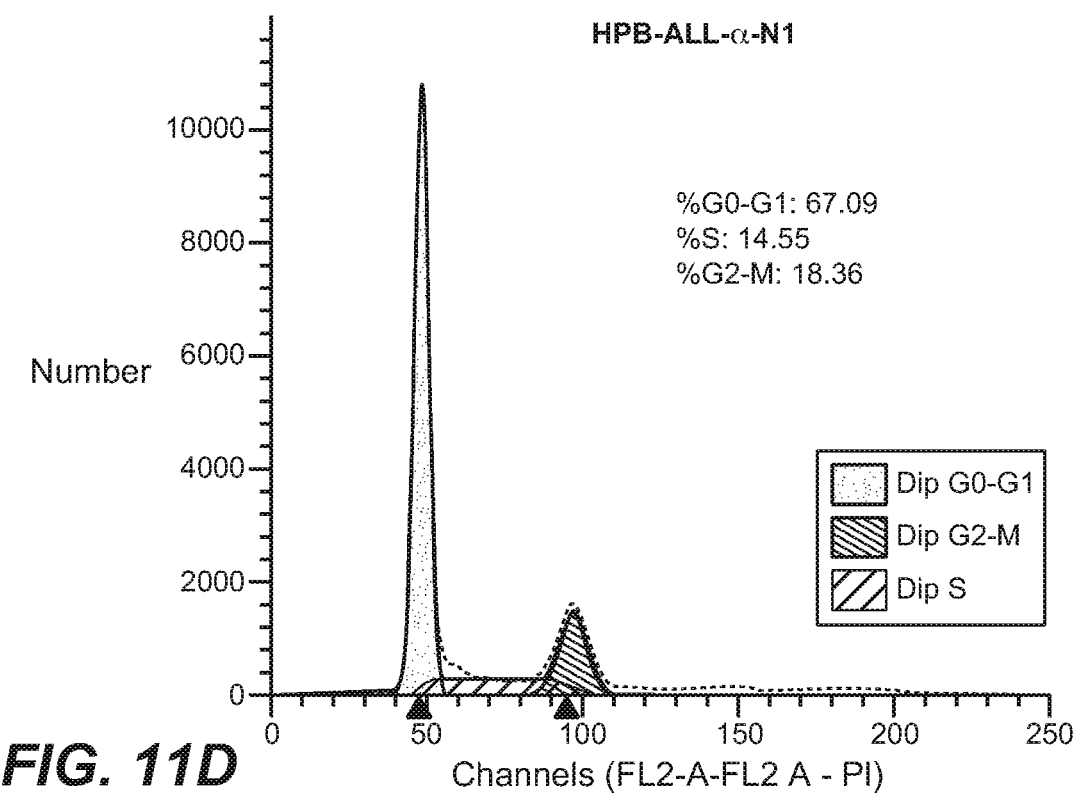
Figure 11E:
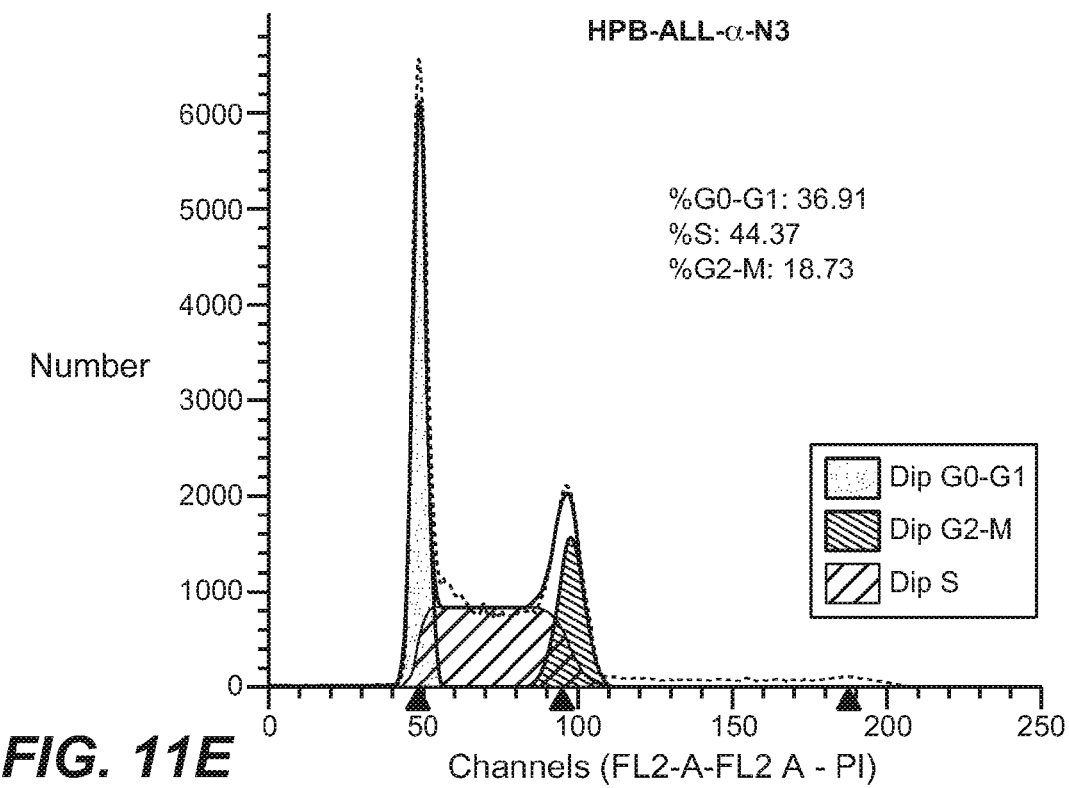
Figure 11F:
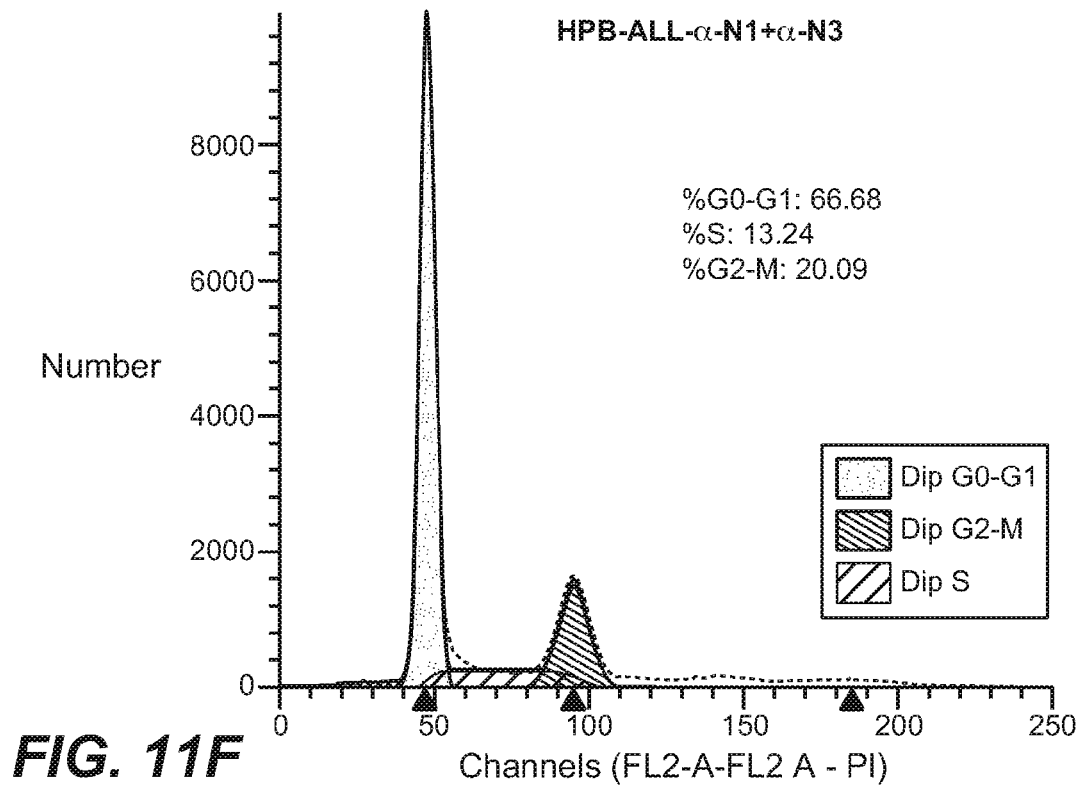

As shown in FIG. 8, the results of a cell proliferation assay also reflect these three classes of T-ALL. The P-12 Ichikawa cell line, the HPB-ALL cell line, and the TALL-1 cell line were treated as described above for FIG. 6. The cells were analyzed by FACS using Ki-67 staining to mark proliferation (left panel). A shift in the FACS peak to the left indicates lower staining for Ki-67 and decreased proliferation, and conversely, a shift in the FACS peak to the right indicates higher staining for Ki-67 and increased proliferation. Based on this proliferation assay, HPB-ALL was sensitive to both DAPT and anti-NRR1, TALL-1 was sensitive to DAPT but not anti-NRR1, and P-12 Ichikawa cells were resistant to both. Again, these results are consistent with those from the other assays described above, as well as apoptosis measurements shown in the right panel of FIG. 8. That panel shows cell counts for Annexin V/7-AAD double negative (non-apoptotic) cells. Low cell counts (i.e., low numbers of Annexin V/7-AAD double negative (non-apoptotic) cells) indicate increased apoptosis, which in turn correlate with decreased proliferation in the left hand panel.

B. GSI-Responsive, Anti-NRR1 Resistant TALL-1 Cells are Partially Sensitive to Anti-NRR3

As described above, two of the three classes of T-ALL, represented by HPB-ALL and TALL-1, are both sensitive to GSI but differ in that the former is sensitive to anti-NRR1, whereas the latter is not. Because sensitivity to GSI suggests a role for one or more Notch receptors, we asked whether a Notch receptor in addition to or in the alternative to Notch1 plays a role in the resistance of the latter class of T-ALL to anti-Notch1 NRR. To address this question, CCRF-CEM cells, HPB-ALL cells, and TALL-1 cells were treated as described for FIGS. 3-5, except that a Notch3-specific antagonist was also included at 10 μg/ml in a subset of the treatments to test whether growth depended on Notch3 signaling. The Notch3-specific antagonist used in these studies was mouse anti-human Notch3 monoclonal antibody 256A-4, the isolation and characterization of which are discussed in U.S. Patent Application Publication No. US 2008/0226621 A1. For convenience, 256A-4 is referred to herein as "anti-NRR3," and is also referred to as "α-N3" in the figures.

The results indicate that growth of TALL-1 is partially sensitive to anti-NRR3 and even more sensitive to anti-NRR1 plus anti-NRR3 (see FIG. 9A-9F), suggesting that signaling through Notch3 as well as Notch1 explains why the line is sensitive to DAPT but not to anti-NRR1. Specifically, nearly 83% of TALL-1 cells were in G0/G1 after DAPT treatment, compared to about 53-54% for the control (DMSO- or α-gD-treated) cells. Treatment with anti-NRR3 resulted in about 61% of the cells in G0/G1, and addition of anti-NRR1 increased this figure to about 68%. In contrast, CCRF-CEM appears resistant to all of the tested treatments (FIG. 10A-10F), each showing from about 52-57% of the cells in G0/G1. HBP-ALL appears sensitive to both DAPT and anti-NRR1 treatment (each showing about 67% of cells in G0/G1), but not anti-NRR3 treatment (showing about 37% of cells in G0/G1) (FIG. 11A-11F).

Figure 14:
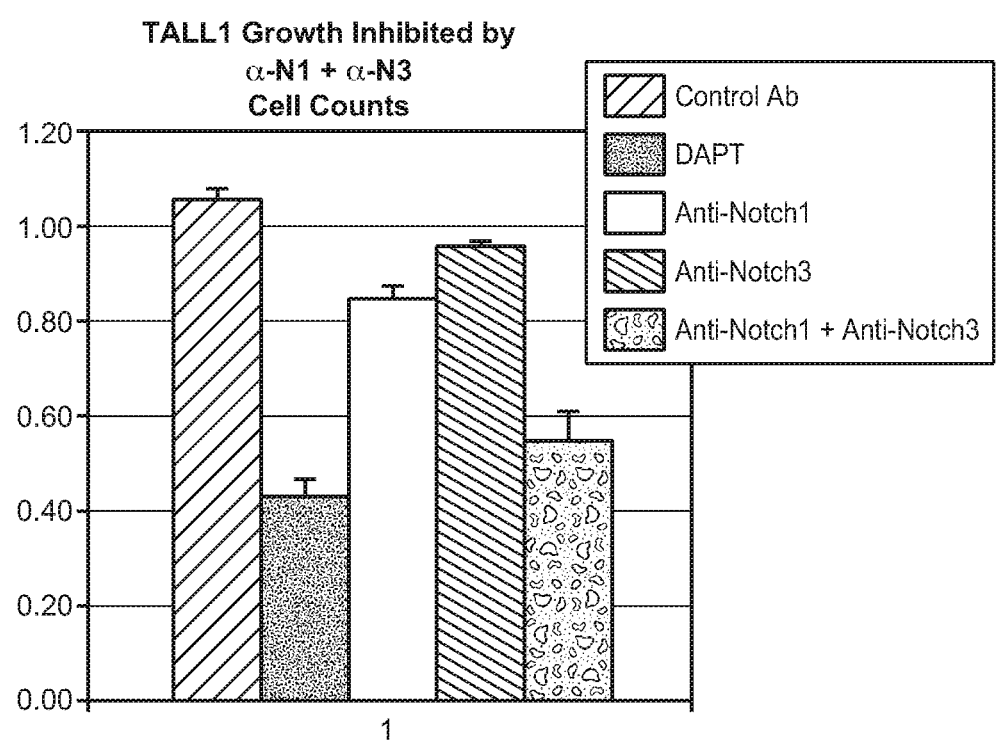
FIG. 14 shows a graph of the results of the experiments depicted in FIG. 9A-9F.

The results of the above experiment in FIG. 9B-9F are replotted in FIG. 14. The TALL-1 cell cultures started with approximately $5 \times 10^5$ cells/ml, and the y-axis is the number of cells/ml, in millions of cells, after treatment under the indicated conditions and as described for FIG. 9B-9F. FIG. 14 shows that anti-NRR1 and anti-NRR3 each individually resulted in lower cell counts. However the combination of anti-NRR1 and anti-NRR3 had a more pronounced effect in lowering cell counts, approaching the levels seen with DAPT.

C. Notch3 is Activated in Anti-NRR3-Sensitive Cells

Figure 12:
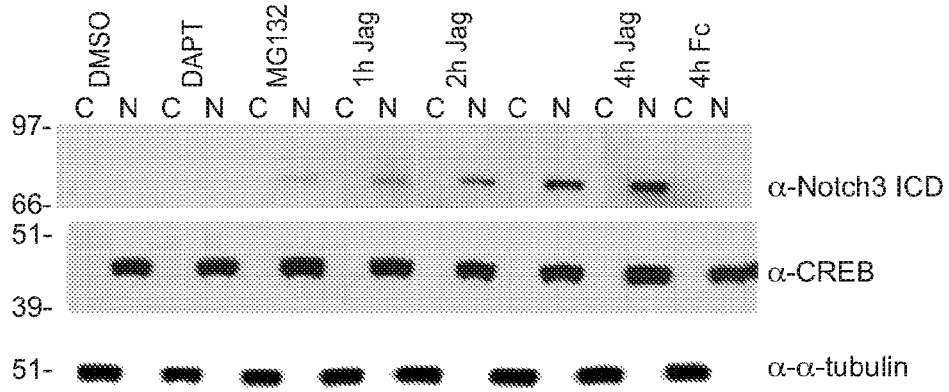
FIG. 12 shows an immunoblot using an antibody that recognizes activated Notch3 ICD (α-Notch3 ICD), which detects activated Notch3 ICD in the nuclear fraction of Jag 1-stimulated MDA-MB-468 cells.

To investigate the activation status of Notch3 in the three classes of T-ALL, a new anti-Notch3 ICD antibody was developed which recognizes cleaved (i.e., activated) Notch3 ICD. Using standard procedures, rabbit polyclonal antibodies were raised against a peptide corresponding to the N-terminus of the Notch3 ICD that is expected to result from gamma-secretase cleavage at the site S3. The peptide sequence used was: VMVARRKREHSTLW (SEQ ID NO:4). The peptide was conjugated to BSA for the immunizations. Polyclonal antibodies were purified on a protein A column and then used for immunoblotting, as shown in FIG. 12. To test whether the antibody recognized nuclear, cleaved Notch3 ICD, the basal breast cancer cell line MDA-MB-468 was used. This line expresses high levels of Notch3. Cells were treated with immobilized Jag1 (R&D Systems) (or Fc as a control) to induce Notch signaling, and cytoplasmic (C) and nuclear (N) fractions were isolated at the indicated times following induction. As a control to examine the level of Notch3 ICD present without Jag1 induction, cells that were not induced were treated with DAPT (5 μM), DMSO (vehicle for DAPT) or the proteasome inhibitor MG132 to stabilize the Notch3 ICD, as indicated. CREB and tubulin served as markers for nuclear and cytoplasmic proteins, respectively. The results in FIG. 12 show that the anti-Notch3 ICD antibody recognizes a band of the expected size that is localized to the nucleus and induced by Jag1.

Figure 13:
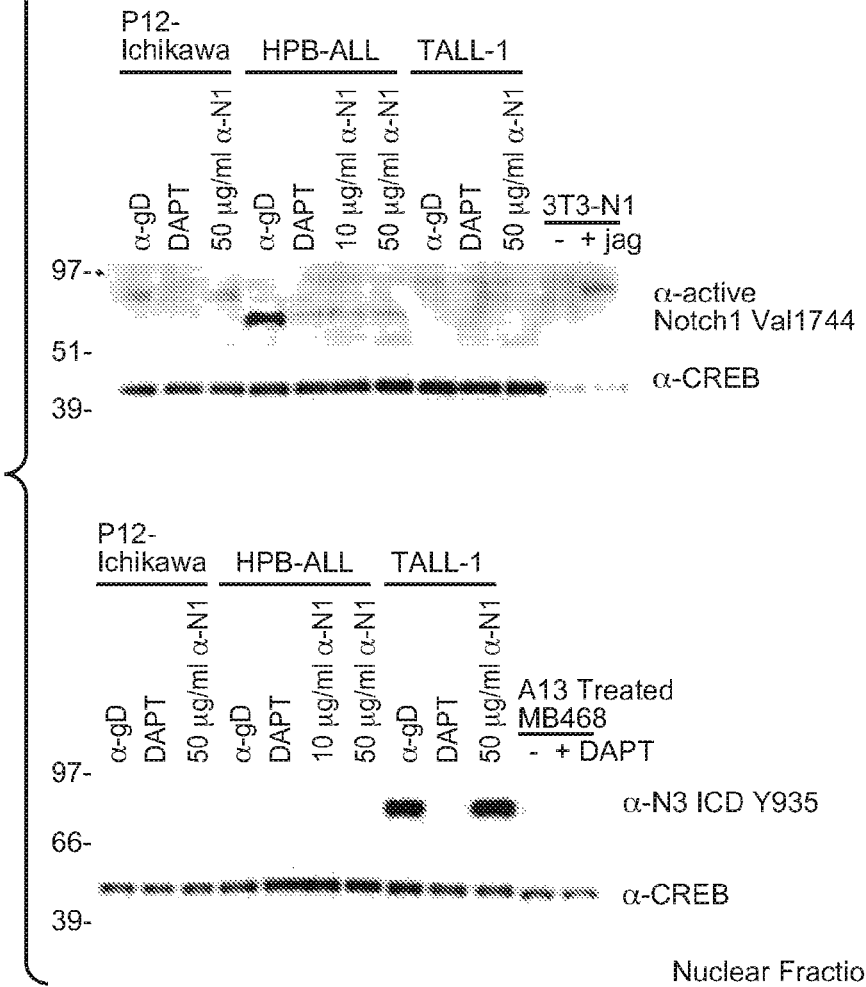
FIG. 13 shows that the TALL-1 cell line expresses high levels of cleaved, activated Notch3 (lower panel), which can be blocked by DAPT but not anti-NRR1 (α-N1), whereas the HPB-ALL cell line expresses high levels of cleaved, activated Notch1, which can be blocked by DAPT and anti-NRR1 (α-N1).

This new anti-Notch3 ICD antibody was then used to investigate the activation status of Notch3 in the three classes of T-ALL. As shown in FIG. 13, nuclear fractions of P12-Ichikawa, HPB-ALL, and TALL-1 cells were immunoblotted with anti-Notch1 Val1744, a commercially available polyclonal antibody that recognizes cleaved, activated Notch1 ICD (Cell Signaling Technologies) (upper panel), or with the anti-Notch3 ICD antibody (α-N3 ICD Y935, lower panel). 3T3 cells expressing Notch1 (3T3-N1) and MDA-MB-468 (MB468) cells were used as controls. Consistent with the growth inhibition studies described in the previous figures, TALL-1 expresses high levels of activated Notch3 but not activated Notch1 (compare TALL-1 lanes in lower and upper panels, respectively). Furthermore, production of activated Notch3 in TALL-1 could be blocked by DAPT but not anti-NRR1 (lower panel). Moreover, as expected, HPB-ALL cells express high levels of activated Notch1, which can be blocked by DAPT or anti-NRR1 antibody (see HPB-ALL lanes in upper panel). As to the controls, activated Notch1 is seen as a lighter, up-shifted band in the 3T3-N1 cells treated with Jagged (+jag) (upper panel). Additionally, activated Notch3 is seen as a faint but detectable band in the MDA-MB-468 cells treated with an anti-Notch3 agonist antibody (A13, described in U.S. Patent Application Publication US 2008/0118520 A1 as 256A-13) in the absence of DAPT (lower panel).

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

---

What is claimed is:

1. A method of treating a Gamma-secretase inhibitor (GSI)-responsive T-cell leukemia that does not respond to a Notch1-specific antagonist, the method comprising administering to a patient having such leukemia an effective amount of an anti-Notch3 antagonist antibody.

2. The method of claim 1, wherein the T-cell leukemia is a lymphoblastic leukemia.

3. The method of claim 2, wherein the lymphoblastic leukemia is T-lineage acute lymphoblastic leukemia (T-ALL).

4. The method of claim 1, wherein the anti-Notch3 antagonist antibody is an anti-Notch3 negative regulatory region (NRR) antibody.

5. The method of claim 4, wherein the anti-Notch3 NRR antibody binds to the LIN12/Notch Repeat A (LNR-A) and heterodimerization domain C (HD-C) domains of Notch3 NRR.

6. The method of claim 4, wherein the anti-Notch3 NRR antibody is a humanized form of antibody 256A-4 or 256A-8.

7. The method of claim 4, wherein the anti-Notch3 NRR antibody comprises the heavy and light chain variable region CDRs of antibody 256A-4 or 256A-8.

8. The method of claim 1, wherein the anti-Notch3 antagonist antibody is an anti-Notch3 antibody that binds to one or more EGF-like repeats of Notch3.

9. The method of claim 8, wherein the antibody reduces binding of a ligand to Notch3.

10. The method of claim 1, further comprising administering an effective amount of an anti-Notch1 antagonist antibody.

11. The method of claim 10, wherein the anti-Notch1 antagonist antibody is an anti-Notch1 negative regulatory region (NRR) antibody.

12. The method of claim 11, wherein the anti-Notch1 NRR antibody binds to the LIN12/Notch Repeat A (LNR-A), LIN12/Notch Repeat B (LNR-B), and heterodimerization domain C (HD-C) domains of Notch1 NRR.

13. The method of claim 11, wherein the anti-Notch1NRR antibody is selected from Antibody A, A-1, A-2, and A-3.

14. The method of claim 11, wherein the anti-Notch1 NRR antibody comprises the heavy and light chain variable region CDRs of an antibody selected from Antibody A, A-1, A2, and A-3.

15. The method of claim 10, wherein the anti-Notch1 antagonist antibody is an anti-Notch1 antibody that binds to one or more EGF-like repeats of Notch1.

16. The method of claim 1, wherein treating the patient reduces the number of proliferating cancerous cells in the patient, compared to pre-treatment levels.

\* \* \* \* \*